United States Patent [19]
Toyama et al.

[11] Patent Number: 5,453,612
[45] Date of Patent: Sep. 26, 1995

[54] CONTAINER INNER SURFACE TESTER EMPLOYING A TELEVISION CAMERA AND DIGITIZED IMAGE TO SCAN FOR DEFECTS

[75] Inventors: Kouichi Toyama; Tatsuo Yamamura, both of Kawasaki, Japan

[73] Assignee: Fuji Electric Co., Ltd., Kawasaki, Japan

[21] Appl. No.: 195,940

[22] Filed: Feb. 14, 1994

Related U.S. Application Data

[63] Continuation-in-part of Ser. No. 914,332, Jul. 15, 1992, Pat. No. 5,233,199, and a continuation-in-part of Ser. No. 970,280, Nov. 2, 1992.

[30] Foreign Application Priority Data

Feb. 12, 1993 [JP] Japan .................................. 5-023090

[51] Int. Cl.$^6$ .............................. G01N 9/04; G06M 7/00; H01J 40/14
[52] U.S. Cl. ........................................ 250/223 B; 348/127
[58] Field of Search ............................ 250/559, 223 B, 250/223 R; 382/8, 62, 67; 356/376, 377, 240; 209/526, 524; 348/125, 127, 128, 129

[56] References Cited

U.S. PATENT DOCUMENTS

| | | | |
|---|---|---|---|
| 4,086,497 | 4/1978 | Murray | 250/562 |
| 4,175,236 | 11/1979 | Juvinall | 250/566 |
| 4,428,674 | 1/1984 | Giebel et al. | 356/240 |
| 4,682,220 | 7/1987 | Beurskens | 358/106 |
| 4,701,612 | 10/1987 | Sturgill | 250/223 B |
| 4,735,508 | 4/1988 | Bellio | 356/371 |
| 4,775,899 | 10/1988 | Yoshida | 358/106 |
| 4,943,713 | 7/1990 | Yoshida | 250/223 B |
| 5,233,199 | 8/1993 | Toyama | 250/223 B |
| 5,338,000 | 8/1994 | Toyama | 250/223 B |
| 5,349,435 | 9/1994 | Hall et al. | 356/240 |

*Primary Examiner*—David C. Nelms
*Assistant Examiner*—Steven L. Nichols
*Attorney, Agent, or Firm*—Greer, Burns & Crain, Ltd.

[57] ABSTRACT

The container inner surface tester extracts image information about the opening portion and the deformation of the inner surface of a test cylindrical container through an image recognizing technique, and checks the circularity of the opening portion of the container. If it is detected that the present cylindrical container indicates a major defect level higher than a minor defect level according to the check of the image inside the container, then the production line of containers is immediately stopped to minimize the occurrences of major defective containers. Furthermore, the cylindrical container inner surface tester identifies the adjacent point of cylindrical containers through calculations and logical operations according to the image information. Likewise, the cylindrical container inner surface tester extracts a test area of an opening portion of an image of a test cylindrical container according to calculations and logical operations, and performs various processes such as determining the acceptability of the extracted white or black level of an image. Furthermore, the cylindrical container inner surface tester converts image signal to a binary value using a binary threshold for use in detecting a picture element indicating a major defect more white or black, or a larger difference in intensity than a background picture element, compares the number of picture elements indicating a major defect for each window area with an area threshold for use in determining a major defect, and determines whether or not the present container has a major defect.

15 Claims, 49 Drawing Sheets

BOTTOM HIGHLIGHTED PORTION

OPENING HIGHLIGHTED PORTION

WINDOW

PB
LEFT ADJACENT POINT

PA
RIGHT ADJACENT POINT

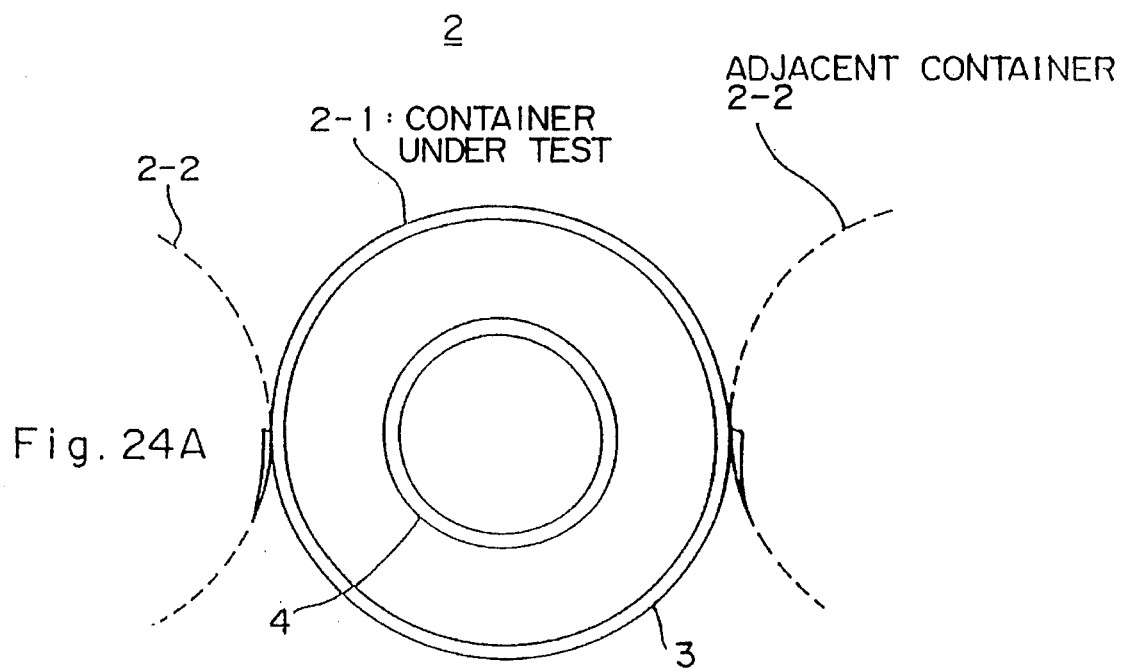
Fig. 24A
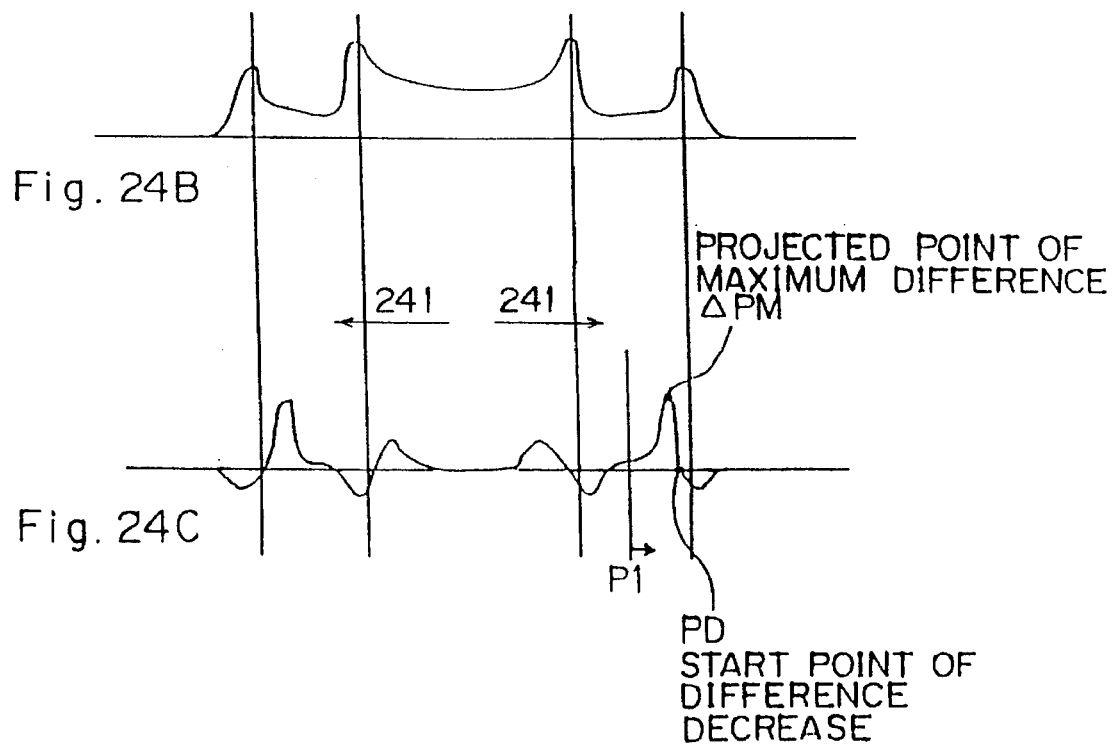
Fig. 24B
Fig. 24C

CONTAINER INNER SURFACE TESTER EMPLOYING A TELEVISION CAMERA AND DIGITIZED IMAGE TO SCAN FOR DEFECTS

CROSS REFERENCE TO RELATED APPLICATION

This application is a continuation-in-part application of both U.S. patent application Ser. No. 07/914,332 filed on Jul. 15, 1992, now U.S. Pat. No. 5,233,199, and U.S. patent application Ser. No. 07/970,280 filed on Nov. 2, 1992.

BACKGROUND OF THE INVENTION

1. Field of the Invention

The present invention relates to an image processing device, and more specifically to a container inner surface tester for checking the inner surface of a container to be carried on a conveyor, and for detecting foreign substances, dust, scratches, etc. on the surface.

2. Description of the Related Art

FIGS. 1A and 1B show views for explaining the method of checking a cylindrical container having metallic luster on its inner surface. FIG. 1A is a top view of a container viewed from above in the axis direction, and FIG. 1B is side cross-sectional view. 2 is a container, and 1 is a ring-shaped illuminator for illuminating the container 2 from above. The ring-shaped illuminator 1 and the container 2 are concentric. When the illuminator 1 evenly irradiates with its ring-shaped light the inner surface of the container 2, the light reflects on the surface having metallic luster. When the container is viewed from above, concentric intensity variations (hereinafter referred to as an illuminance pattern) can be observed inside the container. FIG. 1A shows a highlighted portion (a portion of halation) generated by a directly reflecting light of the illuminator. Among highlighted portions, an opening highlighted portion 3 and a bottom highlighted portion 4 indicate the largest intensity.

FIG. 2A shows a scanning line Q-Q1 running along the diameter of the container shown in FIG. 1A. FIG. 2B is the graph indicating changes in illuminance (intensity) inside the container along the scanning line Q-Q1. The graph can be obtained even if the line Q-Q1 is rotated with the center of the container set as the center of the rotation. The illuminance pattern changes depending on a container to be checked. That is, the highlighted portions and the non-highlighted portions appearing due to not reflecting a light in the direction of the point at which the container is viewed are generated depending on a container being checked. However, the feature that illuminance concentrically generates is maintained for any container. In the example shown in FIG. 2B, the intensity variations can be classified into 5 level area from W1 to W5. First area W1 corresponds to the opening highlighted portion 3; second area W2 corresponds to the internal upper middle part of the container indicating comparatively high intensity; third area W3 corresponds to the internal lower middle part of the side of the container subject to less amount of light of the illumination 1 shown in FIG. 1A indicating intensity lower than other portion of the container; fourth area W4 corresponds to the highlighted portion of the bottom; and fifth area W5 corresponds to the inner bottom of the container.

Conventionally, these areas W1–W5 are provided with a window individually and assigned thresholds used for detecting defects such as black spots (black points) and white spots (white points) according to the optical characteristics of each area. One method of detecting a defect is, for example, to convert by a predetermined threshold, a multi-value continuous tone image signal of 8 bits, etc. to a binary value. The signal is obtained by analog/digital(A/D)-converting an analog video signal (analog continuous tone image signal) obtained by scanning a target image. Another method is a differentiation method in which the above-described video signal is differentiated through a differentiation circuit shown in FIG. 3 to extract a defect signal. In the differentiation method, a differentiation signal can be obtained for the contour of a test object. While either of a positive pulse or a negative pulse is generated by the differentiation along the contour of a test object, these pulses are generated simultaneously at a fine defective point, thereby extracting a defect.

That is, if the following expressions exist between a value $P(i,j)$ and values $P(i-\alpha,j)$ and $P(i+\beta,j)$, where $P(i,j)$ indicates a target point (coordinates $x=i$ and $y=j$) referred to by a signal $P(x,y)$ obtained by differentiating an analog continuous tone image signal generated by a raster scanning operation, and $P(i-\alpha,j)$ and $P(i+\beta,j)$ indicate respective points positioned by predetermined number of $\alpha$ picture elements forward and positioned by predetermined number of $\beta$ picture elements backward of the above-described point $P(i,j)$ in the x direction of the scanning line.

$$P(i,j)-P(i-\alpha,j) > TH1 \text{ and}$$

$$P(i+\beta,j)-P(i,j) > TH1$$

where TH1 indicates a predetermined threshold (positive value).

Binary function values $PD(i,j)=i$ and $PD(i,j)=0$ are defined for detecting a defect on a target point and respectively indicate an defective black point and a non-defective point.

However, in the above-described defect detecting method, an optimum value of a threshold TH1 to be determined according to optical characteristics of a container inner surface changes. Accordingly, in the conventional method, a number of concentric circle windows are necessary as shown by windows W1–W5 in FIG. 2B (five windows in this case). Simultaneously, these windows must be assigned different thresholds TH1 (and coordinates $\alpha$, $\beta$). Thus, much time is wasted during the raster scanning operation, thereby offering a bottleneck to a high speed defect detection.

FIGS. 4A to 4C are views for explaining the problem in the conventional defect detecting method based on the differentiation method. FIG. 4A shows an example of intensity variations (analog continuous tone image signal) obtained by scanning along the scanning line Q-Q1; FIG. 4B shows an example of an analog differentiation signal shown in FIG. 4A; and FIG. 4C shows an example of a digital differentiation signal shown in FIG. 4A. The portions indicated by letters BD shown in FIGS. 4A–4C correspond to black spots. That is, there are following problems in the conventional defect detecting method in which a black level defect BD is extracted by a signal in the area having intensity variations as shown in FIG. 4A. In the analog differentiation method, a differentiation signal indicating a small defective point is superposed on a basic intensity differentiation signal due to a time constant of a filter circuit as shown in FIG. 4B. In the digital differentiation method, a signal indicates unstable values as shown in FIG. 4C, and a differentiation signal indicating a defective point is embedded in noise components, thereby getting in difficulties in detecting a defect signal according to a predetermined threshold.

FIG. 5A is a sample top view of a container 2 having a projected portion 2a which often generates highlighted portions 4-1, 4-2, etc. in series according to the form of the container's bottom or the variations in the reflection of a light from the side of the container. Specifically, most metallic containers have a mirror like inner surface and cause the above described problems.

Such highlighted portions can be hardly removed only by appropriately using an illumination. Therefore, the conventional defect detecting method has, in vain, to solve the above described uneven illumination generated as a highlighted portion inside a test container in testing its inner surface.

The first object of the present invention is to provide a cylindrical container inner surface tester for detecting a defective portion stably and precisely even though there is uneven illumination inside a test container.

Containers for containing food, etc. are generally manufactured in larger quantities per hour. When a fault has arisen in a container manufacturing device in a production line, a large number of defective products may be produced in a short time unless the production line is immediately stopped. The production line should recover from the trouble. However, it takes much time in recovering the line from the trouble and probably brings a considerable economic loss. If a container forming device is faulty, the trouble occurs that a large number of containers having major defects such as concavity, deformation are produced in series. FIG. 6 shows a major-defective container. In this example, the container has concavity 5 on its side. When the concavity 5 has arisen, the reflection pattern of a light inside a container becomes irregular, and the illuminance does not indicate a concentric pattern, thereby generating asymmetric highlighted portions and non-highlighted portions.

Conventionally, a consecutive defect monitoring process has been performed to prevent defective products from being produced in large quantities. In this process, a major defect threshold is preliminarily set in an inspection device. An occurrence of major defects is detected and a major defect alarm is issued if determination of a defective product is made consecutively and the number of defective products exceeds the predetermined consecutive defect threshold.

Furthermore, there is a conventional method of monitoring a defect rate. In this method, a rate of defect determination in the total number of times of acceptance/rejection determination is constantly monitored, and an inspection device calculates a floating defect rate each time determination is made to detect major defects and to issue a major defect alarm when the floating defect rate exceeds a defect rate threshold preliminarily set in the inspection device.

However, the consecutive defect monitoring method has the problem that it is very difficult to detect a major-defective container when it does not appear consecutively on a production line and the essential problem that major-defective containers may have been produced by the predetermined number (equal to a consecutive defect threshold) by the time a major-defective container is detected.

Also in the defect rate monitoring method, a delay arises between an actual occurrence of major defects and the detection of major defects by the inspection device, and a large number of major-defective containers are produced during the period of the delay.

Therefore, an occurrence of major defects should be detected not by the above described consecutive defect monitoring method or defect rate monitoring method, but should be immediately detected by individually checking each container.

Thus, the second object of the present invention is to provide a cylindrical container inner surface tester for reducing an economic loss by immediately stopping the production of major-defective containers after quickly detecting a major-defective container.

SUMMARY OF THE INVENTION

The object of the present invention is to determine a spot on the inner surface of the side of an axis-symmetrical cylindrical container having a predetermined form including a linear joint in its side surface, by illuminating the inside of the cylindrical container from above, capturing through a TV camera the illuminated surface of the cylindrical container from above in the axis direction of the cylindrical container, and analyzing the captured image.

To solve the above described first problem, the cylindrical container inner surface tester illuminates from above in the axis direction of the container, the inner surface of an axis-symmetrical cylindrical container. A TV camera captures the illuminated area of the cylindrical container from above in the axis direction. Then, the captured image is analyzed to determine a black or white spot inside the cylindrical container comprises a frame memory for storing, as image data corresponding to the captured image, a multi-value tone continuous image signal (PO, etc.), that is, an A/D conversion signal of a continuous tone image signal obtained by scanning the captured image; and an area detecting unit (area detecting circuit) for generating a binary image signal by converting using a predetermined threshold (THG, etc.) to a binary value a multi-value continuous tone image signal read by a horizontal or vertical scanning of the frame memory, and a circuit for determining a test target area from the first rise point to the last fall point of the binary image signal in each scanning process.

The cylindrical container inner surface tester further comprises a window gate circuit for masking, with predetermined masking pattern data, an area having different optical properties in a test target area detected by the area detecting unit with, for example, a mask rise point and a mask fall point.

According to the present invention, a target picture element value and two background picture element values are extracted. The target picture element value (coordinates x=i and y=j) at a target point PO(i,j) are associated with a multi-value continuous tone image signal PO(x,y) based on the raster scanning operation. The background picture element values of two background points PO(i+α,j) and PO(i-α,j) indicate the value of the points each picture elements forward and backward of the above described point PO(i,j) in the x direction of the scanning line are extracted. Then, the intensity relationship where the relationship among these three points indicates a valley when detected as a black level while it indicates a peak when detected as a white level is detected (that is, the difference in intensity between a background picture element value and a target picture element value is detected). The target picture element value PO(i,j) is determined to be a defective picture element when the absolute value indicating the difference in the intensity exceeds a predetermined threshold THD.

However, the multi-value continuous tone image signal PO is read by scanning a frame memory, and is extracted as a signal for a portion, of a fixed binary-conversion signal corresponding to the signal PO, within a test target area from the first rise point to the last fall point.

Setting a target point in a non-defective portion, a forward background point and a backward background point of a non-defective portion respectively positioned by the number of α picture elements forward and backward of the target point in the scanning line.

If the following expressions exist when the coordinates of a target point are (i,j) (that is, x=i and y=j), a binary function value POD(i,j)(referred to as a binary defective peak/valley image signal) for detecting a defect on a target point equals 1, and the target point is determined to be a valley (defect).

$$PO(i-\alpha,j)-PO(i,j)>THD \quad (1) \text{ and}$$

$$PO(i+\alpha,j)-PO(i,j)>THD \quad 2)$$

where THD indicates a predetermined threshold (positive value).

The above described expression (2) does not hold for the non-defective portion and no defects are detected. However, expressions (1) and (2) exist in the defective portion and a valley defect is detected.

Thus, an optimum detecting performance can be realized by dividing a waveform into a plurality of small areas and appropriately assigning to each of the small areas a threshold THD and the number of picture elements indicated in expressions (1) and (2) above.

According to the present invention, when a peak (defect) is detected the target point is determined to be a defective peak having the peak/valley binary image signal POD(i,j)=i if the following expressions exist where the position of the difference paragraph in each of the above described expressions (1) and (2) is exchanged with the other paragraph as follows.

$$PO(i,j)-PO(i-\alpha,j)>THD \quad (1A) \text{ and}$$

$$PO(i,j)-PO(i+\alpha,j)>THD \quad (2A)$$

The cylindrical container inner surface tester illuminates the inner surface of an axis-symmetrical cylindrical container from above in the axis direction of a container by a ring-shaped illuminator. A TV camera captures the illuminated area of the cylindrical container from above in the axis direction. Then, the captured image is analyzed to determine a spot or deformation inside the cylindrical container.

The image of the inner surface of the cylindrical container is scanned along a concentric circle or spiral scanning line (hereinafter referred to as a circular scanning line), which is centered on the center of the image and varies sequentially per cycle, of a radius varying every one or more picture elements predetermined. Then, the absolute value indicating the difference between the intensity of the target picture elements among a plurality of picture elements arranged at intervals such that one or more picture elements are arranged between two target picture elements and the intensity of background picture element positioned by predetermined number of a plurality of picture elements forward or backward of the target picture element is compared with a threshold predetermined according to the position of the circular scanning line. The above described processes are repeated for each target picture element, and a defect detecting unit determines a defective container inner surface when an absolute value larger than the value of the difference between the above described intensity values is detected.

The above-mentioned threshold must be set as the optimum threshold per circle of the circular scanning line.

The intensity of the background picture element refers to an average intensity value among the picture elements in a predetermined one-dimensional or two-dimensional local area centered on the background picture element.

The tester according to the present invention illuminates from above in the axis direction of a container the inner surface of an axis-symmetrical cylindrical container using a ring-shaped illuminator. When a TV camera captures the illuminated area of the cylindrical container from above in the axis direction and the captured image is analyzed, the distribution of the continuous tone on the container inner surface is concentrically generated. Taking this into account, a picture element string is obtained by scanning the container inner surface along the ring or spiral circular scanning line. When a defective concave exists, it appears as a continuous tone in the scanned picture element string. Thus, the absolute value ΔP indicating the difference between the intensity P0 of the target picture elements in a scanned picture element string and the intensity P1 of the background picture element d picture elements forward or backward of the target picture element is calculated by the following equation.

$$\Delta P = \|P_0 - P_1\|$$

A threshold THP is assigned to each of windows and the threshold THP is compared with the absolute value ΔP indicating the difference between the intensity values. If ΔP is larger than the THP, the target picture element is determined to be a picture element of a defective inner surface such as a concave, etc.

However, the threshold THP can be set per circle of the circular scanning line, for example, according to its position. The intensity P1 of the background picture element can be an average intensity value among picture elements in a one-dimensional local area (that is, a series of n picture elements on the scanning line) or a two-dimensional local area (that is, a local area comprising n picture elements by n picture elements.

To solve the above described second problem, the cylindrical container inner surface tester detects a defective container by irradiating the inner surface of a cylindrical container using a ring-shaped illuminator concentric with the axis-symmetric cylindrical container, capturing the irradiated surface of the cylindrical container using a TV camera from above along the axis of the container, and analyzing the captured concentric picture images. The tester stores, as screen data corresponding to a screen displaying the captured image, in its frame memory a multi-value continuous tone image signal (P0, etc.) as an A/D conversion signal of a continuous tone image signal obtained by scanning the screen displaying the captured image. The tester divides an image area on the inner surface of the cylindrical container into a plurality of window areas through which a picture element indicating a defect can be detected. For each of the window areas, a first fixed binary threshold for detection of a picture element indicating a black defect (hereinafter referred to as a first black level) and a first fixed binary threshold for detection of a picture element indicating a white defect (hereinafter referred to as a first white level) are set. Then, the tester obtains a sum of the number of picture elements indicating black and white defects for each window area after converting to a binary value a multi-value continuous tone image signal read by scanning the frame memory with the first black and white levels set for each window area. Finally, the tester determines (through a minor-defect-detecting binarization circuit, etc.) whether or not the test cylindrical container is a major-defective container based on the value of the sum (whether or not the sum exceeds a first area threshold set for each window area for detection of a major-defective container). For each of the above described window areas, a second fixed binary threshold corresponding to a black level at least higher than the first black level (hereinafter referred to as a second black level) is set; a second fixed binary threshold corresponding to a white level at least higher than the first white level (hereinafter referred to as a second white level) is set; and a second area threshold having a value larger than the first area threshold for detection of a major-defective container is set if at least the first black level is equal to the second black level and the first white level is equal to the second white level. If a sum of the number of picture elements indicating a black defect and a white defect for each window area in which a binary conversion level is represented by the second black level and the second white level exceeds the second area threshold set for each window area, then a major defect detection signal indicating that the present container is a major-defective container is outputted externally. Furthermore, the cylindrical container inner surface tester successfully reduces the required amount of hardware by regarding the first black level, the first white level, or the first area threshold as being equal to the second black level, the second white level, or the second area threshold respectively.

The cylindrical container inner surface tester detects a defective container by irradiating the inner surface of a cylindrical container using a ring-shaped illuminator concentric with the axis-symmetric cylindrical container, capturing the irradiated surface of the cylindrical container using a TV camera from above along the axis of the container, and analyzing the captured concentric picture images. The tester stores, as screen data corresponding to a screen displaying the captured image, in its frame memory a multi-value continuous tone image signal (PO, etc.) as an A/D conversion signal of a continuous tone image signal obtained by scanning the screen displaying the captured image. The tester divides an image area on the inner surface of the cylindrical container into a plurality of window areas through which a picture element indicating a defect can be detected. For each of the window areas, a first difference binary threshold for detection of a picture element indicating a defect (hereinafter referred to as a first difference level) is set. The number of picture elements indicating a defect in en each window area is obtained by converting to a binary with the first difference level set for each window area the absolute value of the difference obtained by subtracting the value of a target picture element in a screen scanning line for a multi-value continuous tone image signal read by scanning the frame memory from the value of a background picture element backward or forward by the number of picture elements predetermined for a corresponding window area. The cylindrical container inner surface tester determines whether or not the present cylindrical container is defective depending on whether or not the above described number of picture elements indicating a defect exceeds the first area threshold for detection of a defective container set for the present window area. For each of the above described window areas, a second difference binary threshold corresponding to a difference at least higher than the first difference level (hereinafter referred to as a second difference level) is set; and a second area threshold having a value larger than the first area threshold for detection of a major-defective container is set if at least the first difference level is equal to the second difference level. If the number of picture elements for each window area in which a binary conversion level is represented by the second difference level exceeds the second area threshold set for each window area, then a major defect detection signal indicating that the present container is a major-defective container is outputted externally. Furthermore, the cylindrical container inner surface tester successfully reduces the amount of required hardware by regarding the first difference level or the first area threshold as being equal to the second difference level or the second area threshold respectively. Additionally, the cylindrical container inner surface tester according to the present invention automatically stops the production of cylindrical containers according to the major defect detection signal.

The cylindrical container inner surface tester displays, when the major defect detection signal is outputted, the name of the window area associated with the major defect detection signal on the screen through which the test conducted according to the present invention is monitored.

BRIEF DESCRIPTION OF THE DRAWINGS

One skilled in the art can easily understand additional features and objects of this invention from the description of the preferred embodiments and some of the attached drawings. In the drawings:

FIGS. 24A, 24B and 24C show views for explaining how to detect an adjacent point according to the present invention;

DESCRIPTION OF THE PREFERRED EMBODIMENT

Figure 4A:
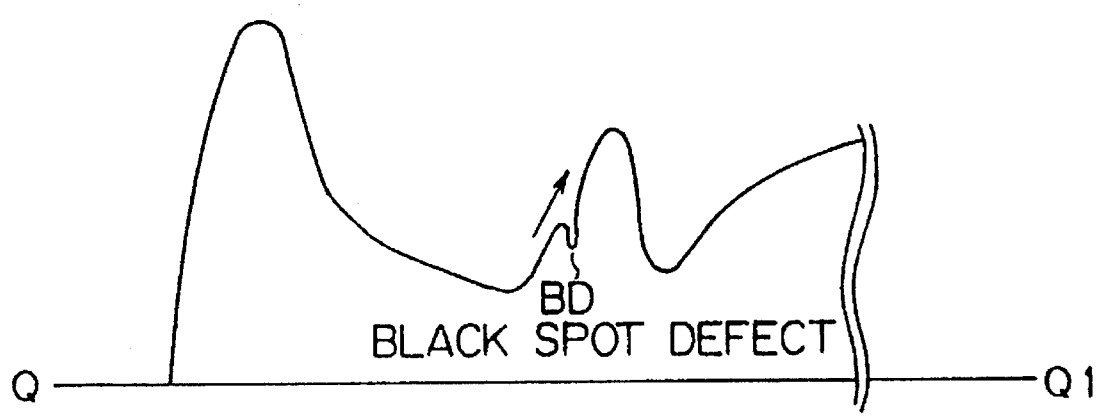
FIGS. 4A, 4B and 4C show views for explaining the conventional method of detecting a defect.
Figure 4B:
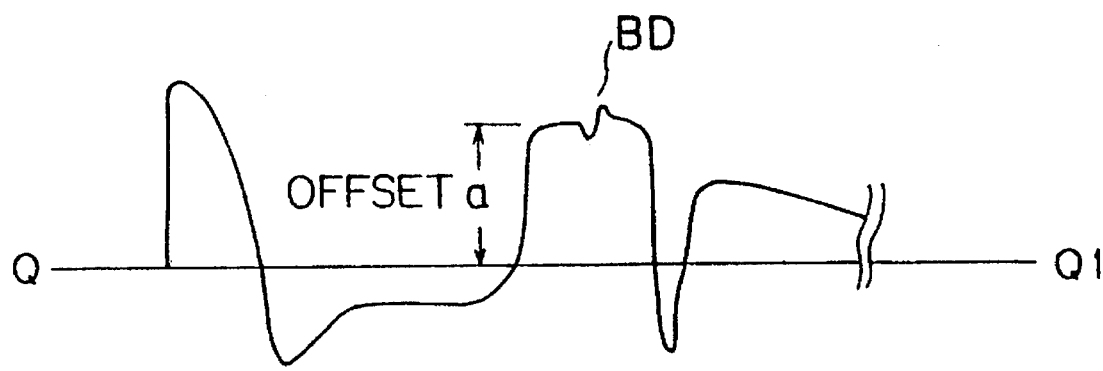
Figure 4C:
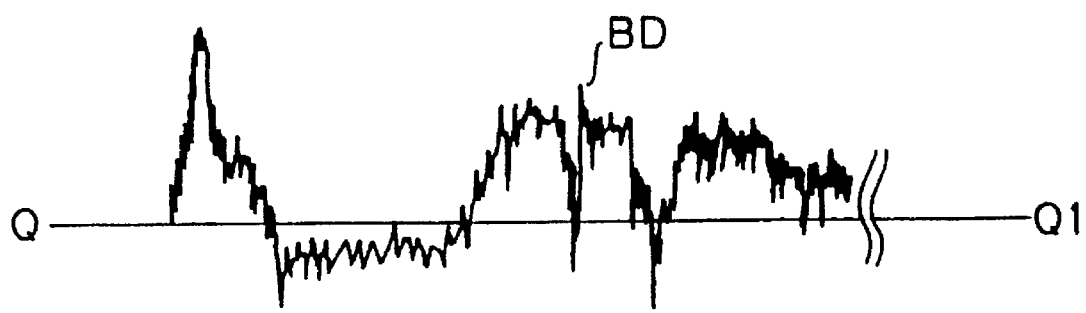

FIGS. 4A, 4B and 4C show views for explaining the problem in the conventional defect detecting method based on the differentiation method. FIG. 4A shows an example of intensity variations (analog continuous tone image signal) obtained by scanning along the scanning line Q–Q1; FIG. 4B shows an example of an analog differentiation signal shown in FIG. 4A; and FIG. 4C shows an example of a digital differentiation signal shown in FIG. 4A. The portions indicated by BDs shown in FIGS. 4A–4C refer to black spots. That is, there are following problems in the conventional defect detecting method in which a black level defect BD is extracted by a signal in the area having intensity variations as shown in FIG. 4A. In the analog differentiation method, a differentiation signal indicating a small defective point is superposed on a basic intensity differentiation signal due to a time constant of a filter circuit as shown in FIG. 4B. In the digital differentiation method, a signal indicates unstable values as shown in FIG. 4C, and a differentiation signal indicating a defective point is embedded in noise components, thereby getting in difficulties in detecting a defect signal according to a predetermined threshold.

Figure 5A:
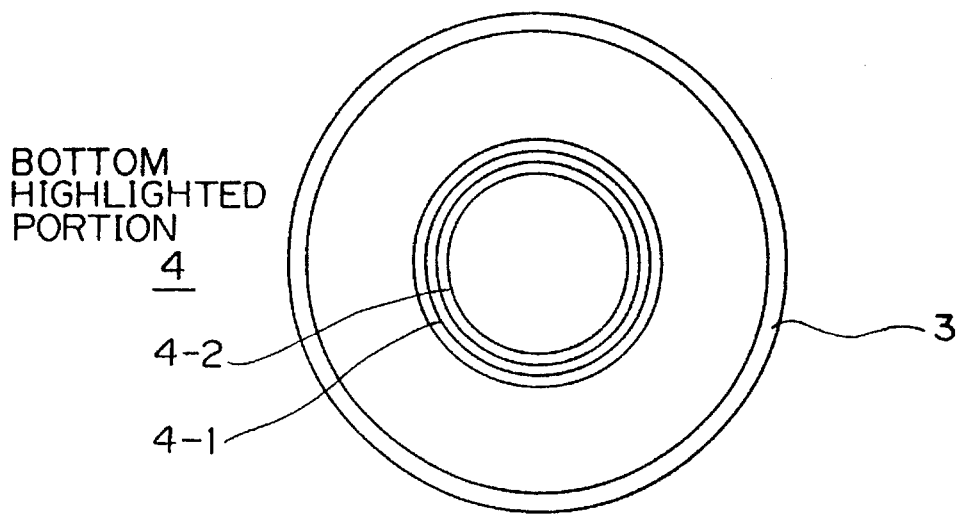
FIGS. 5A and 5B show the highlighted portion inside a container having an unusual bottom shape.
Figure 5B:
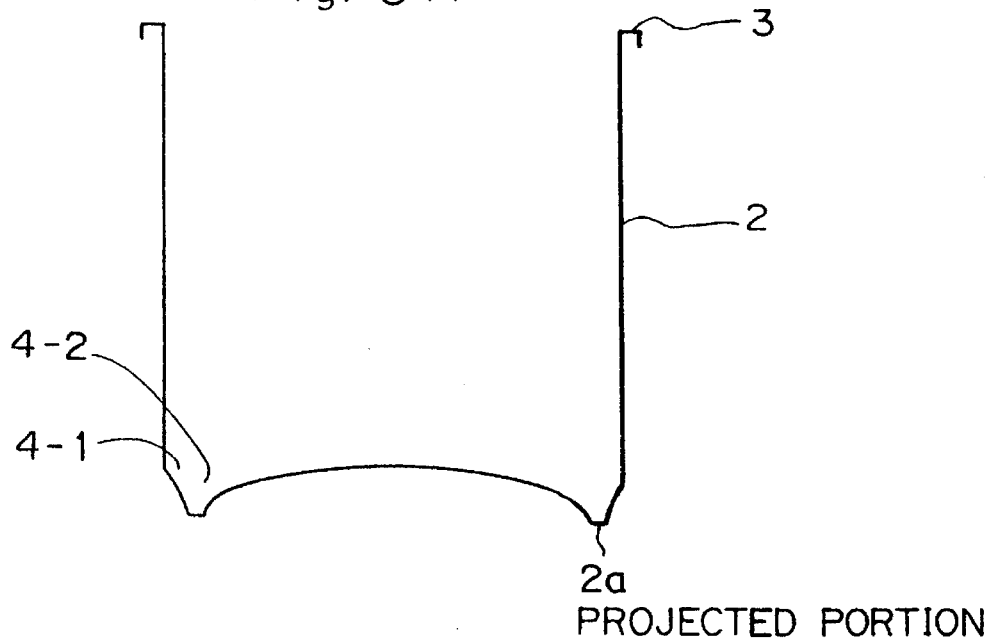
Figure 6:
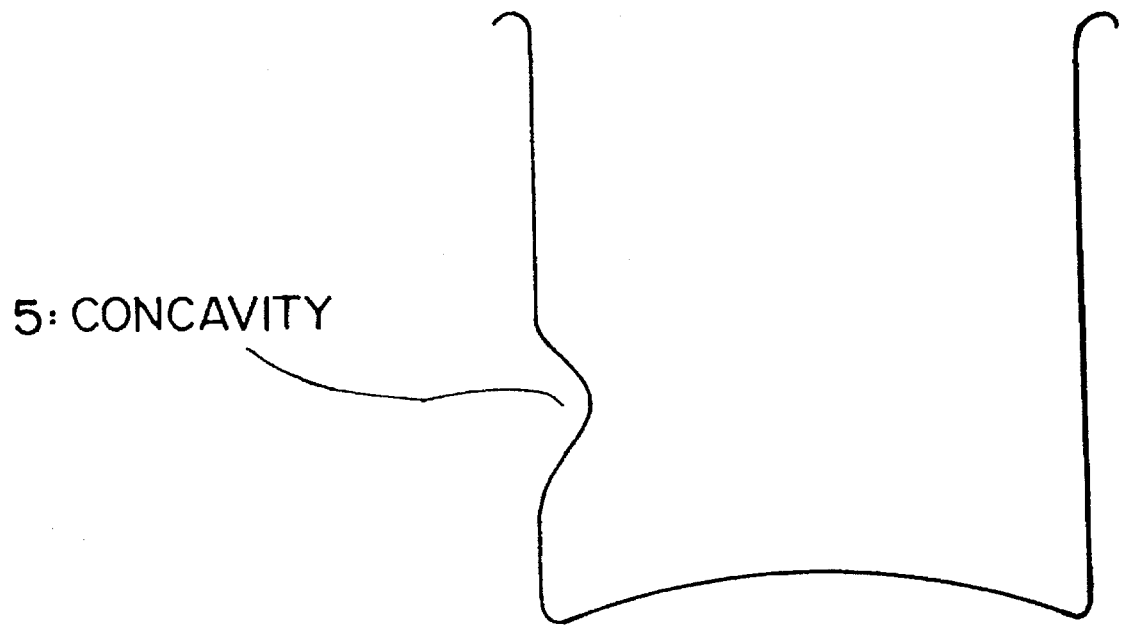
FIG. 6 shows an example of a major defect of a cylindrical container.

FIG. 5A shows the top view of a container having a projected portion 2a which often generates highlighted portions 4-1, 4-2, etc. in series according to the form of the container's bottom or the variations in the reflected light from the side of the container and FIG. 5B shows its side cross-sectional view. Specifically, most metallic containers have a mirror like inner surface and cause the above described problems.

Such highlighted portions can be hardly removed only by appropriately using an illumination. Therefore, the conventional defect detecting method has, in vain, to solve the above described uneven illumination generated as a highlighted portion inside a test container in testing its inner surface.

An object of the present invention is to provide a cylindrical container inner surface tester for detecting a defective portion stably and precisely even though there is uneven illumination inside a test container.

Figure 1A:
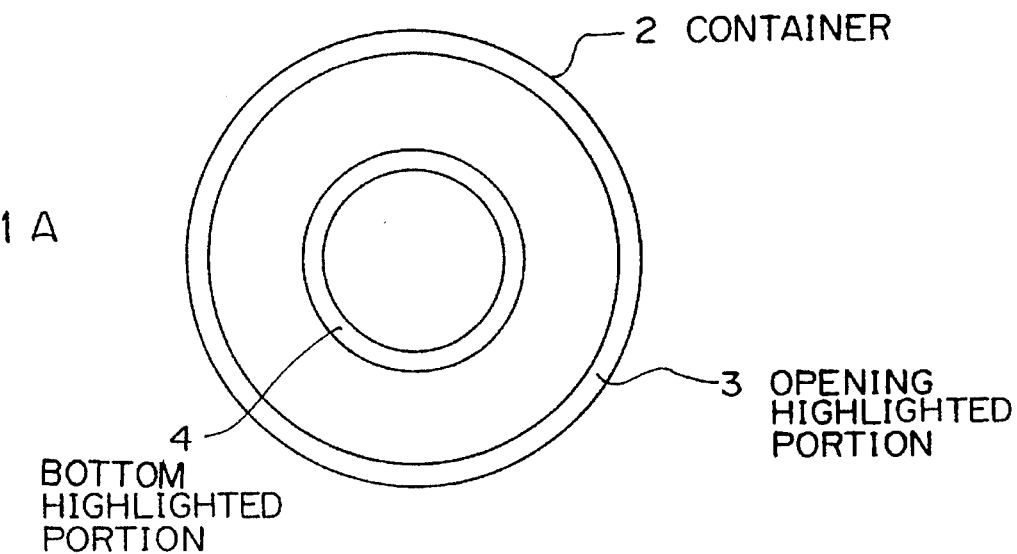
FIGS. 1A and 1B show views for explaining the method of checking a cylindrical container.
Figure 1B:
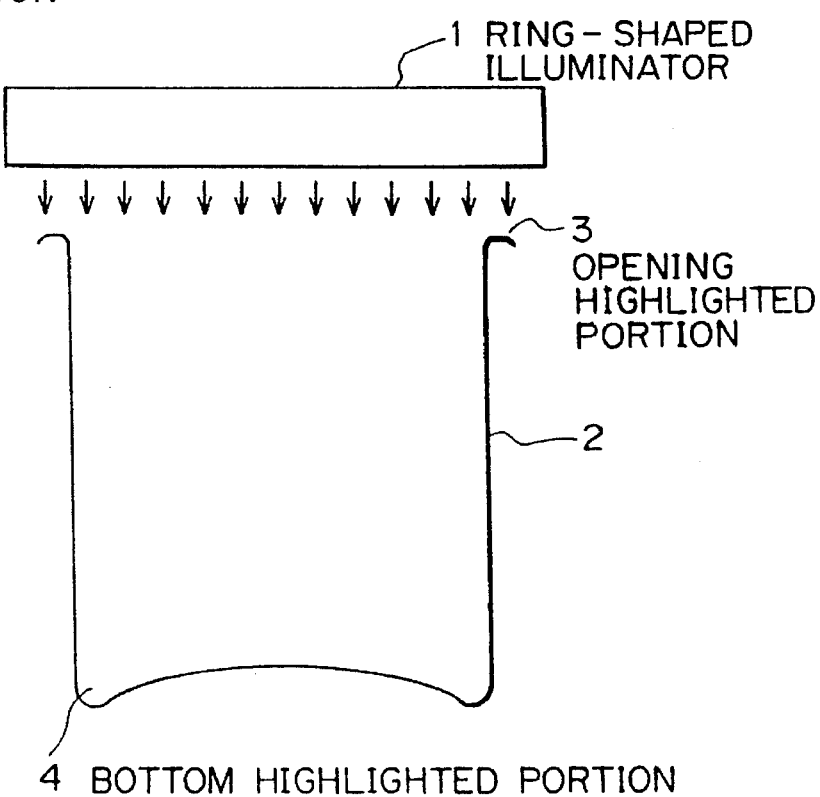

To solve the above described problems, the cylindrical container inner surface tester illuminates from above in the axis direction of a container (for example, by a ring-shaped illuminator 1 shown in FIG. 1B) the inner surface of an axis-symmetrical cylindrical container (2 shown in FIG. 1B, for example). A TV camera picks up the illuminated area of the cylindrical container from above in the axis direction. Then, the picked-up image is analyzed by a defect detecting unit (for example, a defect detecting circuit 27, a detected defect determining circuit 32, etc. shown in FIG. 8 which will be explained hereinafter) to determine a black or white spot inside the cylindrical container.

The tester is also provided with a circularity tester (an image edge detecting circuit 26, a highlighted portion determining circuit 31, etc.) for testing the circularity of a highlighted area in the picked-up image, and determines the acceptability of the inner surface of the cylindrical container according to the check results of the defect detecting unit and the circularity tester (through a final determining circuit 35, etc.).

To solve the above described problems, the cylindrical container inner surface tester illuminates from above in the axis direction of a container (for example, by a ring-shaped illuminator 1) the inner surface of an axis-symmetrical cylindrical container (2, for example) capable of being arranged adjacently to others in a predetermined direction (for example, in the horizontal direction). A TV camera picks up the illuminated area of the cylindrical container from above in the axis direction. Then, the picked-up image is analyzed by a defect detecting unit (for example, a defect detecting circuit 27, a detected defect determining circuit 32, etc.) to determine a black or white spot inside the cylindrical container.

The tester comprises a scanning-line-direction position specifier (an image edge detecting circuit 26, etc.). The specifier obtains a binary image signal by performing a binary conversion, for the purpose of obtaining a binary image of the opening highlighted (3, for example) of the cylindrical container, on an image signal (for example, a multi-value continuous tone image signal PO) obtained by scanning the picked-up image. Then, it specifies the position of the test cylindrical container in the scanning-line direction according to the coordinates of the middle points (MA, MB, etc.) between first rise points (A0, B0, etc.) and last fall points (A1, B1, etc.) in the same scanning line of a binary image signal, among the above described binary image signals, in the area not affected by the above described adjacent arrangement (area except the area E, etc.).

In the cylindrical container inner surface tester, the above described position specifier defines an average value of a plurality of coordinates of middle points in the scanning lines as a specific value indicating the above described position.

To solve the above described problems, the cylindrical container inner surface tester illuminates from above in the axis direction of a container (for example, by a ring-shaped illuminator 1) the inner surface of an axis-symmetrical cylindrical container (2, for example) capable of being arranged adjacently to others in a predetermined direction (for example, in the horizontal direction). A TV camera picks up the illuminated area of the cylindrical container from above in the axis direction. Then, the picked-up image is analyzed by a defect detecting unit (for example, a defect detecting circuit 27, a detected defect determining circuit 32, etc.) to determine a black or white spot inside the cylindrical container.

The tester comprises a projector (a Y projecting circuit 30, etc.) and an adjacent area isolator (a process area determining circuit 34, etc.). The projector obtains a binary image signal by performing a binary conversion, for the purpose of obtaining a binary image of the opening highlighted (3, for example) of the cylindrical container, on an image signal (for example, a multi-value continuous tone image signal PO) obtained by scanning the picked-up image. Then, it projects the above described binary image signal in the direction perpendicular to the above described adjacent arrangement direction (in the Y direction, etc.). The adjacent area isolator obtains the difference in the number of image elements between the normal image and the projected image, checks the difference in the number of picture elements from the center of the image of the cylindrical container to its circumference (to the opening of the container), detects a point where the difference in the number of picture elements exceeds a predetermined threshold (for example, the maximum difference projection point $\Delta PM$) in the area from the center to a point where the difference in the number of picture elements first falls to a negative, adds a predetermined correction value ($\beta$, for example) to the coordinates of the detected point, and extracts the above described adjacent arrangement area using the resultant coordinates.

To solve the above described problems, the cylindrical container inner surface tester illuminates from above in the axis direction of a container (for example, by a ring-shaped illuminator 1) the inner surface of an axis-symmetrical cylindrical container (2, for example). A TV camera picks up the illuminated area of the cylindrical container from above in the axis direction. Then, the picked-up image is analyzed to determine a black or white spot inside the cylindrical container.

The cylindrical container's inside surface tester comprises a defective peak/valley determiner (for example, an antecedent of an AND gate in a peak/valley detection binary-conversion circuit 44), an image test area divider, and a value changer.

The defective peak/valley determiner determines that a target picture element is defective if two differences obtained by subtracting the value (for example, $PO(i,j)$) of a target picture element in the same picture element scanning line for a continuous tone image signal (test area continuous tone image signal 43a, etc.) which is obtained by scanning the above described picked-up image from the values ($PO(i+\alpha,j)$, $PO(i-\alpha,j)$, etc.) of two background picture elements (hereinafter referred to as a forward background picture element and a backward background picture element respectively) by a predetermined number of picture elements (hereinafter referred to as picture elements) positioned backward or forward of the target picture element indicate the same polarity, if an absolute value of one of the above described two differences is larger than a predetermined first threshold (THD, for example) corresponding to the polarity, and if the other absolute value is larger than a predetermined second threshold (THD, for example).

The divider divides (into Z1–Z4, Za–Zc, etc.) the test area of a target image of the defective peak/valley determiner according to the optical features of a cylindrical container inner surface illuminated by the above described illuminator.

The value changer changes at least one value among the number of the above described $\alpha$ picture elements, the first threshold, and the second threshold.

The tester comprises a frame memory for storing as the data for the above described captured image a multi-value continuous tone image signal A/D-converted from a continuous tone image signal obtained by scanning the captured image, and an area detecting unit for generating a binary image signal by binary-converting using a predetermined threshold a multi-valve continuous tone image signal read by horizontally or vertically scanning the frame memory and for determining as a test area the area between the first rise point and the last fall point of each scanning line of the binary image signal.

Another cylindrical container inner surface tester according to the above described tester further comprises a masking unit for masking using predetermined mask pattern data an area different in optical characteristics from that in a test area detected by the area detecting unit.

Another configuration is described below.

The captured image is analyzed to determine a black or white spot inside the cylindrical container. The image of the inner surface of the cylindrical container is scanned along a ring or spiral scanning line (hereinafter referred to as a circular scanning line) which is centered on the center of the image and varies sequentially per cycle of a radius varying every one or more picture elements predetermined. Then, the absolute value indicating the difference between the intensity of the target picture elements among a plurality of picture elements arranged at intervals such that one or more picture elements are arranged between two target picture elements and the intensity of background picture element by predetermined number of a plurality of picture elements positioned forward or backward of the target picture element is compared with a threshold predetermined according to the position of the circular scanning line. The above described processes are repeated for each target picture element, and a determining unit determines a defective container inner surface when an absolute value larger than the value of the difference between the above described intensity values is detected.

The above mentioned threshold must be set as the optimum threshold per circle of the circular scanning line.

The intensity of the background picture element refers to an average intensity value among the picture elements in a predetermined one- or two-dimensional local area centered on the background picture element.

Defects can be detected precisely by divisionally extracting highlighted portions after a binary conversion and checking the circularity of the divisionally extracted patterns to collectively detect the deformation, irregular concave, and black dust spots on test objects. Then, black and white spots are checked concurrently in the same window area, thereby reducing the number of window areas and performing the whole process at a high speed.

An average value of the coordinates of middle points between first rise points and last fall points in the same scanning line of a binary image signal in the area not affected by the above described adjacent arrangement is obtained to specify the position of a test cylindrical container prior to this circularity check.

The projected amount of the binary image of the highlighted portion at the opening projected in the direction perpendicular to the adjacent arrangement of containers is obtained to isolate a test area from the area of an adjacent container. Then, the difference between the normal image and the projected image is searched for from the center to the edge of the container so that the adjacent point can be detected.

A target picture element value and two background picture element values are extracted. The target picture element value (coordinates x=i and y=j) at a target point PO(i,j) are associated with a multi-valve continuous tone image signal PO(x,y) based on the raster scanning operation. The background picture element values of two background points PO(i+α,j) and PO(i−α,j) indicate the value of the points of each picture elements positioned forward and backward of the above described point PO(i,j) in the x direction of the scanning line are extracted. Then, the intensity relationship where the relationship among these three points indicates a valley when detected as a black level while it indicates a peak when detected as a white level is detected (that is, the difference in intensity between a background picture element value and a target picture element value is detected). The target picture element value PO(i,j) is determined to be a defective picture element when the absolute value indicating the difference in the intensity exceeds a predetermined threshold THD.

Figure 7A:
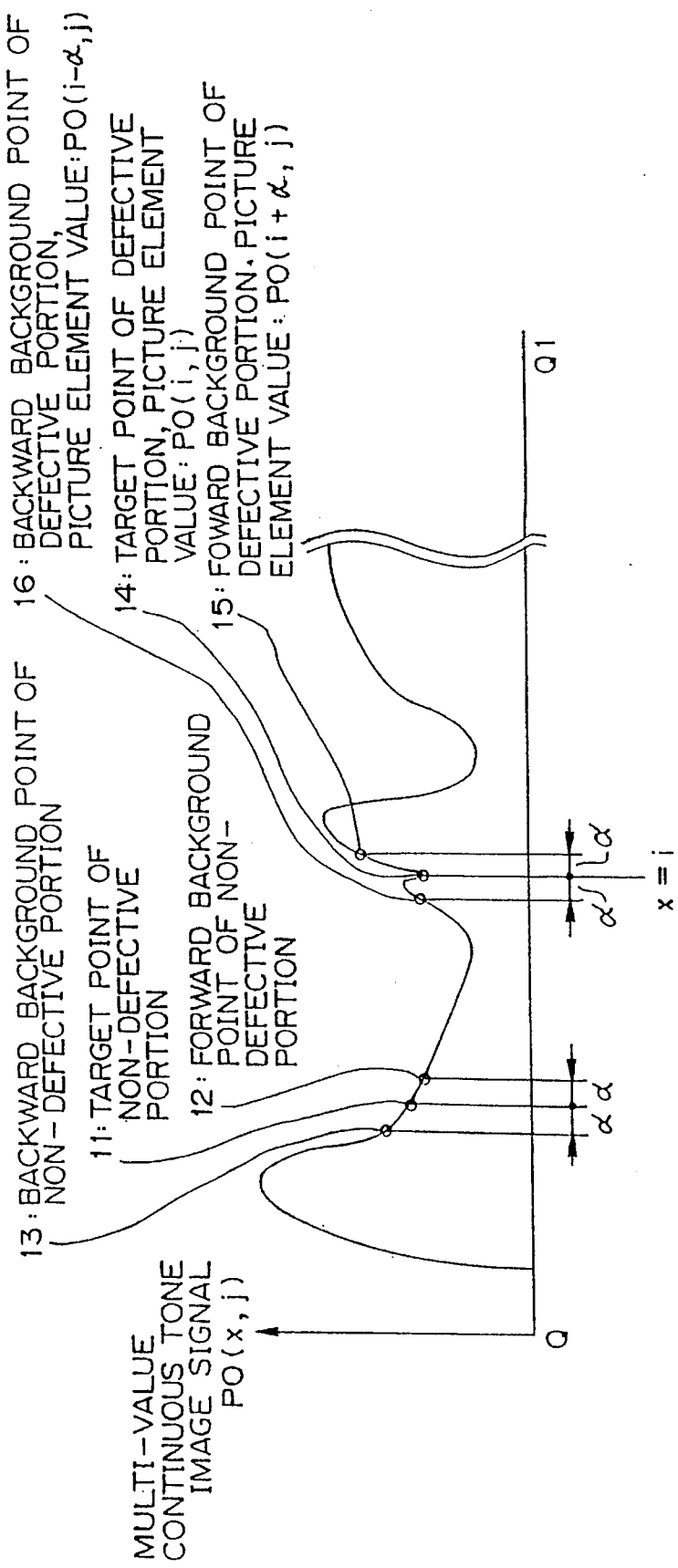
FIGS. 7A and 7B show the principle of the method of detecting a valley and performing a binary conversion.
Figure 7B:
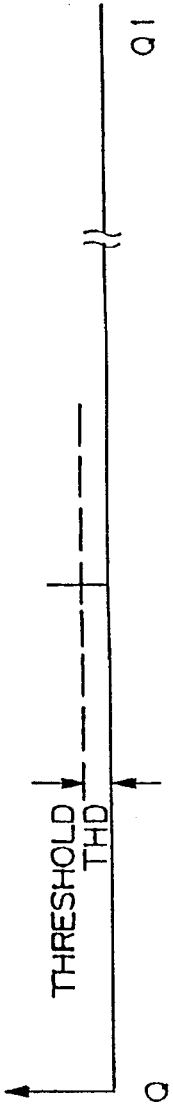

FIGS. 7A and 7B show the principle of the valley-detection binary-conversion method which is the most important point in the present invention. FIG. 7A shows an example of a multi-value continuous tone image signal PO(x,y) in the scanning line Q—Q'1 (y=j), where 11 is a target point in a non-defective portion; and 12 and 13 are forward background point and backward background point of a non-defective portion respectively which are picture elements positioned forward and backward of the target point 11 in the scanning line.

Likewise, 14 is a target point in a defective portion; and 15 and 16 are forward background point and backward background point of a non-defective portion respectively which are picture elements positioned forward and backward of the target point 14 in the scanning line.

If the following expressions exist when the coordinates of a target point are (i,j) (that is, x=i and y=j), a binary function value POD(i,j)(referred to as a binary defective peak/valley image signal) for detecting a defect on a target point equals 1, and the target point is determined to be a valley (defect).

$$PO(i-\alpha,j)-PO(i,j)>THD \quad (1)$$

and $$PO(i+\alpha,j)-PO(i,j)>THD \quad (2)$$

where THD indicates a predetermined threshold (positive value).

The above described expression (2) does not hold for the non-defective portion shown in FIG. 7A, and no defects are detected. However, expressions (1) and (2) exist in the defective portion shown in FIG. 7A and a valley defect is detected. FIG. 7B shows the above described peak/valley binary image signal POD (x,j) as an output of defect determination.

Thus, an optimum detecting performance can be realized by dividing the waveform shown in FIG. 7A into a plurality of small areas and appropriately assigning to each of the small areas a threshold THD and the number of picture elements indicated in expression (1) and (2) above.

When a peak (defect) is detected by the present invention, the target point is determined to be a defective peak having the peak/valley binary image signal POD(i,j)=i if the following expressions exist where the position of the difference paragraph in each of the above described expressions (1) and (2) is exchanged with the other paragraph as follows.

$$PO(i,j)-PO(i-\alpha,j)>THD \quad (1A)$$

and $$PO(i,j)-PO(i+\alpha,j)>THD \quad (2A)$$

Figure 2A:
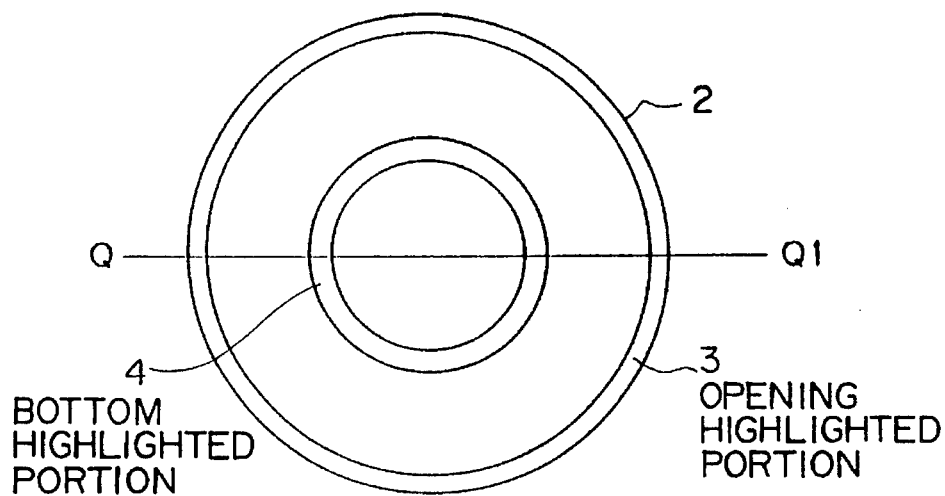
FIGS. 2A and 2B show views for explaining the distribution of illuminance variations inside a cylindrical container.
Figure 2B:
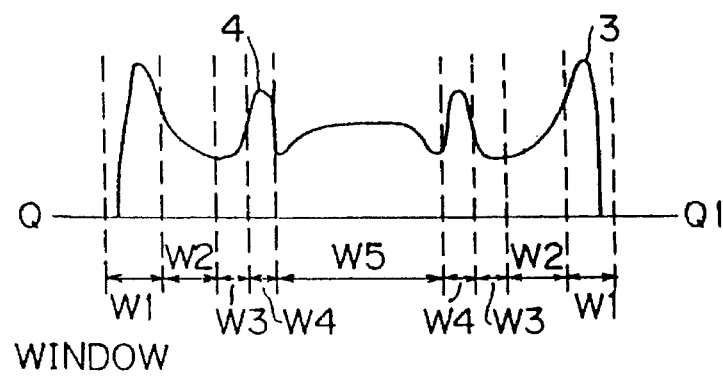
Figure 3:
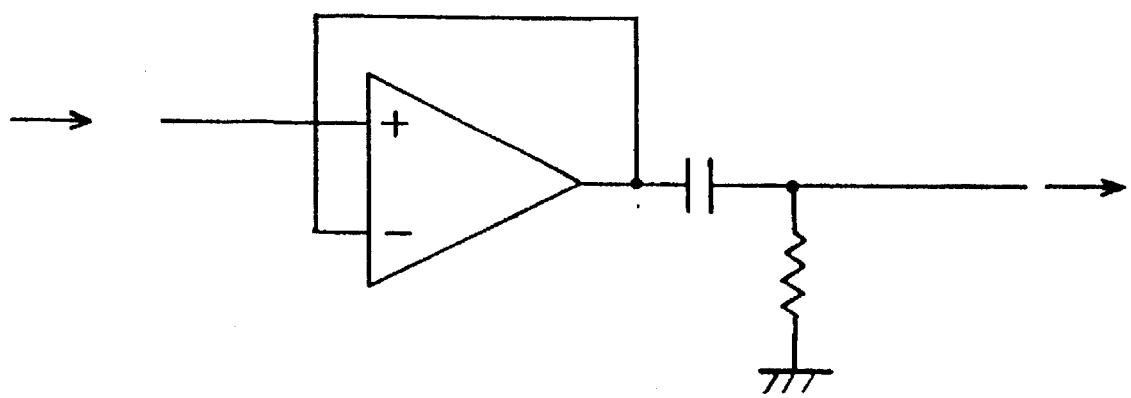
FIG. 3 shows an example of an analog differentiation circuit.

The tester for easily detecting defective concaves illuminates from above in the axis direction of a container the inner surface of an axis-symmetrical cylindrical container using a ring-shaped illuminator. When a TV camera captures the illuminated area of the cylindrical container from above in the axis direction and the captured image is analyzed, the distribution of the continuous tone on the container inner surface is concentrically generated as shown in FIGS. 2A and 2B. Taking this into account, a picture element string is obtained by scanning the container inner surface along the ring or spiral circular scanning line. When a defective concave exists, it appears as a continuous tone in the scanned picture element string. Thus, the absolute value ΔP indicating the difference between the intensity P0 of the target picture elements in a scanned picture element string and the intensity P1 of the background picture element by d picture elements positioned forward or backward of the target picture element is calculated by the following equation.

$$\Delta P = \|Po - P1\|$$

A threshold THP is assigned to each of the windows W1 through W5 shown in FIG. 2B, and the threshold THP is compared with the absolute value ΔP indicating the difference between the intensity values. If ΔP is larger than the THP, the target picture element is determined to be a picture element of a defective inner surface such as a concave, etc.

However, the threshold THP can be set per circle of the circular scanning line, for example, according to its position. The intensity P1 of the background picture element can be an average intensity value among picture elements in a one-dimensional local area (that is, a series of n picture elements on the scanning line) or a two-dimensional local area (that is, a local area comprising n picture elements by n picture elements.

Figure 8:
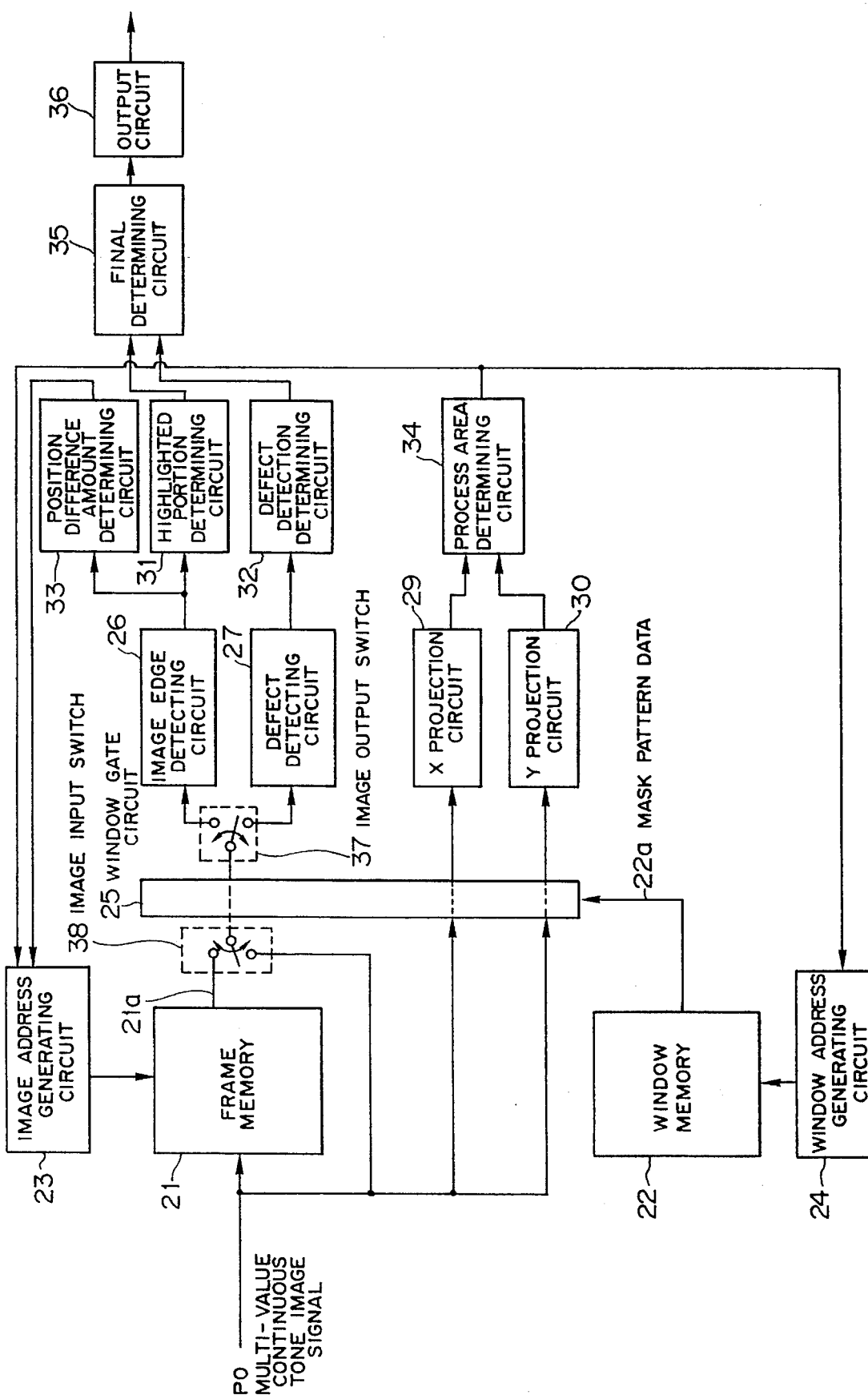
FIG. 8 is a block diagram of the hardware configuration of the first embodiment of the present invention.

The first embodiment of the present invention is explained by referring to FIGS. 8 through 25. FIG. 8 is a block diagram of hardware as the first embodiment of the present invention. In Figure, P0 is a multi-value (8-bit, for example) continuous image signal generated by AD-converting a video signal obtained by raster-scanning a screen of a TV camera; a frame memory 21 receives this multi-value continuous tone image signal P0 and stores it as a piece of multi-value screen data; and an address generating circuit 23 generates addresses for the frame memory 21. A window memory 22 stores a mask pattern prepared for each window; an address generating circuit 24 generates addresses for the window memory 22; and a window gate circuit 25 masks a multi-value continuous tone image signal PO or an image signal 21a read from the frame memory 21 with a mask pattern data 22a from the window memory 22, and passes the image signal PO or the image signal 21a in a specified window area.

An image input switch 38 selectively switches either to the multi-value continuous tone image signal PO or to the frame memory image signal 21a. The switch 38 applies to an image edge detecting circuit 26 the latest multi-value continuous tone image signal PO in parallel with an input of the signal PO to the frame memory 21 so that a position difference amount determining circuit 33 described later can be operated.

An image output switch 37 switches an output image signal from the image input switch 38 received through the window gate circuit 25 to the image edge detecting circuit 26 or a defect detecting circuit 27.

The image edge detecting circuit 26 detects the edge of an image, that is, the outer point (point in an outer circumference) and the inner point (point in the inner circumference) of a ring-shaped highlighted portion. In the detecting operation, an inputted image signal is converted into binary data using a predetermined threshold for detecting the position of a target image and for use in a circularity test, etc. Then, the coordinates of rise points and fall points of the binary signal are stored as image edge data in a memory (26A through 26D described later by referring to FIG. 13) of the image edge detecting circuit 26.

A circuit 31 checks the circularity on the coordinates of the points in an outer or inner circumference detected by the image edge detecting circuit 26.

To open a window at the right position relative to a target image, the position difference amount determining circuit 33 detects the difference amount between the center of the current target image detected by the input of the latest multi-value image signal PO from the image edge detecting circuit 26 and the center of a predetermined window.

The defect detecting circuit 27 detects a defect (black or white spot) by the differentiation method described in the column entitled "Description of the Related Art" and calculates an area, etc. A defect detection determining circuit 32 compares a detection result of the circuit 27 with a predetermined value to determine the acceptability.

An X projection circuit 29 obtains an X-direction projection pattern of a target image using a multi-value image signal PO received through the window gate circuit 25. Likewise, a Y projection circuit 30 obtains a Y-direction projection pattern of a target image. A process area determining circuit 34 determines the image area of a test container not adjacent to images of other containers using the data outputted from the two projection circuits 29 and 30.

A final determining circuit 35 receives determination results from the highlighted portion determining circuit 31 and the defect detection determining circuit 32 to give a final determination. An output circuit 36 indicates the acceptability of a test container according to an output determination signal outputted by the final determining circuit.

Figure 9A:
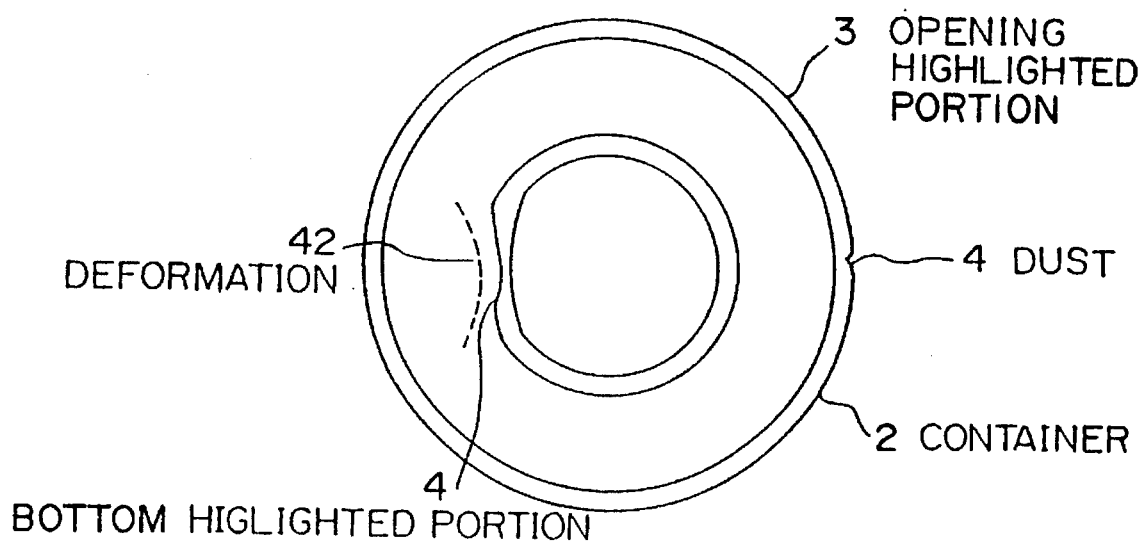
FIGS. 9A and 9B show the influence of a defective inner surface of a container on a highlighted portion.
Figure 9B:
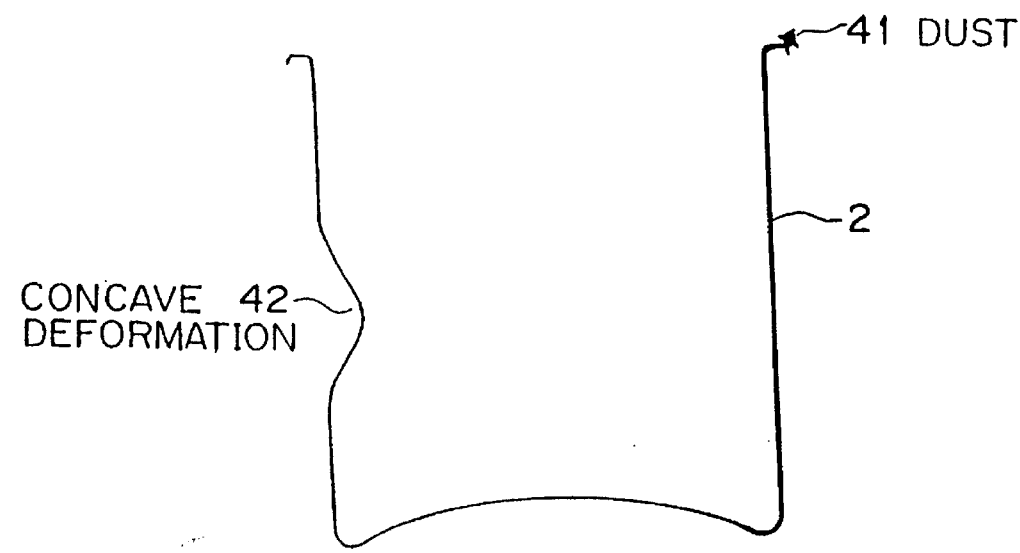

FIGS. 9A and 9B show views for explaining the influence of a defect in the highlighted portion of a can, which has a defect in the inner surface, observed from above. FIG. 9A is a plan view; and FIG. 9B is a cross-sectional view. When there is dust detected at the opening of a container 2, it is detected as a lack in a circumference which indicates the highlighted portion 3 at the opening as shown in FIG. 9A. If there is a big concave deformation 42 on the side of a container, it can be detected as a deformation in the bottom highlighted portion 4. However, unlike dust, etc., since a concave deformation indicates a small contrast difference, the concave deformation 42 can be easily detected by the circularity check performed on the bottom highlighted portion 4.

Figure 10:
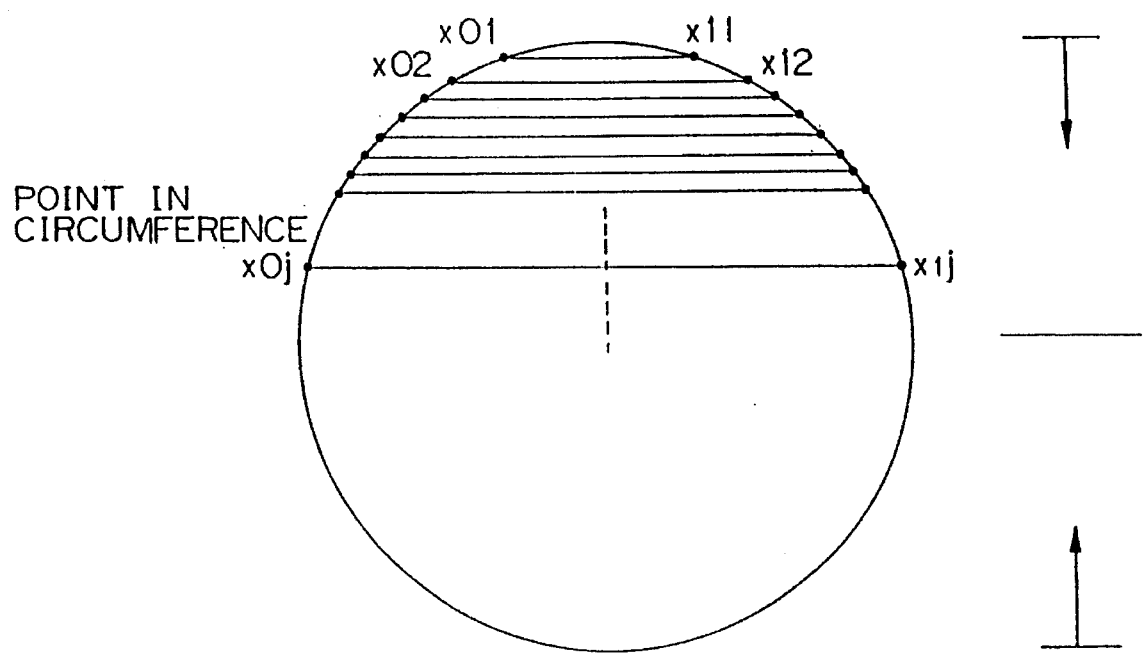
FIG. 10 is a view of points in the circumference of a highlighted portion which are used in a circularity check.

FIG. 10 is a view for explaining the circularity detecting method operated by the highlighted portion determining circuit 31. In FIG. 10, "x0j" and "x1j" respectively indicate a rise point and a fall point of coordinates of a point in an outer circumference which indicates a highlighted portion of a non-defective container (where j=1, 2, . . . , that is, j is a parameter corresponding to a coordinate of "y" in the horizontal scanning line). First, the coordinate variation $X_{k+1} - X_k$ of a non-defective container is calculated. Then, the maximum value (max (a,b) described later) and the minimum value (min (a,b) described later) which provide the above described allowable range are respectively stored in the maximum value table TB1 and the minimum value table TB2 each shown in FIG. 11 as allowable value tables TB. In this case, the value k is 0j or 1j.

In FIG. 10, since images are not stable at a several lines near the top and the bottom, they must be excluded or assigned a large allowable value. Therefore, the allowable value of $X_{K+1} - X_K$ is determined as follows based on the coordinate variation of a non-defective container.

$$min(a,b)-\alpha < X_{k+1}-X_k < max(a,b)+\alpha$$

where max(a,b) means the maximum value "a" or "b" (shown below) whichever is larger. Likewise, min(a,b) means the minimum value "a" or "b" whichever is smaller.

$$a=X_k-X_{k-1}$$

$$b=X_{k+2}-X_{k+1}$$

α is a fixed value for moderating a detected sensitivity in consideration of a quantization error, etc. generated when an image is converted to a digital image.

"a" and "b" can also be assigned to determine the allowable range of two lines as follows.

$$a=X_{k-1}-X_{k-2}$$

$$b=X_{k+3}-X_{k+2}$$

Figure 11:
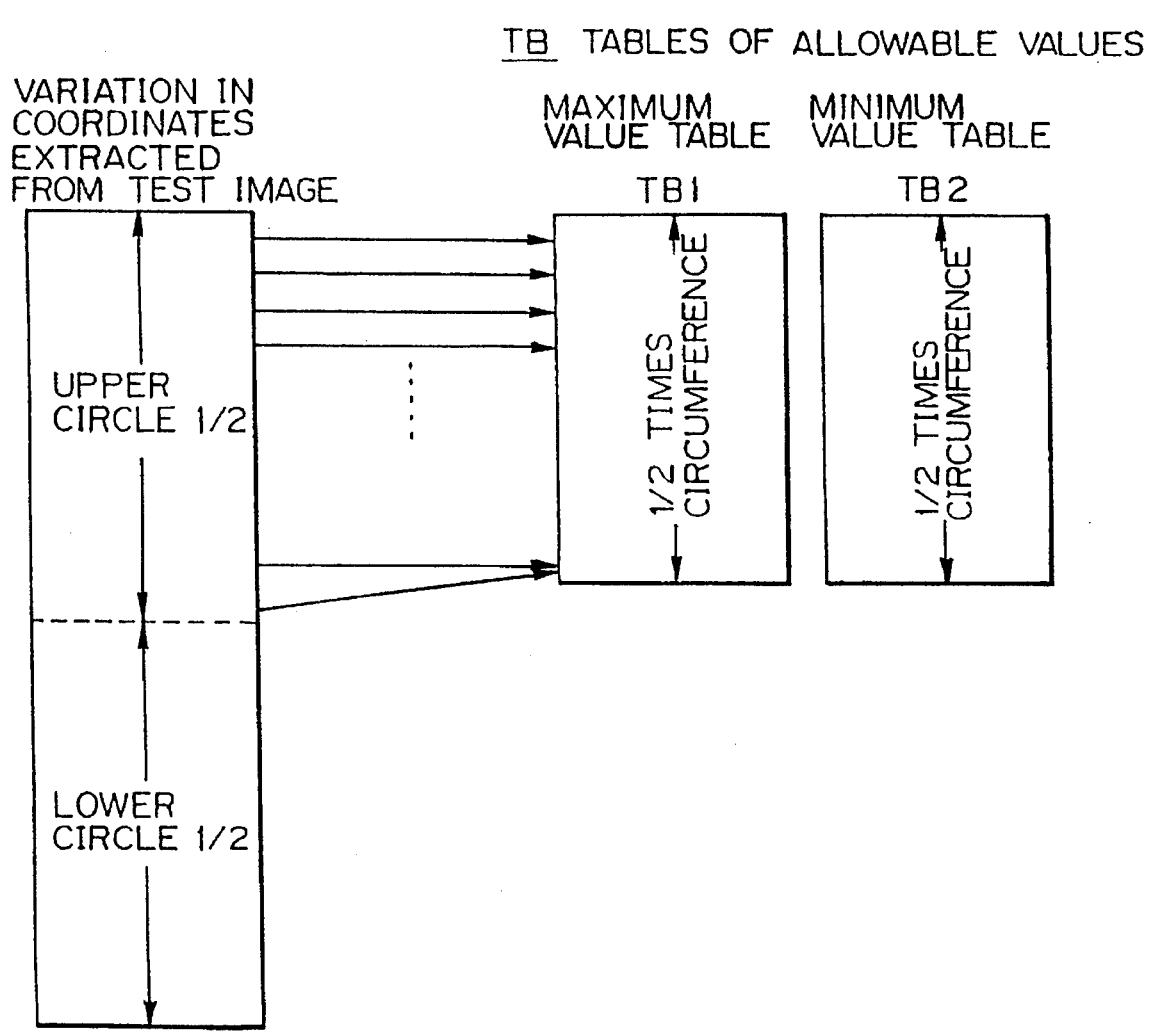
FIG. 11 is a block diagram for explaining the determination of the circularity.

Thus, the highlighted portion determining circuit 31 stores an allowable value of a non-defective container for each line as a maximum table TB1 and a minimum table TB2 shown in FIG. 11, and serially compares for a circularity test the variation in coordinates of a test image with the allowable value indicated in the table TB1 or TB2.

If a predetermined number of scanning lines of a non-defective container does not match the number of scanning lines of a test image, the above described comparison is performed serially from the top or the bottom of the container to its center. The difference in the number of scanning lines is balanced around the center where the variation is smaller than in upper or lower lines. That is, when the number of lines shown in the allowable table of a non-defective container is smaller, the comparison is performed using the allowable value for the center line (refer to FIG. 11). In FIG. 11, the same process is performed twice for an upper circle and a lower circle, and the allowable value table stores the values only for half a circle.

The above described test is performed for an outer circumference. The test method for an inner circumference is explained below.

Figure 12A:
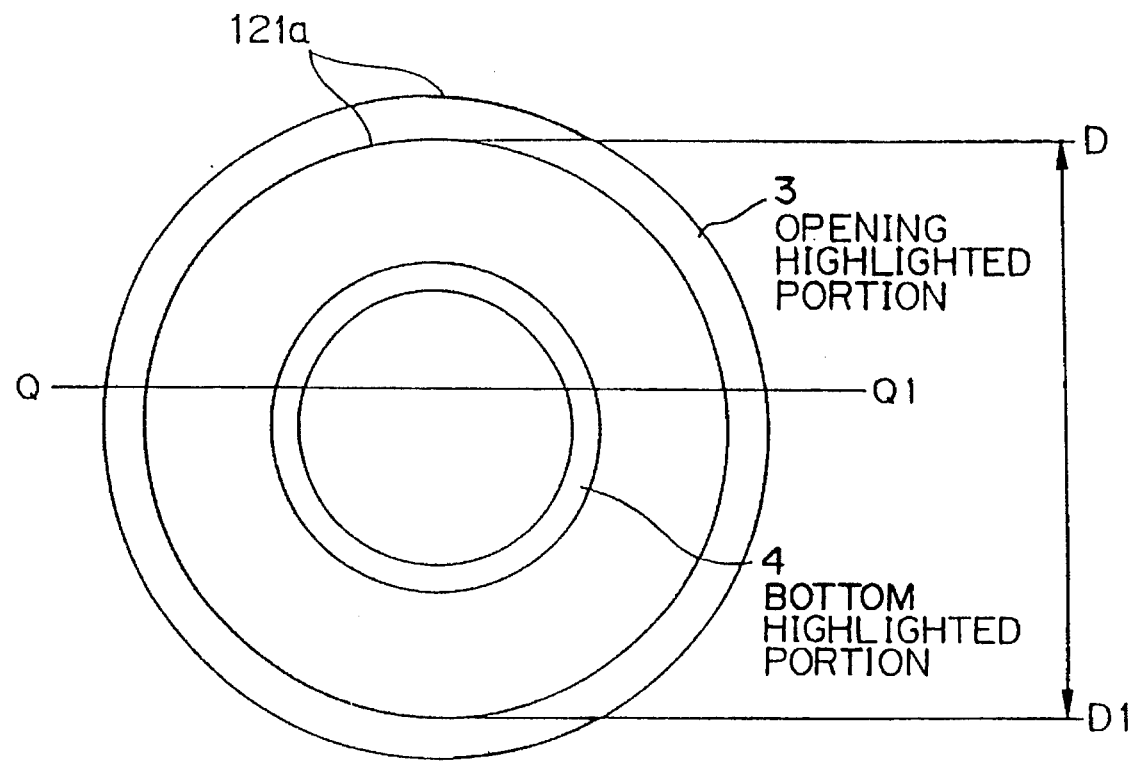
FIGS. 12A and 12B show view for explaining how to detect a point in an inner circumference of a highlighted portion.
Figure 12B:
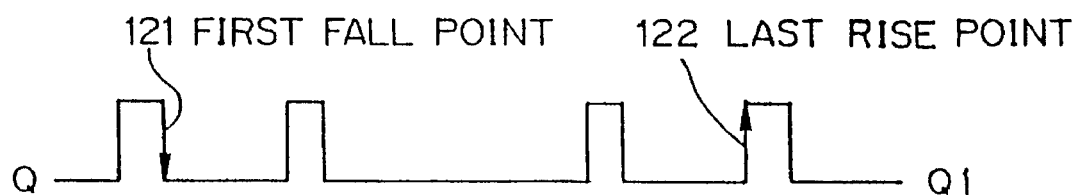

FIGS. 12A and 12B show views for explaining how to detect coordinates in an inner circumference of a highlighted portion. FIG. 12A is a plan view of a test container; and FIG. 12B shows in binary how continuous tone image signals change at the highlighted portions in the scanning line Q–Q1. First fall points of binary signals 121 in scanning lines shown in FIG. 12B detect the coordinates 121a indicated as the bold curves shown in FIG. 12A. Since the coordinates in the inner circumference range between D and D1, the line D–D1 is determined to be the line where the coordinate variation shows inversion, thereby obtaining the coordinates of the left half inner circle. Likewise, each of the last rise points 122 in each scanning line generates the right half inner circle. Thus, the circularity test is performed on the inner circumference.

Figure 13:
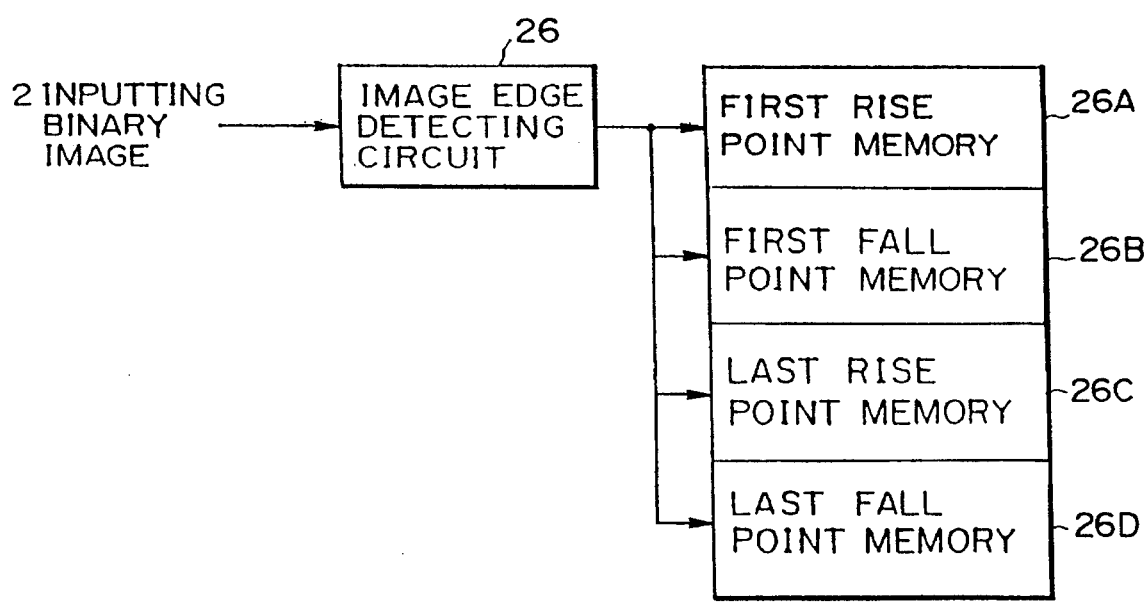
FIG. 13 is a block diagram of the detailed configuration of the image edge detecting circuit.

FIG. 13 shows the further detailed configuration of the image edge detecting circuit 26 shown in FIG. 8. In FIG. 13, a memory 26A stores a first rise point; a memory 26B stores a first fall point; a memory 26C stores a last rise point; and a memory 26D stores a last fall point. The data in the memories 26A and 26D enable an outer circumference to be detected, and the data in the memories 26B and 26C enables an inner circumference to be detected.

The deformation and a concave on a container, and dust attached to it can be detected with a high defect-detection precision when the above described outer circumference is tested in a circularity test on the highlighted portions.

Figure 14:
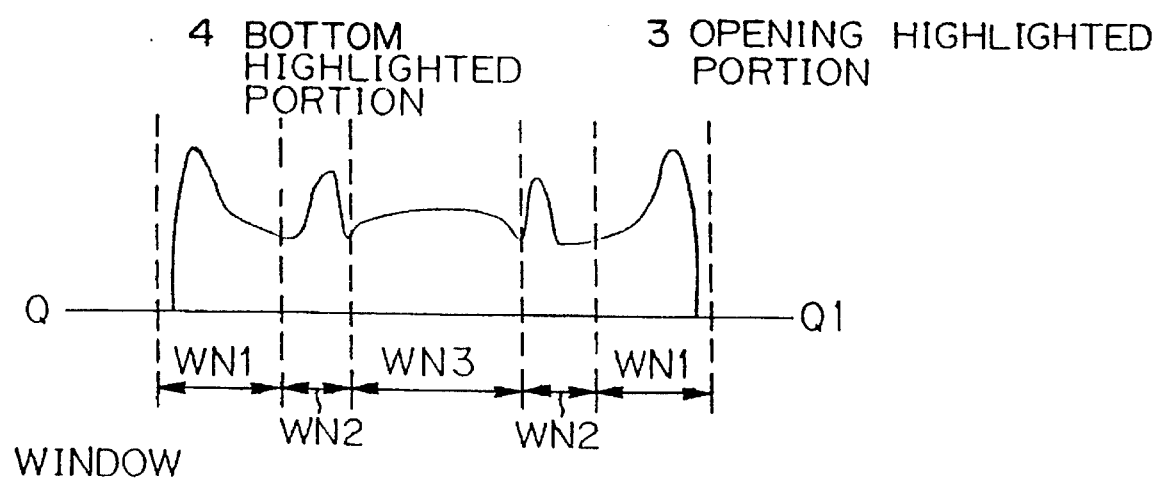
FIG. 14 shows the relationship between the intensity variations inside a cylindrical container and the division of a window based on the present invention.

Therefore, the number of windows can be reduced by concurrently detecting black and white spots through the circularity test and the conventional defect detecting circuit. FIG. 14 corresponds to FIG. 2B, and shows an embodiment of a window based on the present invention. That is, in FIG. 14, a new window WN1 is generated by combining a window W1 including the opening highlighted portion 3 shown in FIG. 2 and the adjacent window W2. Likewise, a new window WN2 is generated by combining a window W4 including the bottom highlighted portion 4 shown in FIG. 2 and the adjacent window W3. Another new window WN3 corresponds to a window W5 for the central part of the bottom shown in FIG. 2. Thus, there are three window areas WN1, WN2, and WN3, thereby decreasing the number of areas.

Figure 15:
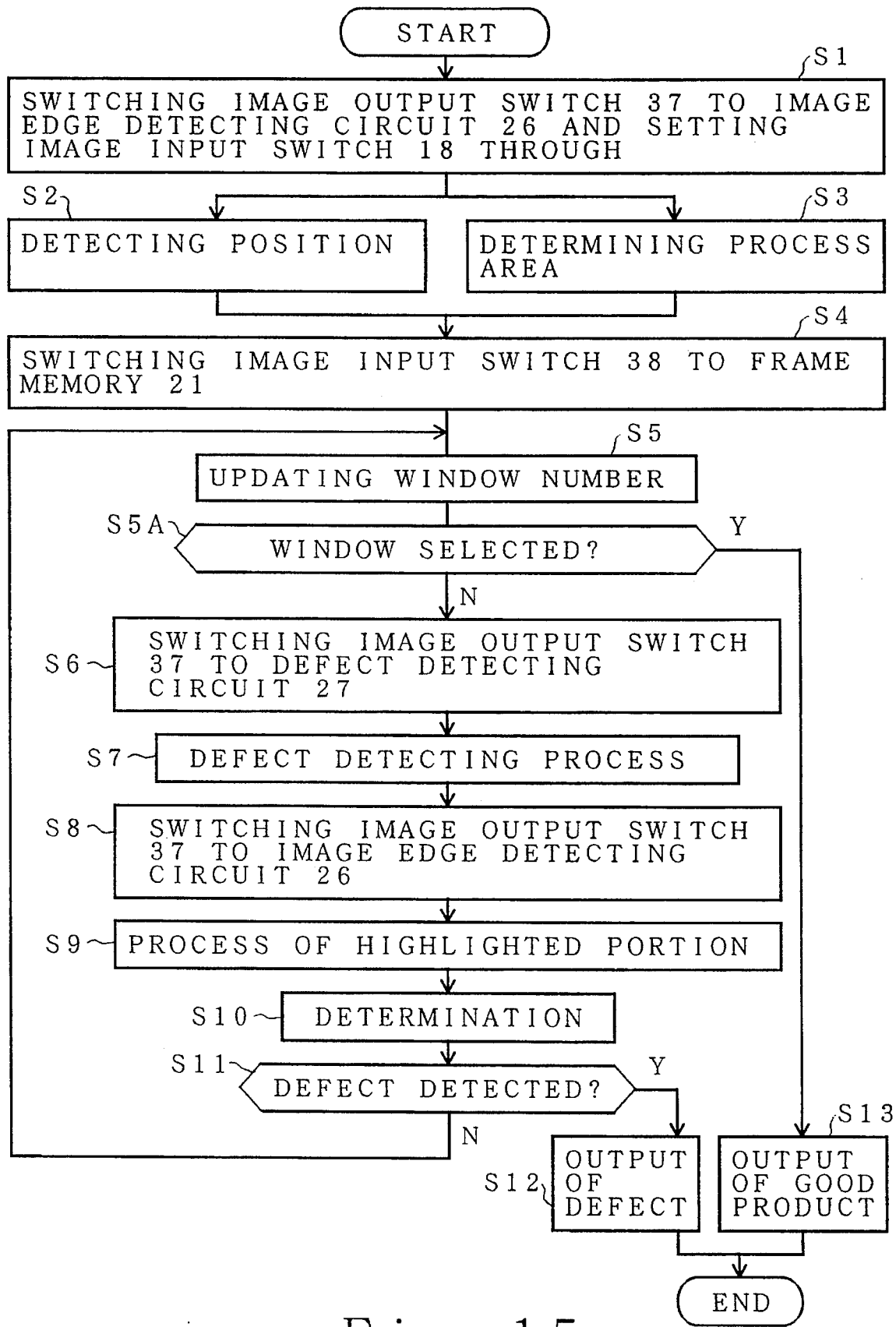
FIG. 15 is a flowchart for explaining the procedure of the operation associated with the configuration shown in FIG. 8.

FIG. 15 is a flowchart for explaining the procedure of the operation shown in FIG. 8. The operation is explained by referring to FIG. 15. Numbers S1–S13 indicate the step numbers shown in FIG. 15. First, the image output switch 37 is switched to the image edge detecting circuit 26. Simultaneously, the image input switch 38 is put through, that is, switched to directly input a multi-value image signal PO (S1). Thus, the difference in the position of a target image is detected (S2). Simultaneously, a process area is determined through the X projection circuit 29, the Y projection circuit 30, and the process area determining circuit 34 (S3).

That is, in the step S2, the position difference amounts Δx and Δy of a container image are obtained through the position difference amount determining circuit 33, and a value for correcting a horizontal position difference is sent to the image address generating circuit 23 so that a window can be generated at the right position. In the step S3, a container image is isolated from another if they are arranged adjacent to each other by the process area determining circuit 34 so that one scanning area does not contain adjacent container images.

Then, the image input switch 38 is switched to the frame memory 21 (S4), and the following acceptability determining process is performed based on the continuous tone image data 21a in the frame memory 21. First, a test window area of a can under test correspond to the area of the window WN1 including the opening highlighted portion 3 and mask other window areas WN2 and WN3 (S5). Next, the process in a step S6 is performed until the test is completed for all the windows (branch to N in a step S5A). In the step S6, the image output switch 37 is switched to the defect detecting circuit 27 to detect a defect through the defect detecting circuit 27 and the defect detection determining circuit 32 (S7). The defect detecting circuit 27 detects black or white spots by the differentiation method, etc. to count the number of defective picture elements. The defect detection determining circuit 32 compares the counted number of defective picture elements with a predetermined value to determine the acceptability and output the result to the final determining circuit 35 in the step described later.

Then, the image output switch 37 is switched to the image edge detecting circuit 26 to operate the image edge detecting circuit 26 again, represent highlighted portion in binary as described above so that coordinates or an area of an outer or inner circle can be calculated (S9), perform the circularity check and compare the results with the standard area value through the highlighted portion determining circuit 31 so that the acceptability can be determined, and output the determination result to the final determining circuit 35 in the step described later.

The final determining circuit 35 instructs the output circuit 36 to output a defect (S12) if either the highlighted portion determining circuit 31 or the defect detection determining circuit 32 determines a defect (S10 to S11, branch to Y). If the test container is determined to be a non-defective product in the step S11, control is returned to the step S5 again, the next test area is the window area WN2 containing the bottom highlighted portion 4, the other areas WN1 and WN3 are masked, and the following steps up to the step S12 are repeated. When the tests on all the windows are completed up to the window WN3 (in the step S5A, branch to Y), the output circuit 36 is instructed to output the non-defective product through the final determining circuit 35 (S13).

Figure 16:
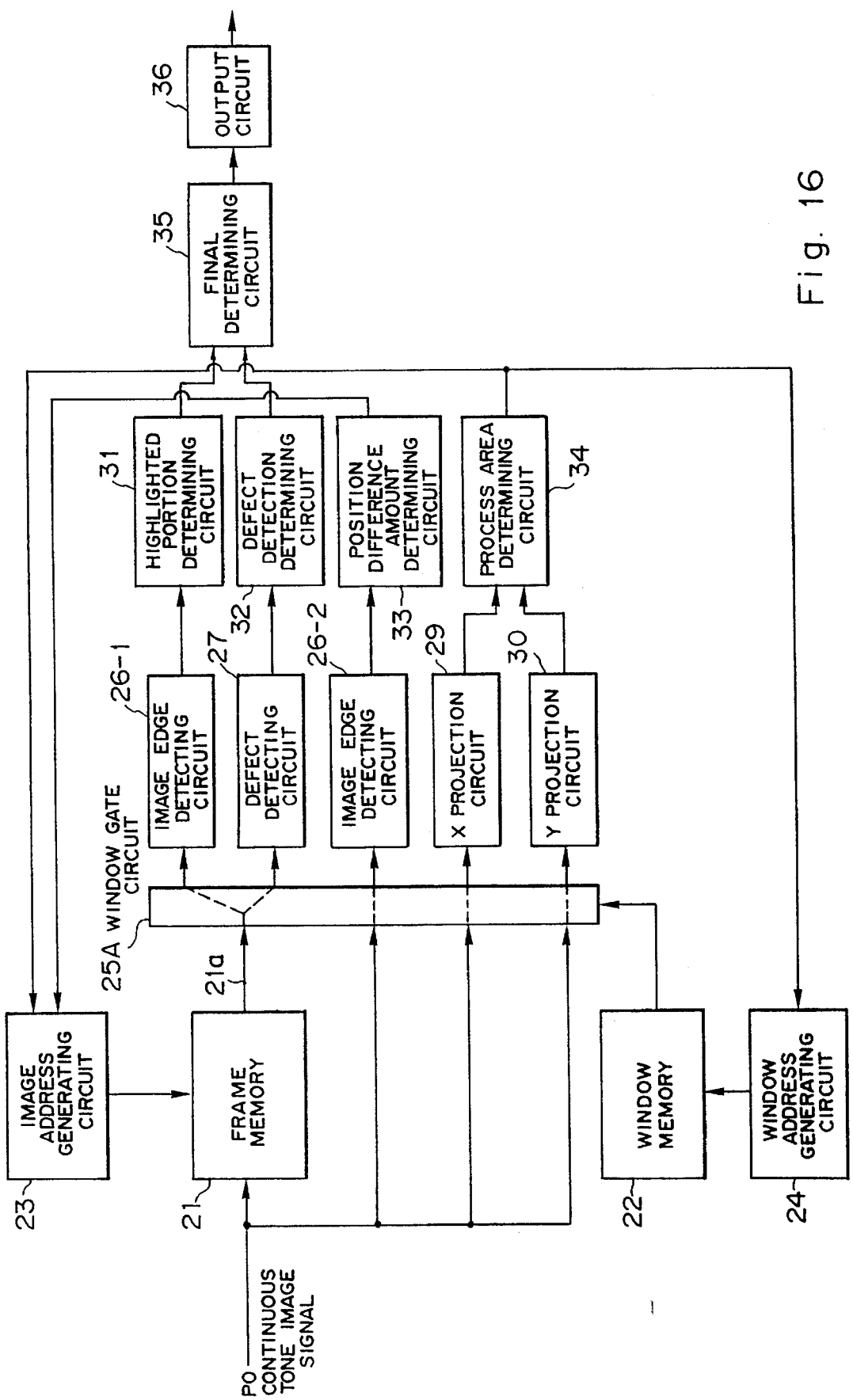
FIG. 16 is a block diagram of the hardware configuration of the second embodiment of the present invention.

FIG. 16 shows the block diagram of the hardware configuration of the second embodiment of the present invention in which the processes shown in FIG. 8 can be performed in a high speed. In FIG. 16, the image input switch 38 shown in FIG. 8 is omitted and the window circuit 25 is revised as a new window circuit 25A, two circuits 26-1 and 26-2 corresponding to the image edge detecting circuit 26 are provided where one image edge detecting circuit 26-2 directly receives a multi-value image signal PO (through the window gate circuit 5A) and provides the detection result for the position difference amount determining circuit 33. Furthermore, the image output switch 37 shown in FIG. 8 is omitted and the output image signal 21a from the frame memory is provided concurrently for the other image edge detecting circuit 26-1 and the defect detecting circuit 27 (through the window gate circuit 5A) to concurrently perform the processes by the highlighted portion determining circuit and the defect detecting circuit 31.

Figure 17:
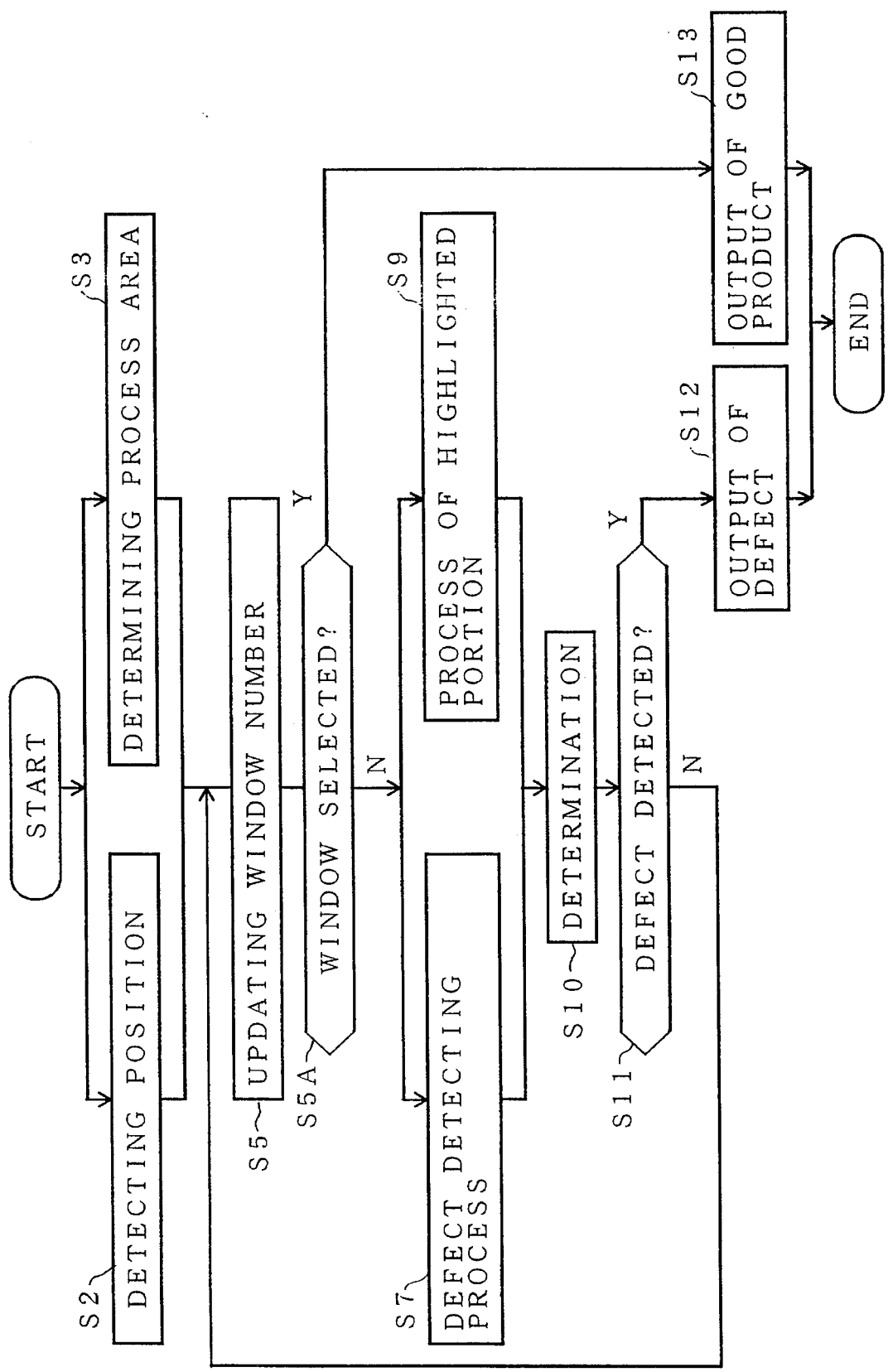
FIG. 17 is a flowchart for explaining the procedure of the operation associated with the configuration shown in FIG. 16.

FIG. 17 is a flowchart for explaining the procedure of the operation shown in FIG. 16, where the switching steps S1, S4, S6, and S8 of the switches 37 and 38 are omitted from the procedure shown in FIG. 15. Additionally, the defect detecting process in step S7 and the process of highlighted portions in step S9 are performed concurrently.

FIGS. 5A and 5B are explanatory views of a bottom highlighted portion of a container whose bottom is formed uniquely differently from that in FIGS. 1A and 1B. FIG. 5A is a plan view (image); and FIG. 5B is a cross-sectional view. In this embodiment, the bottom highlighted portion 4 is generated as 4-1 and 4-2. In this way, a bottom highlighted portion can sometimes be generated concentrically in more than one circle depending on the shape of the bottom part of a container. In this case, the bottom area is appropriately divided and the number of windows is increased correspondingly. The step S5A shown in FIGS. 15 and 17 shows a conditional branch involved therefor. Since a bottom portion is a comparatively small area to be scanned, it can be processed at a high speed even though the number of windows is increased to some extent.

Figure 18:
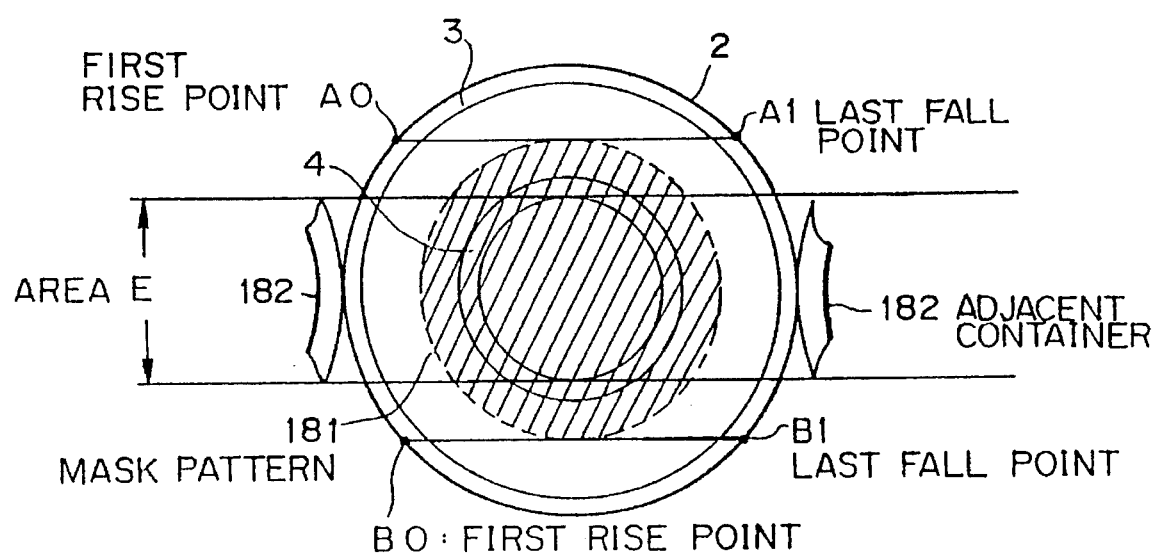
FIG. 18 shows a view for explaining how to detect the position of a target image in the first embodiment.

Additional explanation about an embodiment of a position detecting operation performed for a test image by the image edge detecting circuit 26 (FIG. 8) is given below by referring to FIGS. 34 through 37. FIG. 18 shows a view of an image of a highlighted portion for converting to the binary representation by the image edge detecting circuit 26. In FIG. 18, 181 is a mask pattern, and 181-2 is a container adjacent to a container under test 181 (182-1). That is, it is assumed that the bottom highlighted portion 4 has been masked by the mask pattern 181 through the window gate circuit 25 shown in FIG. 8. The coordinates indicated by the bold curves shown in FIG. 18 can be obtained when first rise points such as A0 and B0 and last fall points such as A1 and B1 are detected in the scanning direction in a binary image. However, incorrect values in the coordinates are obtained in the area E when any container is adjacent to the container under test. Therefore, the position of the container under test must be detected by the lines near the longest possible lines such as A0-A1 and B0-B1 in the horizontal scanning lines connecting the above described coordinates indicated by the bold curves out of the area E.

Figure 19:
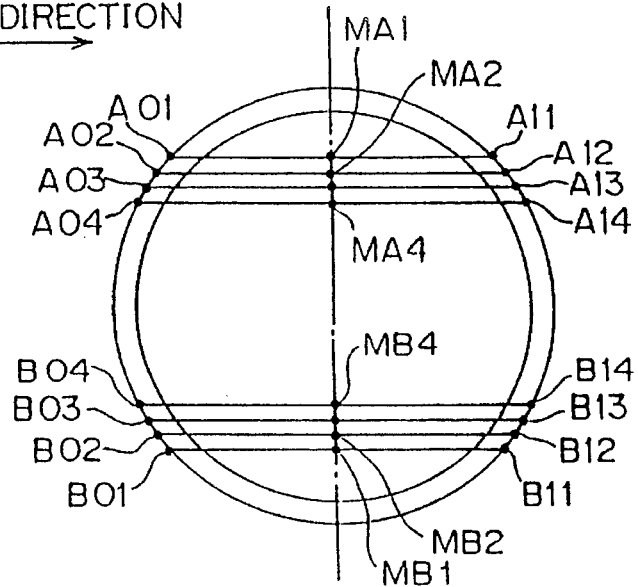
FIG. 19 shows the detailed drawing for supplementing FIG. 18.

FIG. 19 shows how the center positions (x coordinates) along horizontal scanning lines of a test container are obtained by calculating middle points MA (MA1 ... MA4) of lines A01-A11, ..., A04-A14 near the lines A0-A1 and B0-B1 out of the area E as described above by referring to FIG. 18, likewise by calculating the middle points MB (MB1 ... MB4) of lines B01-B11, ..., B04-B14, and by calculating the average value of these middle points MA1. .. MA4 and MB1 ... MB4.

The y coordinates can be obtained by calculating the average value of the coordinates of both ends (upper and lower limits) of the X-direction-projected pattern obtained by the X projection circuit 29 shown in FIG. 8.

Figure 20:
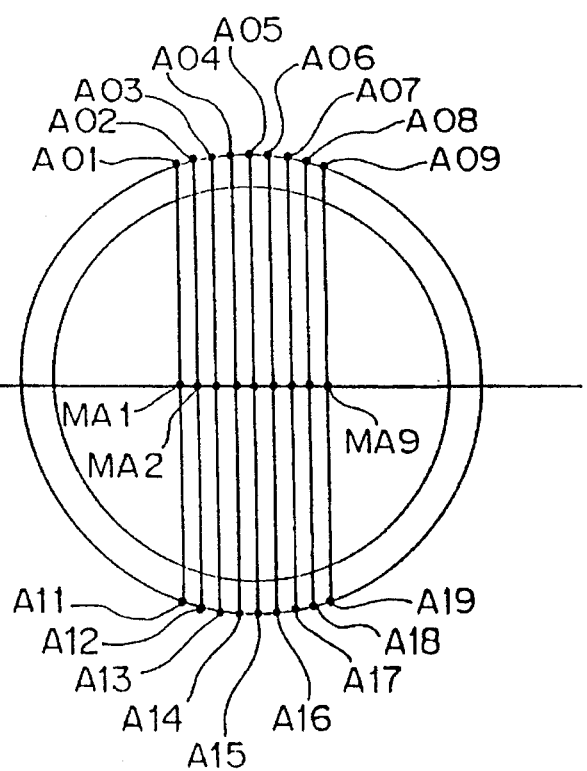
FIG. 20 shows how to detect a target image by another method.

FIG. 20 shows an example of a position detection by the method similar to the above described method in which an image is scanned vertically (in the Y direction) after the image is inputted to the frame memory 21a. That is, if containers are conveyed horizontally (in the X direction), they are not adjacent to one another vertically (in the Y direction). Therefore, there is no need to consider the area E shown in FIG. 18.

In FIG. 19, a multi-value continuous tone image signal PO can be used directly. However, in FIG. 20, an image signal 21a from the frame memory 21 must be used, thereby sometimes causing delay in processing time and incorrect position detection of a target image. However, the delay can be minimized by limiting the scanning operation shown in FIG. 20 to a local area.

Figure 21A:
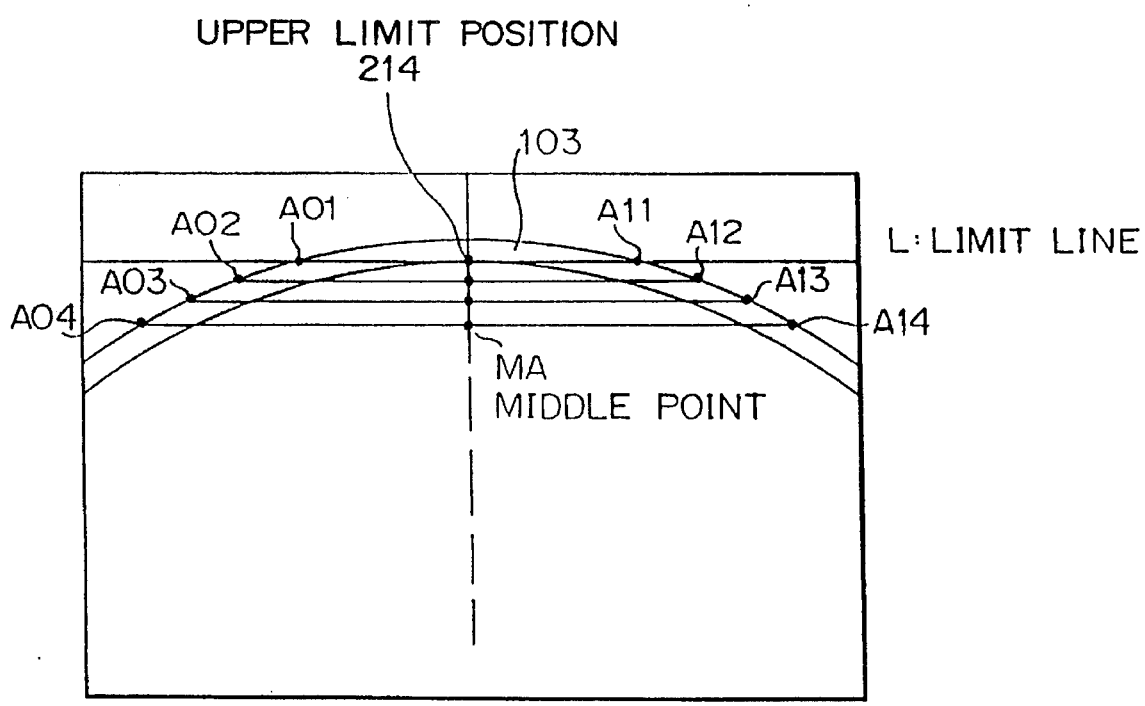
FIGS. 21A and 21B show views for explaining another example of detecting the position of the container.
Figure 21B:
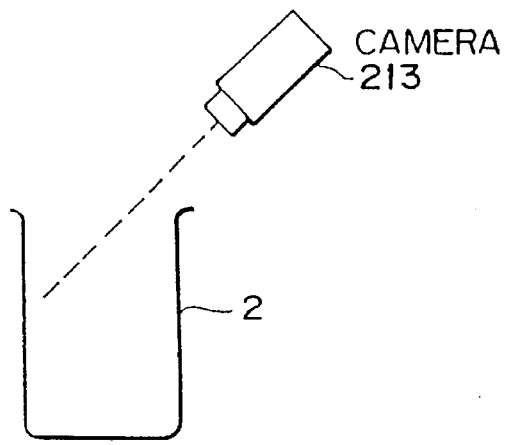

FIGS. 21A and 21B show views for explaining another example of detecting the position of a container by aiming at highlighted portions. In this example, the image is captured by a camera 213 in the oblique-above direction of the container 2 as shown in FIG. 23B. The opening highlighted portion 3 is observed as a binary image as shown in FIG. 21A. In this detected image, first rise points A01 ... A04 and last fall points A11 ... A14 are obtained in each horizontal scanning line. Then, an average value MA of the middle points of lines A01-A11, ..., and A04-A14 are calculated to specify the horizontal position of the test container under test. The vertical position of the test container can be specified by obtaining the limit line L at which the length of the horizontal scanning line falls below a predetermined value, thereby specifying the upper limit of the horizontal position of the container under test.

This position detecting method can be applied to the case where the upper limit of a container is specified as a predetermined position determination point.

Figure 22A:
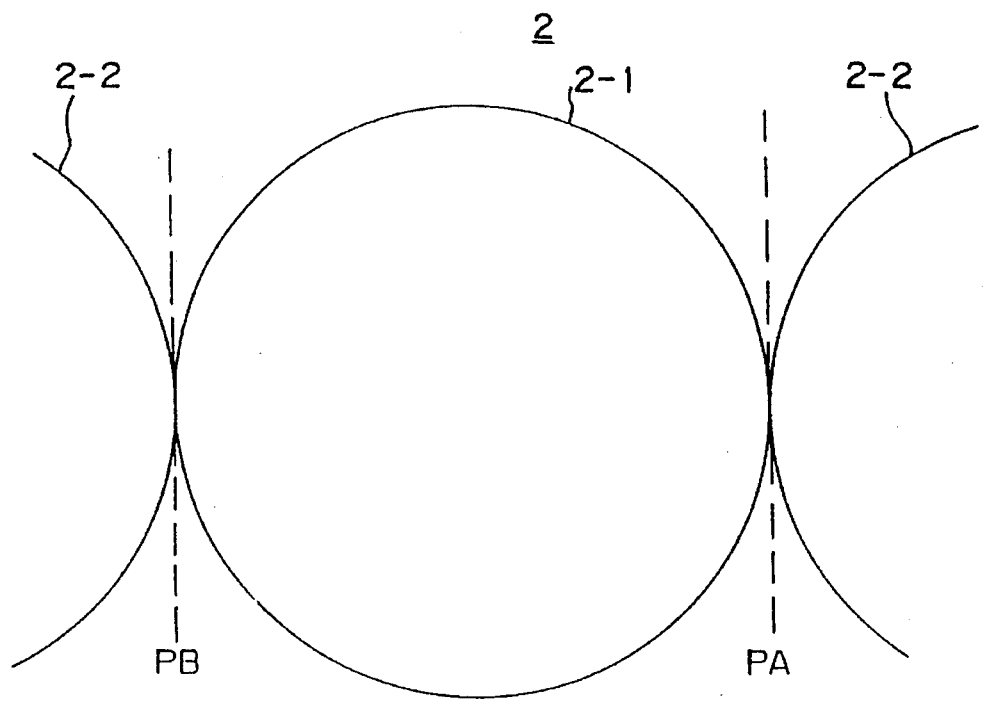
FIGS. 22A, 22B and 22C show method of detecting a container adjacent point.
Figure 22B:
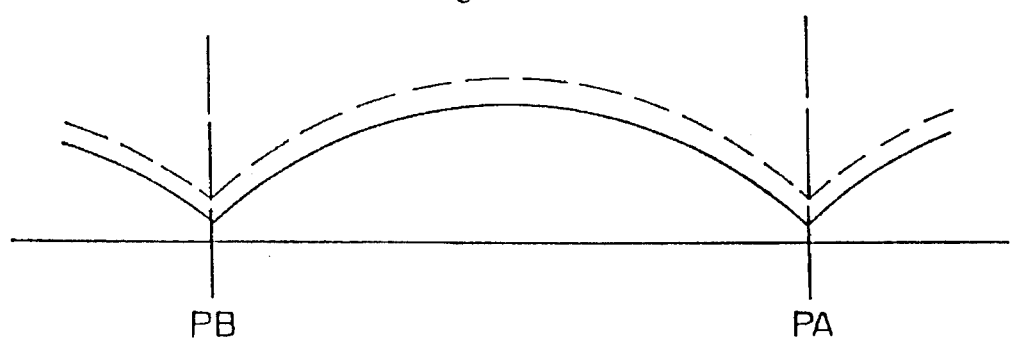
Figure 22C:
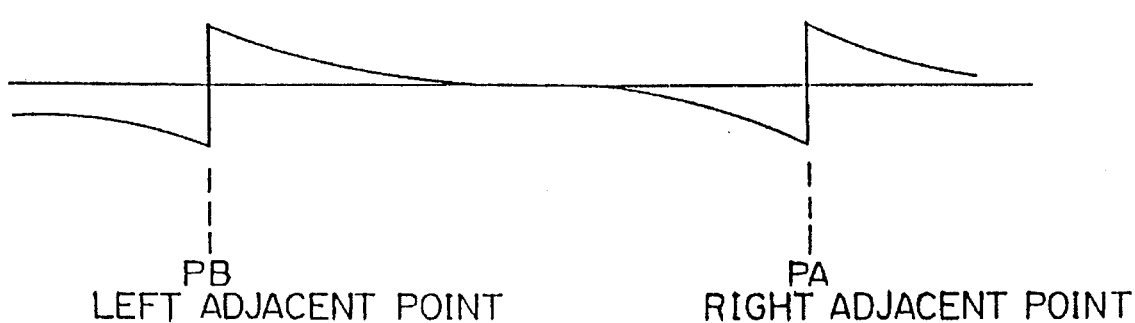

Additional explanation is given below, by referring to FIGS. 22 through 25, about an embodiment of a process area determining operation in the case where a test container is adjacent to other containers. The process area determining circuit 34 shown in FIG. 8 performs an arithmetic operation of determining a process area according to the information from the X projection circuit 29 and the Y projection circuit 30. FIGS. 22A, 22B and 22C show the conventional method of determining a process area. FIG. 22A shows a binary image converted to the binary representation of the whole container using a threshold, where 2-1 is a container under test; and 2—2 is a container adjacent to the container under test 2-1. In this case, the containers are horizontally adjacent to one another.

FIG. 22B shows the number of projected picture elements of the image shown in FIG. 22A calculated in the vertical direction. FIG. 22C shows the difference obtained by subtracting the projected amount (the number of projected picture elements). In a relatively simple pattern shown in FIGS. 22A, 22B and 22C, a right adjacent point PA and a left adjacent point PB can be detected by a change point shown in FIG. 22C, thereby isolating the adjacent containers.

Figure 23A:
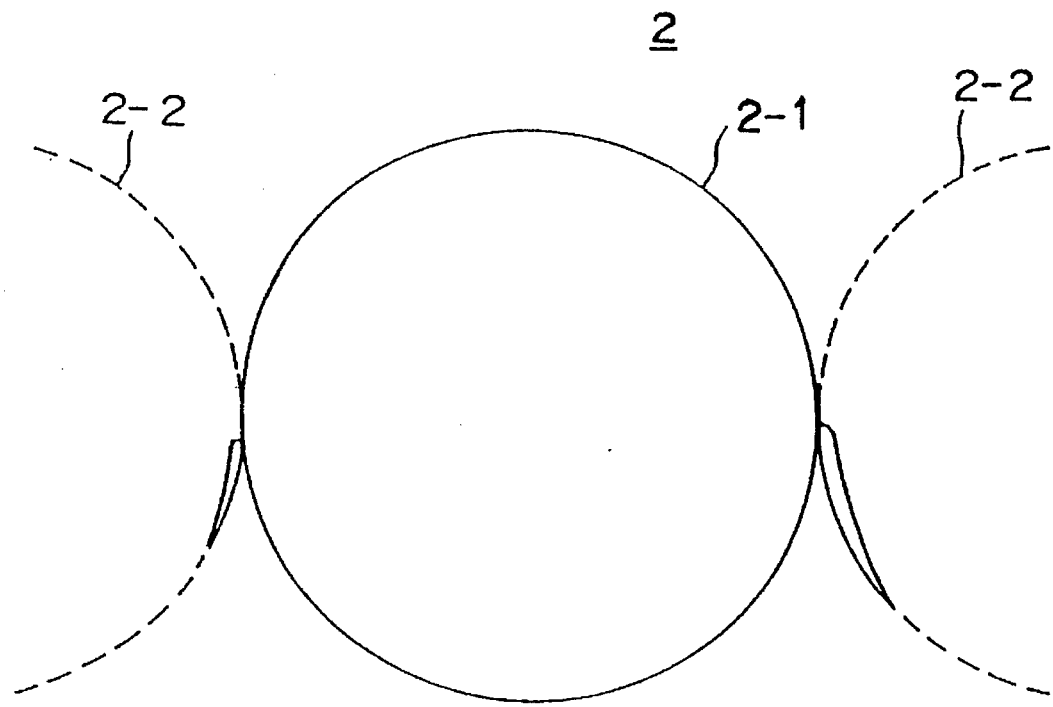
FIGS. 23A, 23B and 23C show an example where an adjacent point cannot be detected in the method shown in FIGS. 22A, 22B and 22C.
Figure 23B:
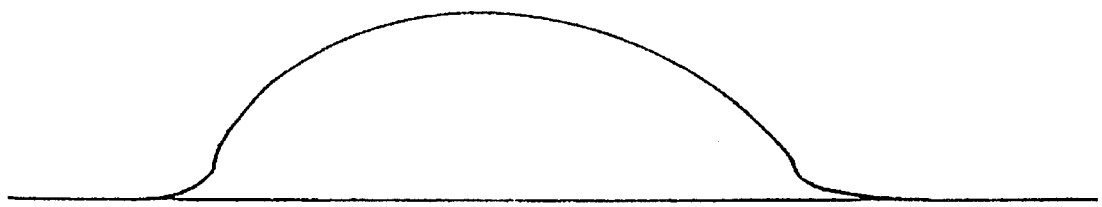
Figure 23C:

FIGS. 23A, 23B and 23C are a view for explaining the conventional method similar to one shown in FIGS. 22A, 22B and 22C in which adjacent points cannot be detected easily. That is, as shown by the actual test image in FIG. 23A, only a part of adjacent containers may be detected in binary. Therefore, the projection pattern comes out as shown in FIG. 23B, and the difference projection pattern is represented as shown in FIG. 23C, thereby preventing the containers from being isolated easily.

FIGS. 24A, 24B and 24C are a view for explaining the process area determining method according to the present invention for testing a container adjacent to other ones. That is, a threshold is determined to detect an opening highlighted portion 3 as a ring-shaped image by the Y projection circuit 30, a multi-value continuous tone image signal PO is converted to the binary representation to obtain a binary image shown in FIG. 24A, and then a projection pattern of this binary image shown in FIG. 24B can be obtained by calculating the projection in the Y direction vertical to the adjacent direction (horizontally, that is, the X direction).

Next, the process area determining circuit 34 calculates the difference in the projected amount (the number of projected picture elements) shown in FIG. 24B from the center to the opening of a container under test 102-1 as shown by the arrow 241 in FIG. 24C, and obtains a difference projection pattern as shown in FIG. 24C. Then, adjacent points can be obtained as follows.

That is, to obtain the right adjacent point PA, a detecting operation is performed from a side point P1 to the opening portion shown in FIG. 24C to obtain the point ΔPM at which the maximum difference projected amount is obtained (maximum difference projection point) within the range to the point PD at which the difference projection pattern graph first indicates a turn to decrease (difference decrease start point).

Figure 25:
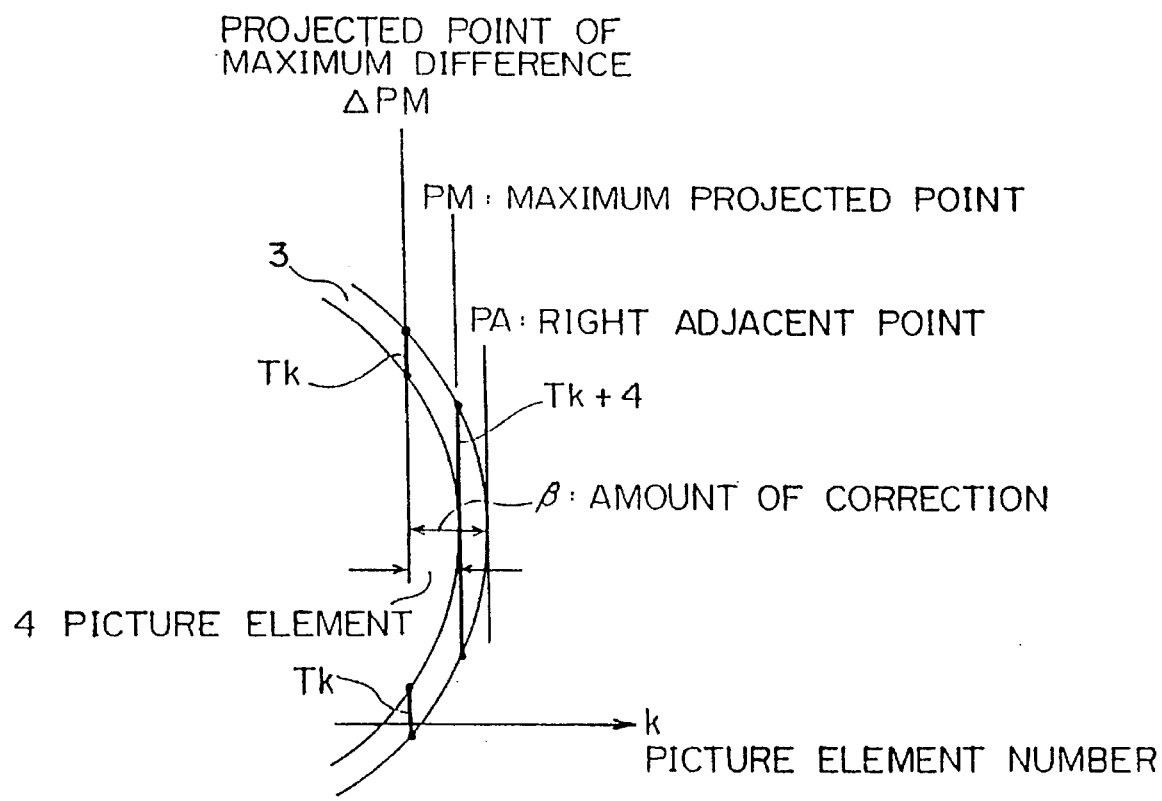
FIG. 25 is an enlarged view of FIG. 24A.

FIG. 25 is a view enlarged around the point ΔPM. In FIG. 25, PM marks the maximum projected amount in the opening highlighted portion 3 (referred to as the maximum projection point). ΔPM is a point near the maximum projection point PM and can be obtained as follows relative to the maximum projection point PM, that is, the picture element number k is sequentially assigned from the center of the test container 2 to the X direction. The number of projected picture elements is Tk at the position of the picture element number k. The difference between the Tk and the number of the projected picture elements $T_{k+4}$ at the point four picture elements apart to the right can be obtained as follows.

$$\Delta T_k = T_{k+4} - T_k$$

If the differences thus calculated generate a difference projection pattern, ΔPM indicating the maximum value of $\Delta T_k$ is determined to be the point four picture elements inside the maximum projection point PM.

In the present invention, the right adjacent point PA can be obtained by adding a predetermined correction value β to the maximum difference projection point ΔPM. According to the result, adjacent containers are isolated and the resultant coordinates determine a process area.

The maximum difference projection point ΔPM is obtained first because it can be detected as stable coordinates while the maximum projection point PM is subject to the influence of the fluctuation of the ring width of the opening highlighted portion 3 caused by the intensity of the illumination applied to the container under test.

Thus, the present invention can reduce the influence of adjacent containers by detecting an adjacent point from the center to the opening of a container under test by utilizing the opening highlighted portions 3.

Figure 26:
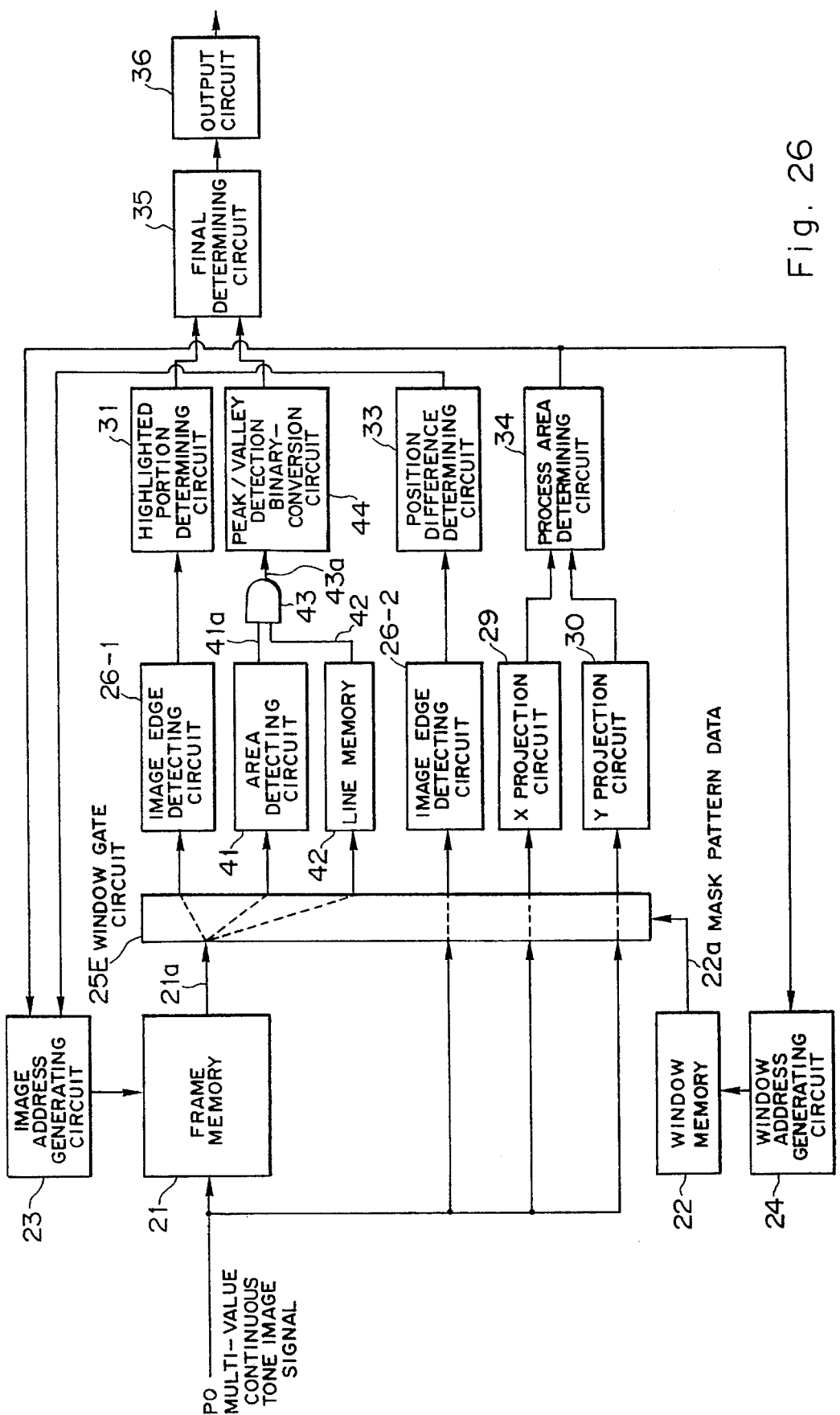
FIG. 26 is a block diagram for explaining the hardware configuration of the third embodiment of the present invention.

Another embodiment of the present invention is described below by referring to FIGS. 7A and 7B, and 26 through 32C. FIG. 26 is a block diagram of the hardware configuration as the third embodiment of the present invention. In FIG. 26, a multi-value (8 bits, for example) continuous tone image signal PO is obtained by AD-converting the video signal obtained by raster-scanning the surface of a TV camera not shown in FIG. 26. A frame memory 21 receives a multi-value continuous tone image signal PO to be stored as multi-value image data; an image address generating circuit 23 is provided for the frame memory; a window memory 22 stores a mask pattern for each window; an address circuit 24 is provided for the window memory; a window gate 25E masks with a mask pattern data 22a outputted from the window memory 22 a multi-value continuous tone image signal PC or an image signal 21a read from the frame memory 21, and passes only the image signal PO or the image signal 21a for the specified window area.

Image edge detecting circuits 26-1 and 26-2 detect the edge of an image, that is, the outer edge (the point in the outer circumference) and the inner edge (the point in the inner circumference) of a ring-shaped highlighted portion. In this case, an inputted image signal is converted to the binary representation using a predetermined threshold used for detecting the position of a target image or performing the circularity check. Then, the image edge detecting circuit 26-1 and 26-2 store the rise point and the fall point coordinates of the binary signals each indicating the edge of an image in their own memories. A circuit 31 performs the circularity check on the coordinates of the points in the outer and inner circumferences detected by the image edge detecting circuit 26-1.

A circuit 33 detects the difference between the center position of an actual target image detected by the image edge detecting circuit 26-2 by applying the latest multi-value continuous tone image signal PO and the central position of a predetermined window.

An area detecting circuit 41 receives a multi-valve continuous tone signal 21a through the frame memory 21 and the window gate circuit 25E, and outputs an area signal 41a as a signal for specifying an area to be scanned (that is, an area within the contour of a test container) for a defect on each of the horizontal scanning lines for the purpose of detecting a defective image.

A line memory 42 receives an image signal 21a for each of the horizontal scanning lines in synchronous with the area detecting circuit 41, and temporarily stores it.

A AND gate 43 ANDs an area signal 41a and a continuous tone image signal 42a outputted by the line memory 42 as an image signal for each of the horizontal scanning lines corresponding to an area signal 41a, and outputs a continuous tone image signal for an area to be searched for a defect (referred to as a test area continuous tone image signal).

A peak/valley detection binary-conversion circuit 44 is an important part of the present invention and detects from an image signal 43a a defective picture element including a defective peak/valley described by referring to FIGS. 7A and 7B.

An X projection circuit 29 obtains an X-direction projection pattern of a target image using a multi-value image signal PO which has passed through the window gate circuit 25E. Likewise, a Y projection circuit 30 obtains a Y-direction projection pattern of a target image. A process area determining circuit 34 determines using these output data from the projection circuits 29 and 30 the area of a test container image not adjacent to other container images.

A final determining circuit 35 receives a determination result from the peak/valley detection binary-conversion circuit 44 to make final determination; and an output circuit 36 outputs the acceptability according to a determination signal outputted by the final determining circuit 35.

In the present invention, the area detecting circuit 41 detects the contour of a container as a test area, and the area is searched for a defect according to the expressions (1), (2), (1A), and (2A) shown in FIGS. 7A and 7B.

Additional information about the multi-value continuous tone image signal PO is described below. That is, an analog video signal obtained by raster-scanning the image taken by a TV camera can be converted to a digital signal using an A/D converting circuit, etc. by a common method. Then, the multi-value continuous tone image signal PO is a digital signal converted by the A/D converting circuit, etc.

Figure 27A:
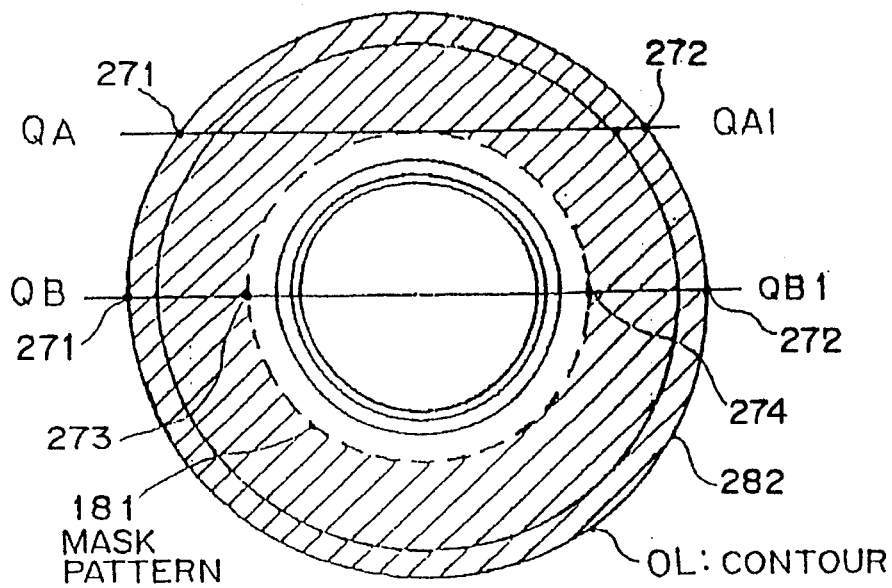
FIGS. 27A, 27B and 27C are views for explaining the operation of the area detecting circuit.
Figure 27B:
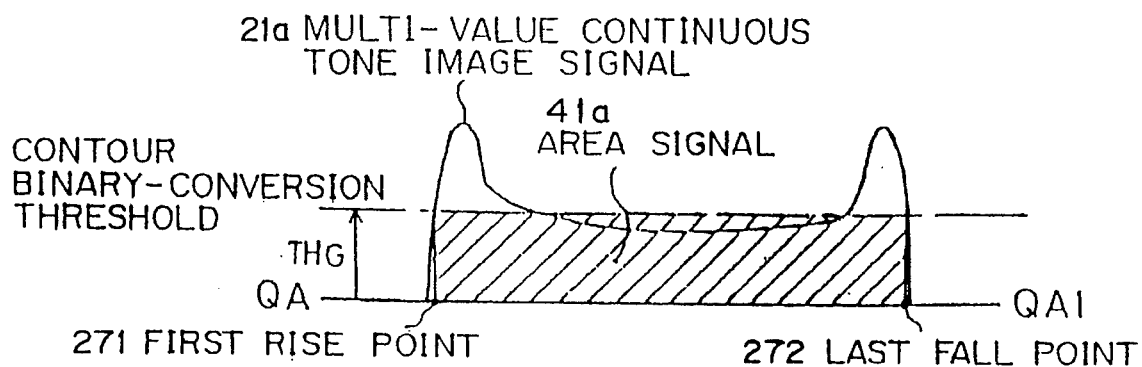
Figure 27C:
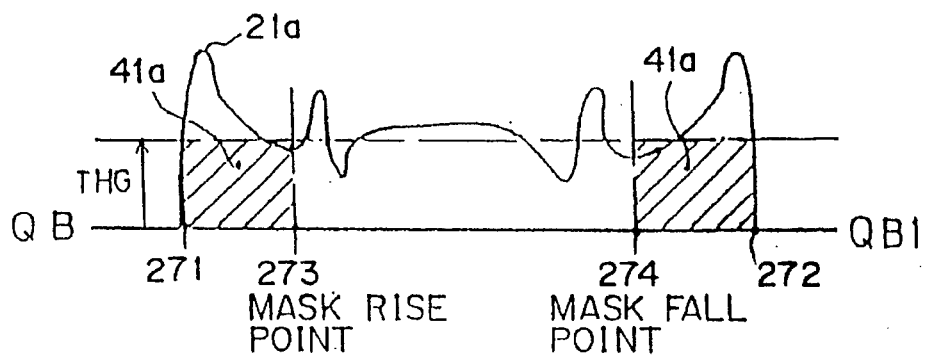

FIGS. 27A through 27C show the operation of the above described area detecting circuit 41, that is, the operation for detecting the test area (namely, the contour of a container). That is, FIG. 27A is a top view of the container 282, where OL shows the contour, the lines QA–QA1 and QB–QB1 show scanning lines (or section), and 181 is a mask pattern. FIG. 27B indicates the relationship between the intensity variations (continuous tone image signal) along the section QA–QA1 and the area to be tested. FIG. 27C shows the relationship between the intensity variations (continuous tone image signal) along the section QB–QB1 and the test area.

As described above, the area detecting circuit 41 receives a multi-value continuous tone image signal 21a from the frame memory 21 through the window gate circuit 25E, and converts it to a binary number using a threshold THG (referred to as a binary contour threshold for convenience) as shown in FIG. 27B. Then, the first rise point 271 and the last fall point 272 of the binary signal are detected, and the range between these points is defined as a process range.

A signal indicating the process range, that is, the signal indicating "1" for the diagonal-shaded portion shown in FIG. 27B is outputted as the area signal 41a. The area signal 41a and the continuous tone signal 42a for one scanning line temporarily stored in the line memory 42 corresponding to the area signal 41a are ANDed through the AND gate 43 to output the above described continuous tone signal 43a for the test area.

Alternatively, the area signal 41a can be obtained from the window signal obtained from the mask pattern data 22a from the window memory 22 (that is, a signal indicating the area excluding the mask pattern area), or as a combination of the area signal 41a and the window signal.

The area between the points 273 and 274 shown in FIG. 27C corresponds to the area of the mask pattern 181 shown in FIG. 27A, where 273 is a mask rise point, and 274 is a mask fall point. In this example, the mask pattern 181 masks the area in which the variation of the continuous tone image signal 21a of the container bottom is anticipated to be somewhat complicated.

In this case, the window signal can be obtained as "1" in the area excluding the area between the points 273 and 274 in the mask area. The signal obtained by combining the original area signal indicating "1" only between the first rise point 271 and the last fall point and the window signal, that is, the signal indicating "1" only in the diagonal-shaded portion between the points 271 and 273 and between the points 274 and 272 shown in FIG. 27C is the area signal 41a finally outputted from the area detecting circuit 41.

The test area indicated by diagonal shaped portion as shown in FIG. 27C can be assigned the optimum number $\alpha$ of picture elements and the threshold THD in expressions (1), (2), (1A), and (2A) shown in FIGS. 27A and 27B.

Thus, the optimum number $\alpha$ of picture elements according to the optical characteristics of the inner surface of a container and the threshold THD are selected by concentrically creating a number of the mask patterns 181 or the window patterns, thereby improving the efficiency in detection.

Figure 28:
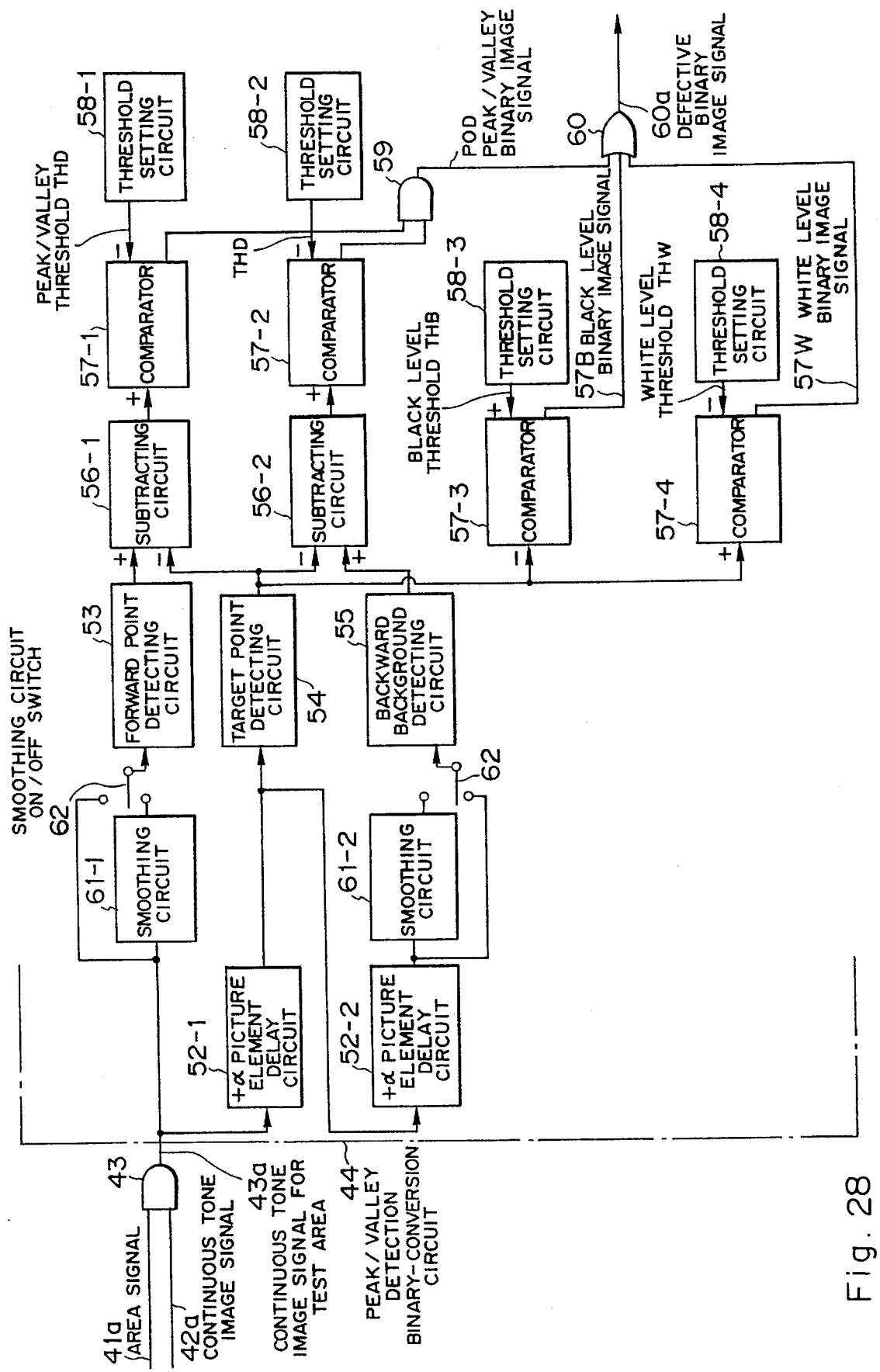
FIG. 28 is a block diagram for explaining in detail the configuration of the peak/valley detecting binary-conversion circuit in an embodiment of the present invention.

FIG. 28 is a block diagram of an embodiment of the detailed configuration of the peak/valley detection binary-conversion circuit 44 shown in FIG. 26. However, with this configuration, a valley (defect) is detected. In the case of a peak (defect) detection, the subtraction of subtraction circuits 56-1 and 56-2 is inverted, or an input image signal 43a applied to the peak/valley detection binary-conversion circuit 44 is inverted. In this case, the function of a comparator 57-3 (black level determination by a fixed binary conversion) and that of a comparator 57-4 (white level determination by a fixed binary conversion) are exchanged with each other.

Next, the function shown in FIG. 28 is explained below. FIG. 28 shows the execution of the principle shown in FIG. 26. In FIG. 28, +$\alpha$ picture element delay circuits 52-1 and 52-2 sequentially delay an input image signal 43a (that is, a test area continuous tone image signal outputted by the AND gate 43 shown in FIG. 26) by $\alpha$ picture elements in the scanning direction.

Smoothing circuits 61-1 and 61-2 smooth an image signal if necessary to reduce the influence of noises; and a smoothing circuit ON/OFF switch 62 switches the smoothing function.

The smoothing circuit 61-1 is provided corresponding to the forward background point detecting circuit 53, and likewise, the smoothing circuit 61-2 is provided corresponding to the backward background point detecting circuit 55. For the purpose of improving the sensitivity in detecting a defect in a target point (that is, improving the function of detecting a defective picture image by a small peak/valley or small intensity variations, namely, by a small threshold value), the smoothing circuit is not provided for a target point detecting circuit 54 described later.

A forward background detecting circuit 53 receives a test area continuous tone image signal 43a or a smoothed signal as an original input image signal for it to detect a forward background point. A target point detecting circuit 54 receives an output image signal of the +$\alpha$ picture element delay circuit 52-1 to detect a target point. A backward background detecting circuit 35 receives an image signal outputted by the +$\alpha$ picture element delay circuit 52-2 or a smoothed signal for it to detect a backward background point. Each of the detecting circuits 53, 54, and 55 simultaneously latches the picture element values PO(i+$\alpha$,j), PO(i,j), and PO(i-$\alpha$,j) described by referring to FIGS. 7A and 7B if the smoothing circuit 61-1 and 61-2 are omitted (that is, the smoothing circuit is short-circuited by the switch 62) when the delay circuits 52-1 and 52-2 are used.

When the smoothing circuits 61-1 and 61-2 are used, the above described picture element values PO(i+$\alpha$,j) and PO(i-$\alpha$,j) are replaced with the results of the following expressions (3) and (4) respectively.

$$PO(i+\alpha,j) = \{\sum_{k=0}^{n-1} PO(i+\alpha+k,j)\}/n \quad (3)$$

$$PO(i-\alpha,j)=\{_{k-0}\Sigma^{n-1}PO(i-\alpha-k,j)\}/n \qquad (4)$$

That is, the smoothing circuit 61-1 replaces the picture element value of the forward background point with an average value of n forward picture element values including the picture element value PO(i+α,j) of the forward background point and those of the points beyond it. Likewise, the smoothing circuit 61-2 replaces the picture element value of the backward background point with an average value of n backward picture element values including the picture element value PO(i-α,j) of the backward background point and those of the points beyond it.

The average values are not calculated with the background point set as a median to prevent the picture element value PO(i,j) of a target point from being involved in calculating the average values.

An average value obtained by expression (3) or (4) can be replaced with a median in n picture element values (that is, the value at the middle point when n values are arranged in order).

Each piece of the above described image data latched by the detecting circuits 53, 54, and 55 shown in FIG. 28 are applied to the subtracting circuits 56-1 and 56-2 and the difference is calculated according to the contents of expressions (1) and (2) shown in FIGS. 7A and 7B. The difference is compared by comparators 57-1 and 57-2 with a peak/valley value THD each being predetermined by threshold setting circuits 58-1 and 58-2. Thus, a peak/valley binary image signal POD shown in FIGS. 7A and 7B (a defective bottom in this case) can be obtained as an output from the AND gate 59 for ANDing the output signals from the comparators 57-1 and 57-2.

The comparators 57-3 and 57-4 detect a defective picture element in a relatively large area. The comparator 57-3 receives image data of a target picture element outputted by the target point detecting circuit 54 which does not receive a smoothed image signal. Then, it compares the received data with a black level threshold THB determined by the threshold setting circuit 58-3, and detects to output a black level binary image signal 57B indicating a black level defective picture element.

Likewise, the comparator 57-4 receives data of a target picture element, compares it with a white level threshold THW determined by a threshold setting circuit 58-4, and detects and outputs a white level binary image signal 57W indicating a white level defective picture element.

An OR gate 60 ORs the signals thus detected as defective picture element detection signals including a peak/valley binary image signal POD, a black level binary image signal 57B, and a white level binary image signal 57W, and outputs a defective binary image signal 60a.

A black level defective picture element detector (the comparator 57-3, etc.) and a white level defective picture element detector (the comparator 57-4, etc.) operate concurrently with the peak/valley detector/binary-converter (an AND gate 59, etc.). These units separately test an image, and the results are finally put together and outputted as final determination.

Next, an image scanning method is explained below. FIG. 7A shows the continuous tone of an image at a section Q–Q1. In expressions (1), (2), (1A), and (2A), α means the number of picture elements, and is a parameter indicating the frequency of an image signal at a defective portion (that is, the width of a peak or a valley). However, as shown in FIG. 7A, continuous tone image signals for the inner surface of a non-defective container complexly comprise various frequency components. Therefore, the inner surface of a container must be divided if necessary and each of them must be assigned an optimum parameter.

However, the intensity variations in background picture elements can be simplified by appropriately determining the scanning direction of the image, thereby improving the detection precision.

Figure 29A:
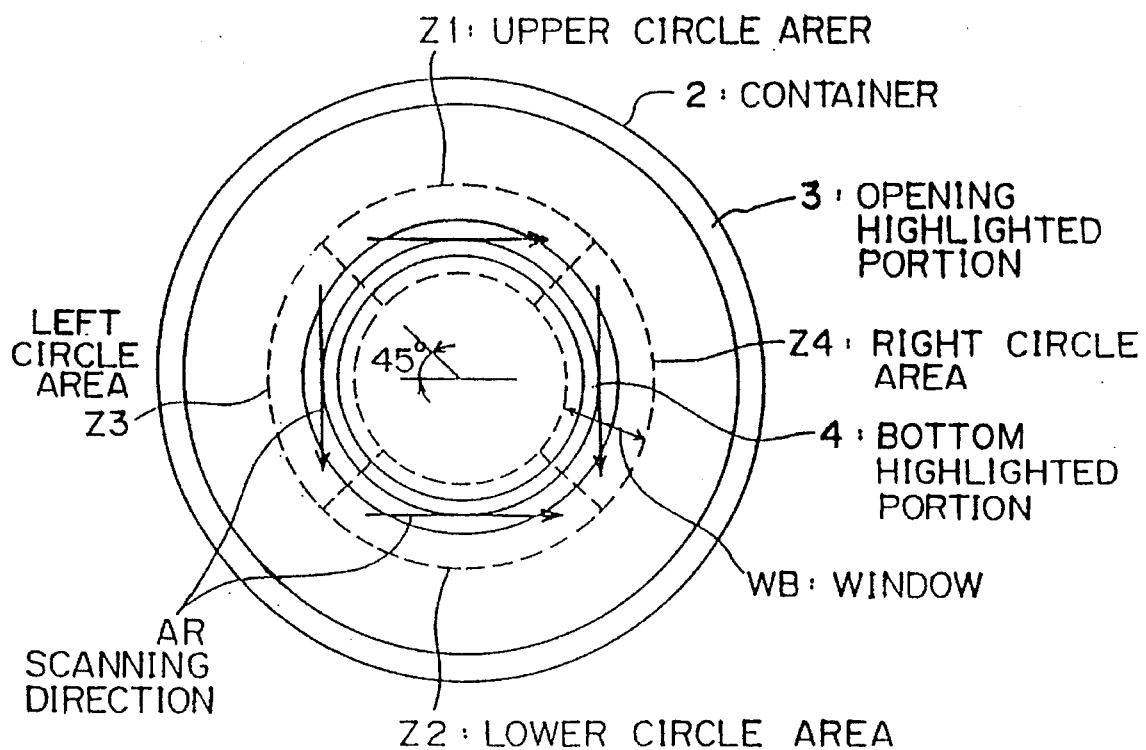
FIGS. 29A, 29B and 29C show the first embodiment of the screen scanning method of the present invention.
Figure 29B:
Figure 29C:
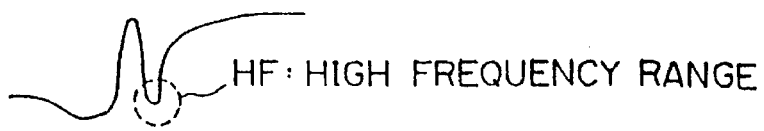

FIGS. 29A, 29B and 29C are views for explaining an embodiment of an image scanning method, where a window WB is divided into the following four areas each being selected as a target area to be searched for a defect; Z1, Z2, Z3, and Z4 are respectively upper circle area, lower circle area, left circle area, and right circle area. That is, in FIG. 29A, the bottom highlighted portion 4 having complicated intensity variations in the container 2 is selected through the window WB and a peak is detected and binary-converted. If the intensity variations are checked horizontally, for example, in the left circle area Z3 of the window WB, the intensity variations occur at a high frequency in portions such as "HF" shown in FIG. 29C, thereby affecting the detection sensitivity. However, if the left circle area Z3 of FIG. 29A is scanned in the direction indicated by the arrow AR, intensity variations can be obtained at a low frequency as the background as shown in FIG. 29B, while the defective portions are detected at a sufficiently high frequency, thereby improving the detective precision.

Figure 30:
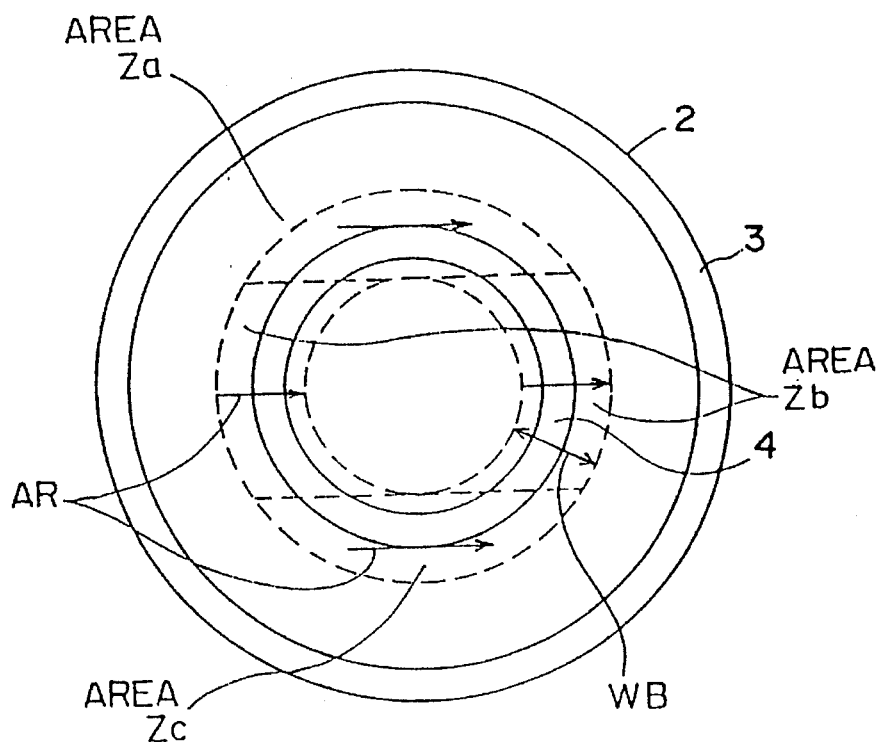
FIG. 30 shows the second embodiment of the screen scanning method of the present invention.

FIG. 30 is a view for explaining an embodiment of a simple picture scanning method. In FIG. 30, an image is scanned horizontally as indicated by the arrow AR, and the window WB is divided into three areas Za, Zb, and Zc. In this case, a threshold for detecting a peak/valley in the areas Za and Zc and a threshold for detecting a peak/valley in the area Zb are determined separately to perform an optimum detection according to the frequency of the background intensity.

In this case, the defect detection sensitivity is low in the area Zb. However, the detection sensitivity in the areas Za and Zc can be enhanced.

Figure 31:
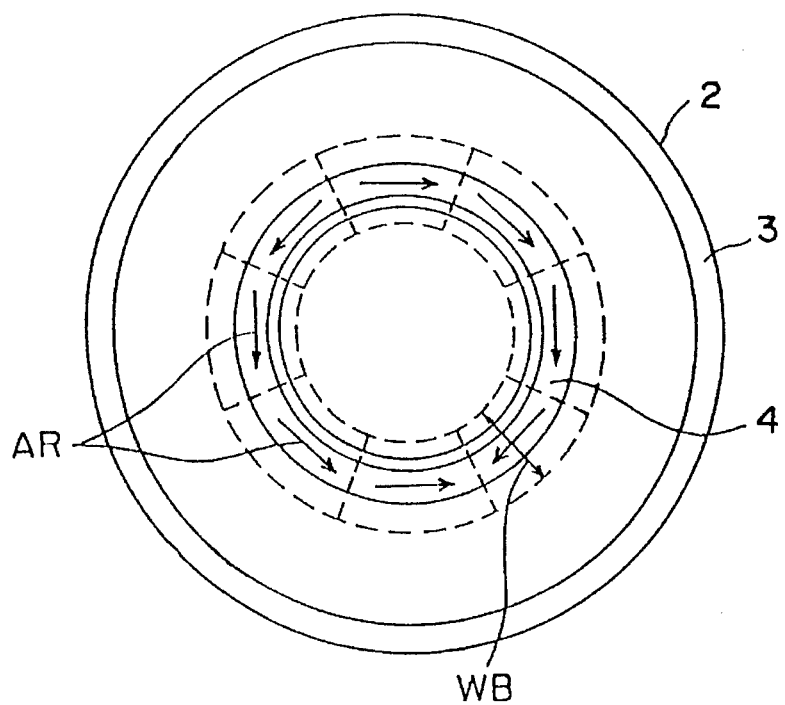
FIG. 31 shows the third embodiment of the screen scanning method of the present invention.

FIG. 31 shows a variation of the embodiment shown in FIG. 29A. In FIG. 29A, the scanning area is radially and equally divided into four fan-shaped areas. By contrast, in FIG. 31, the area is equally divided into eight fan-shaped areas, and an optimum scanning direction AR is assigned respectively, thereby improving the detection sensitivity much more than the case in FIG. 29A.

Figure 32A:
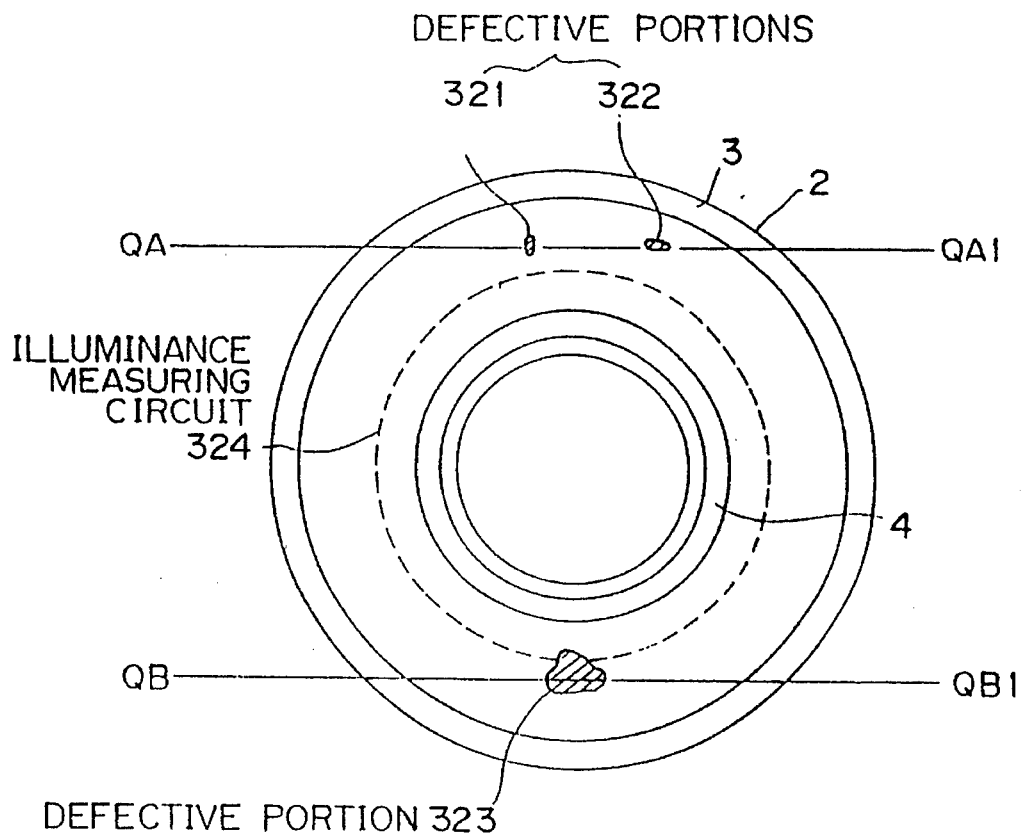
FIGS. 32A, 32B and 32C show the relationship between the defect detecting method of the present invention and the shape of a defective portion.
Figure 32B:
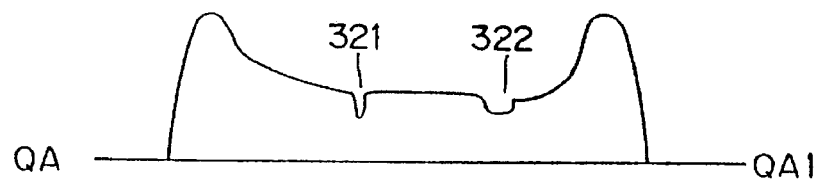
Figure 32C:
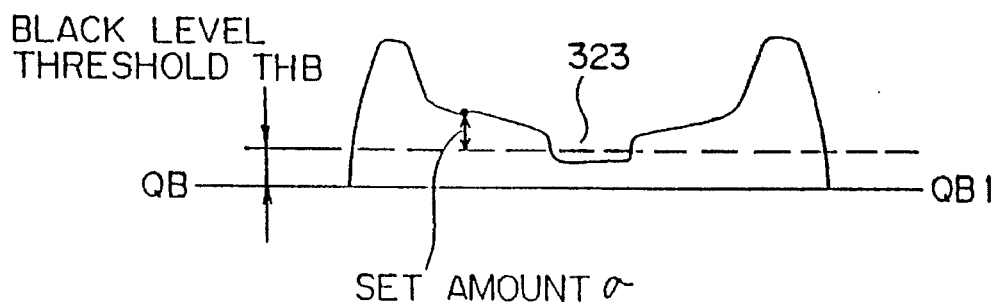

FIGS. 32A, 32B and 32C are views for explaining the relationship between a defect detecting method based on the present invention and the shape of a defective portion. In FIG. 32A, defective portions 321–323 is detected in the image of the container 2. FIG. 32B shows the intensity variations in the scanning line QA–QA1 shown in FIG. 32A. Defective oval portions 321 and 322 show different intensity frequencies depending on the direction of their longer diameter. Therefore, the defect detection sensitivity can be improved by picking up the amount corresponding to the number α of picture elements in expressions (1) and (2) several times and repeating the check.

FIG. 32C shows the intensity variations in the scanning line QB–QB1 shown in FIG. 32A. A defective portion 323 in this section is relatively large, and the variation in the continuous image signal is represented at a low frequency but sufficient to detect a black spot in contrast with its background. Since the defective portion 323 must be detected at a low frequency, it cannot be successfully detected unless the number α of the above described picture elements is unpractically large enough in the valley-detection and binary-conversion process. In such a case, using the fixed binary conversion method shown in FIG. 28, a defective portion 323 is isolated and detected as a black level as shown in FIG. 32C by setting a black level threshold THB by the threshold setting circuit 58-3 shown in FIG. 28, thereby supplementing the detective sensitivity in the valley-detection and binary-conversion process.

A black-level threshold THB can be determined by, for example, obtaining an average value of picture element intensity data of a circumference (an illuminance measurement circle) such as a circumference 324 shown in FIG. 32A, and subtracting a predetermined amount a from the average value.

The present invention performs a circularity check on the highlighted portions of the inner surface of a container. As a result, not only the deformation of a container or an abnormal concave in it, but the dust attached to a highlighted portion thereof can be detected with a high detective precision. Accordingly, a large window area can be scanned at a time (that is, the number of windows can be reduced) by parallelly performing the circularity check and the black/white spot test by the conventional defect test method, thereby speeding up the whole process.

The present invention performs a circularity check on a highlighted portion of the inner surface of a container after specifying the position of the container by obtaining the coordinates of the middle point between the first rise point and the last fall point in the scanning line of the binary image of the opening highlighted portion of a container. As a result, not only the deformation of a container (can) or an abnormal concave therein, but the dust attached to a highlighted portion thereof can be detected with a high detective precision. Accordingly, a large window area can be scanned at a time (that is, the number of windows can be reduced) by parallelly performing the circularity test and the black/white spot test by the conventional defect test method, thereby speeding up the whole process.

The present invention specifies the position of the container by obtaining the coordinates of the middle point between the first rise point and the last fall point in the scanning line of the binary image of the opening highlighted portion of a container.

Then, it performs a circularity check on a highlighted portion of an inner surface of a container after obtaining the projected amount of a binary image of the opening highlighted portion (the projection being made in the direction perpendicular to the container adjacent direction), searching for the difference in the projected amount, from the inner side to the outer side of a container detecting adjacent points on a predetermined condition, and isolating a target area from the area containing adjacent containers. As a result, not only the deformation of a container or an abnormal concave therein, but also the dust attached to a highlighted portion thereof can be detected with a high detective precision. Accordingly, a large window area can be scanned at a time (that is, the number of windows can be reduced) by parallelly performing the circularity check and the black/white spot test by the conventional defect test method, thereby speeding up the whole process.

The cylindrical container inner surface tester illuminates from above in the axis direction of a container by a ring-shaped illuminator 1 the inner surface of an axis-symmetrical cylindrical container 2. A TV camera captures the illuminated area of the cylindrical container 2 from above in the axis direction. Then, the captured is analyzed to determine a black or white spot inside the cylindrical container 2.

The cylindrical container inner surface tester comprises a defective peak/valley determiner (for example, an antecedent of an AND gate in a peak/valley detection binary-conversion circuit 44), an image test area divider, and a value changer.

The defective peak/valley determiner determines that a target picture element is defective if two differences obtained by subtracting the value PO(i,j) of a target picture element in the same picture element scanning line for a continuous tone image signal 43a which is obtained by scanning the above described captured image from the values PO(i+α,j) and PO(i-α,j) of two background picture elements (hereinafter referred to as a forward background picture element and a backward background picture element respectively) by a predetermined number of picture elements (hereinafter referred to as α picture elements) positioned backward or forward of the target picture element indicate the same polarity, if an absolute value of one of the above described two differences is larger than a predetermined first threshold (THD, for example) corresponding to the polarity, and if the other absolute value is larger than a predetermined second threshold (THD, for example).

The divider divides (into Z1–Z4, Za–Zc, etc.) the test area of a target image of the defective peak/valley determiner according to the optical features of a cylindrical container inner surface illuminated by the above described illuminator.

The value changer changes at least one value among the number of the above described α picture elements, the first threshold, and the second threshold.

The cylindrical container inner surface tester further comprises a unit for repeating the process performed by the defective peak/valley determiner by changing the number of a picture elements for one of the above described test areas.

The cylindrical container inner surface tester further comprises a black level defect determiner (a comparator 57-3, etc.) for determining a defective picture element whose continuous tone image signal 43a has a value smaller than a black level threshold THB, a third threshold predetermined for each test area.

The cylindrical container inner surface tester further comprises a white level defect determiner (a comparator 57-4, etc.) for determining a defective picture element whose continuous tone image signal 43a has a value larger than a white level threshold THW, a fourth threshold predetermined for each test area.

The cylindrical container inner surface tester further comprises a unit for obtaining a complement of 1 or 2 for the continuous tone image signal 43a to generate an inverted continuous tone image signal, converting the signal to the continuous tone image signal 43a, and providing it for the defective peak/valley determiner, thereby detecting a picture element having a defective peak/valley without inverting the above described polarity.

The cylindrical container inner surface tester further comprises a unit for obtaining a complement of 1 or 2 for the continuous tone image signal 43a to generate an inverted continuous tone image signal, converting the signal to the continuous tone image signal 43a, and providing it for the black level defect determiner, thereby detecting a picture element having a white level defect through the black level defect determiner.

The cylindrical container inner surface tester further comprises a unit for selecting for each test area the direction AR which allows the lowest possible frequency in the variation of a continuous tone image signal among a plurality of predetermined image scanning directions such as horizontal, vertical and oblique directions.

The cylindrical container inner surface tester further comprises a smoothing circuit 61-1 for outputting as the value of the above described forward background picture element an average value of the values of picture elements in a section comprising a first predetermined number (n, for example) of picture elements containing the above described forward background picture element in the above described scanning line, and a smoothing circuit 61-2 for outputting as the value of the above described backward background picture element an average value of the values of picture elements in a section comprising a second predetermined number (n, for example) of picture elements containing the above-described forward background picture element in the above described scanning line.

Since the cylindrical container inner surface tester comprises the above-described two units which output a median of the values of picture elements in a corresponding section instead of the above described average value, it can correctly detect a defect even though the uneven illuminance is caused by highlighted portions illuminated by an illuminator inside a cylindrical container.

Figure 33:
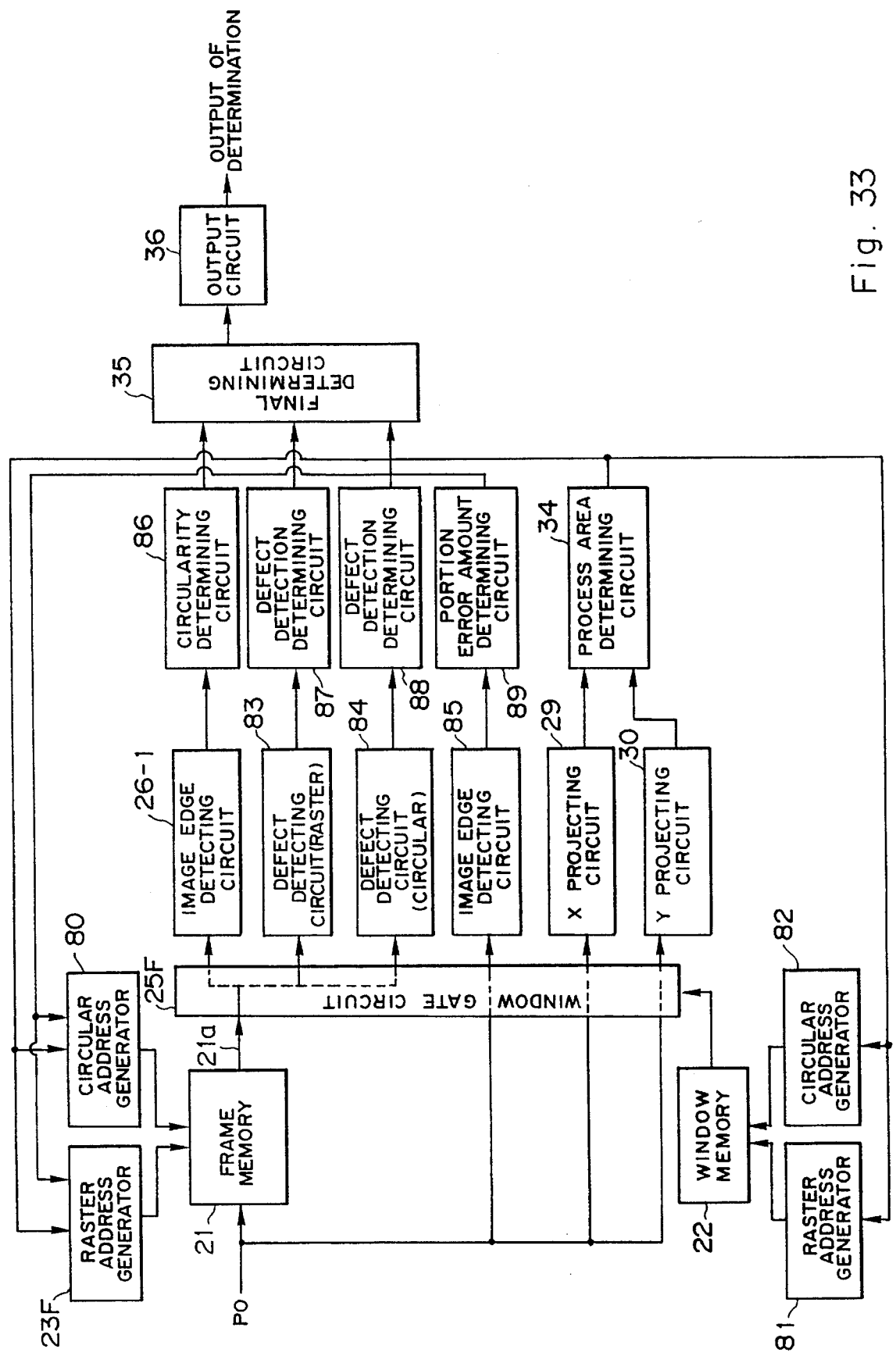
FIG. 33 is a block diagram of the hardware configuration of fourth embodiment of the present invention.

Next, FIG. 33 is the block diagram of the hardware configuration of the fourth embodiment of the present invention. In FIG. 33, a continuous tone image signal PO consisting of 8 bits, for example, is obtained by A/D converting a video signal generated by raster-scanning the screen of a TV camera (not shown in FIG. 33); a frame memory 21 receives the multi-valve continuous tone image signal PO and stores it as multi-value screen data; a raster address generator 23F generates a raster address for the frame memory; a circular address generator 80 generates an address for the frame memory 21 to circularly scan an image at; a window memory 22 stores a ring mask pattern for each window as shown in FIG. 2B; a raster address generator 81 generates a raster address for the window memory 22 in the same way as the generator 23F; likewise, a circular address generator 82 generates an address for the window memory 22 to circularly scan an image at. With this configuration, the generation of raster addresses and circular addresses can be switched by switching from the generators 23F and 81 to 80 and 82 respectively or vice versa.

A window gate circuit 25F masks a multi-value continuous tone signal PO or an image signal 21a read from the frame memory 21 with the mask pattern data from the window memory 22, and passes an image signal PO or an image signal 21a read from the frame memory 21 in the specified window area only.

An image edge detecting circuit 26-1 has a function of detecting the edge of an image, that is, the outermost points (the points in the outer circumference) and the innermost points (the points in the inner circumference) of the highlighted ring portion. The inputted image signal is converted to a binary representation according to a predetermined threshold used for detecting the position of a target image and checking the circularity, and the coordinates of the rise point and the fall point of the binary signal indicating the image edge are stored in the memory of the image edge detecting circuit. A circuit 86 checks the circularity of a test object according to the coordinates of the points on the outer or the inner circumference detected by the image edge detecting circuit 26-1.

A defect detecting circuit 83 receives through the window gate circuit 25F, the image signal 21a read from the frame memory 21 by raster-scanning the image in the frame memory 21, and detects picture elements indicating black spots, etc. A defect detection determining circuit 87 sums up the detected picture elements indicating a defect and determines whether a defect exists.

A defect detecting circuit 84 receives through the window gate circuit 25F, the image signal 21a read from the frame memory 21 by circularly scanning the image in the frame memory 21, and detects a picture element indicating a defective concave. A defect detection determining circuit 88 sums up the picture elements indicating a defect and determines whether a defect exists. A circuit 35-1 receives the determination results from the circularity determining circuit 86 and the defect detection determining circuits 87 and 88, and obtains the overall determination, and an output circuit 20 outputs a positive or negative defect determination result according to the output determination signal from the overall determination circuit 35.

Next, an X projecting circuit 9 obtains an X-direction projecting pattern for a target image using the latest multi-value signal PO passing through the window gate circuit 25F. Likewise, a Y projecting circuit obtains a Y-direction projecting pattern for a target image. A circuit 34 obtains the area of the test container image not adjacent to other container images according to the data outputted by the two projecting circuits 29 and 30.

That is, when a cylindrical container under test passes through a predetermined point, a static image of the container under test can be captured from above using a strobe light or an exposure controlled by a shutter. During the capture operation, the image is transmitted to the X projecting circuit 29 and the Y projecting circuit 30 so as to extract the characteristics of the projected pattern. When a fixed binary image is projected, the projecting circuits 29 and 30 function as converting to the binary representation.

Figure 34:
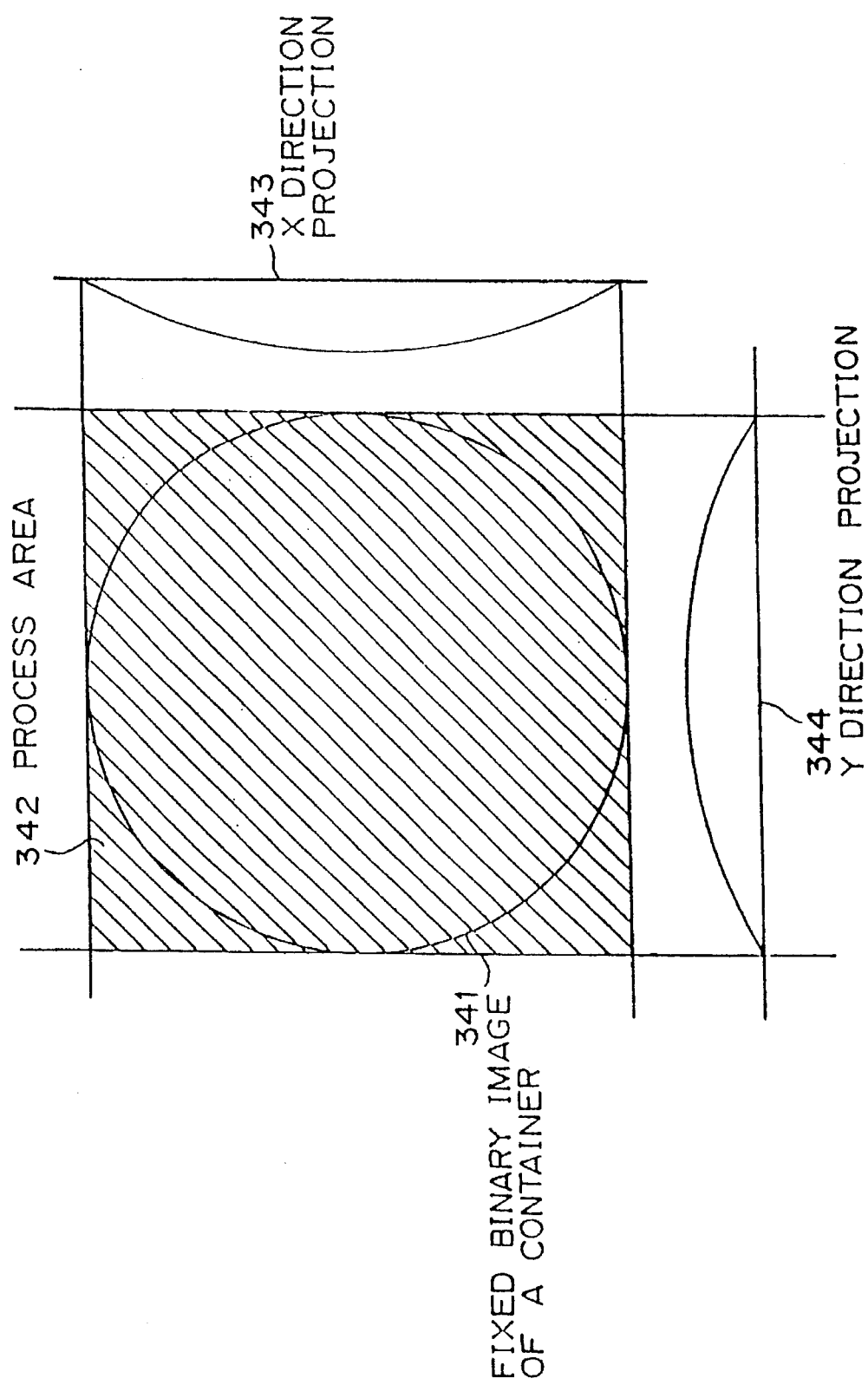
FIG. 34 shows a method of determining the process area for a container.

FIG. 34 shows a method of detecting the bounding rectangle of the container, that is, the process area indicated by diagonal-shaded portion according to the amount of the X-direction projection 343 and the Y-direction projection 344 using the fixed binary image 341 of the container. If containers are carried adjacently on a conveyor, the process area 342 is determined after a process area separation determination circuit 34 separates adjacent containers.

Next, an image edge detecting circuit 85 and a position error amount determining circuit 89 generate a window at a correct position relative to the target image.

Figure 35:
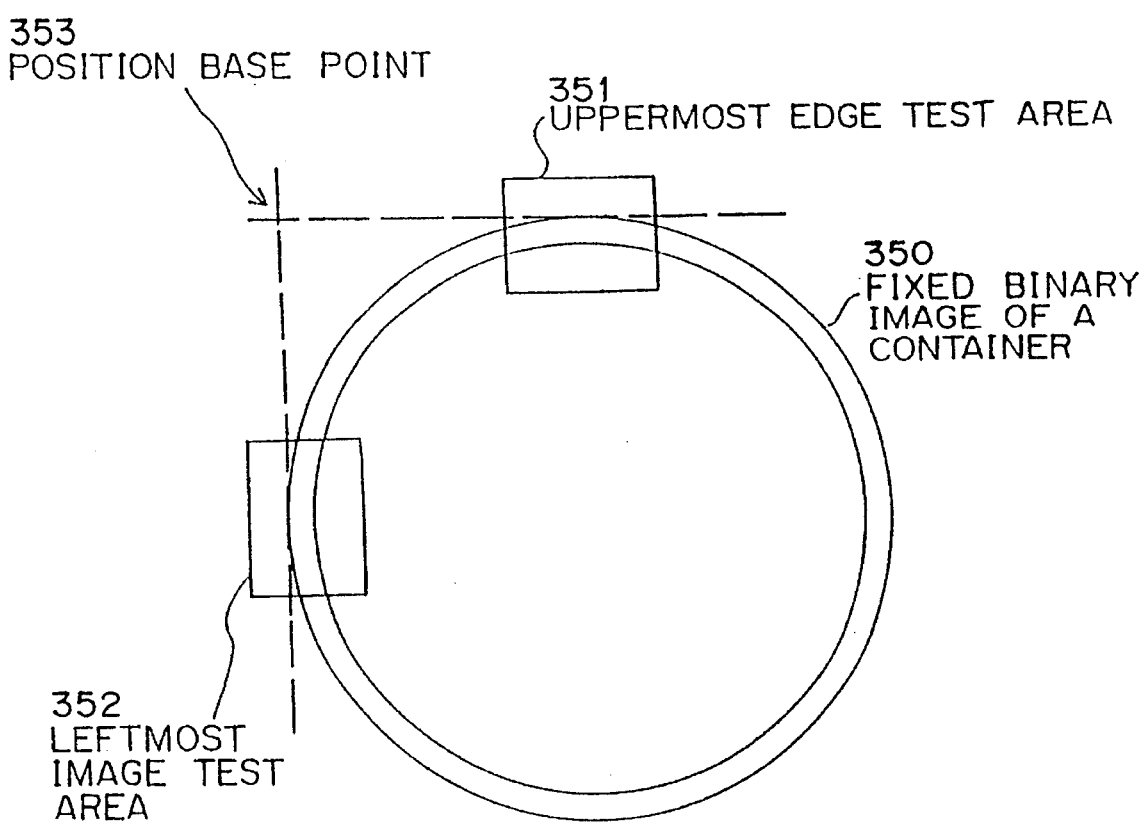
FIG. 35 shows a view for explaining the operation of the image edge detecting circuit.

FIG. 35 shows a view for explaining the operation of the image edge detecting circuit 85. The edge detecting circuit 85 receives the latest multi-valve continuous tone image signal PO during the operation of the above-described projecting circuits 29 and 30, and generates a fixed binary image 350 of a bottom highlighted portion so that the center of the target image can be easily detected. However, the threshold used in this process is generally different from that used by the image edge detecting circuit 26-1.

Then, the coordinates of the edges in a predetermined area for the fixed binary image 362 (in this example, the uppermost edge in the uppermost edge test area 351 and the leftmost edge in the leftmost edge test area 352), that is, the coordinates of the position base point 353 are detected.

The position error amount determining circuit 89 compares the coordinates of the position base point 353 with predetermined base coordinates, and detects the difference between the center position of the currently detected target image and the center position of the predetermined window.

Each of the processes performed by the image edge detecting circuit 26-1, the defect detecting circuit 83, the image edge detecting circuit 85, the X projecting circuit 29, and the Y projecting circuit 30, is not performed by the defect detecting circuit 84, but by the raster address generators 23F and 81. Then, control is transferred to the circular address generators 80 and 82 to generate a circular address and operate the defect detecting circuit 84.

Figure 36:
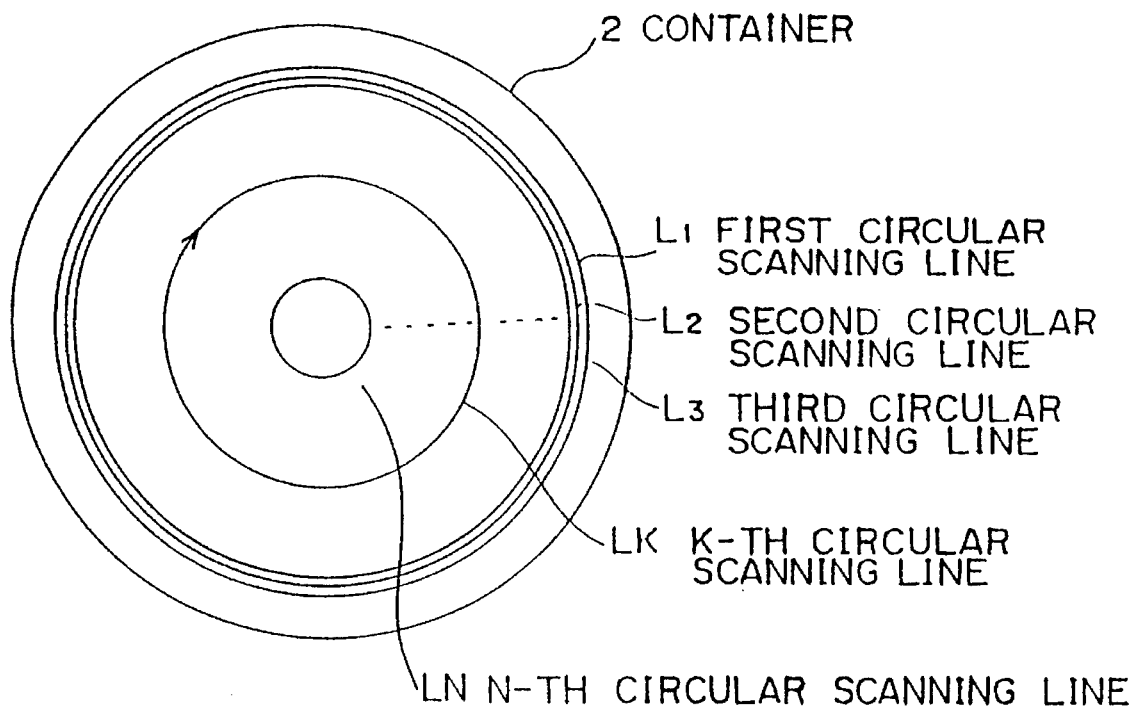
FIG. 36 shows a method of generating a circular address in the present invention.

FIG. 36 shows the method of generating a circular address. In this example, the concentric ring scanning lines (circular scanning lines) L (L1–Ln) are generated for searching the side of the container 2, that is, the image area between the opening highlighted portion 3 and the bottom highlighted portion 4 shown in FIGS. 1A and 1B, at intervals of one or more picture element (the interval is determined depending on the size of a defective concave to be detected). The image is circularly scanned clockwise and sequentially for each scanning line L from L1, L2, ... Lk, ... Ln with the scanning lines switched one after another. As described later in FIG. 40, circular addresses are generated such that the X and Y coordinates of target picture elements arranged every two or more picture elements are specified sequentially in the order of the scanning operation.

Instead of the above described concentric circular scanning lines, the circular scanning lines can be a spiral scanning line the scanning radius of which changes sequentially over each cycle (in this case, the radius gets smaller).

Figure 37A:
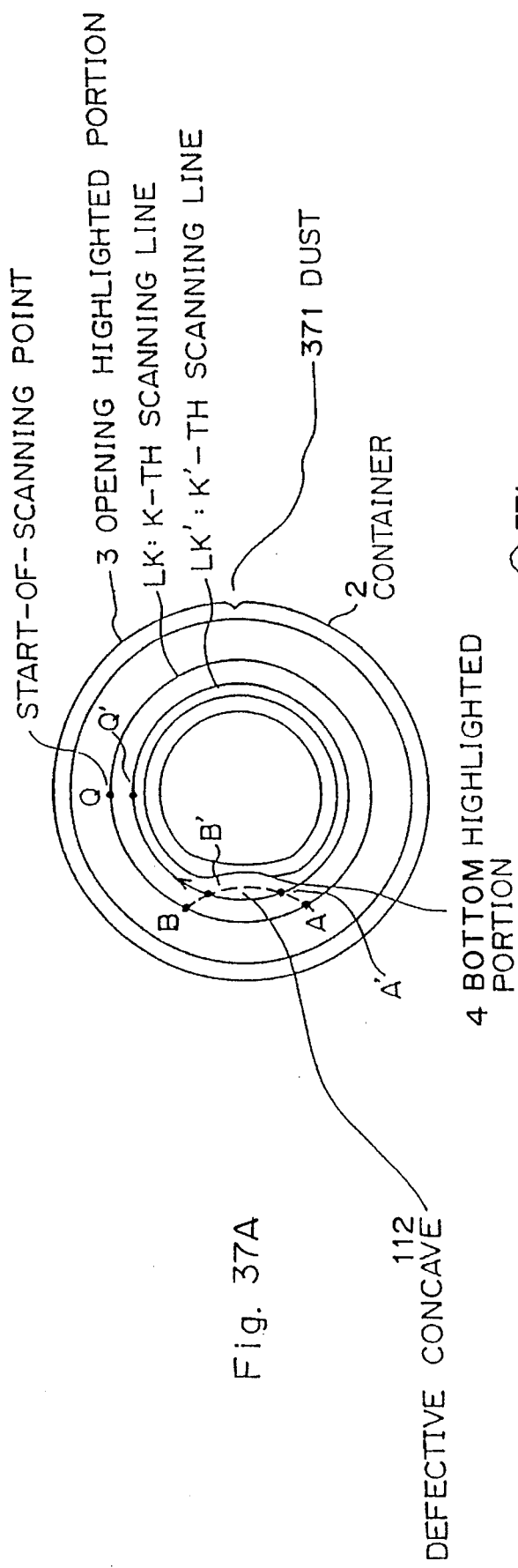
FIGS. 37A and 37B show example of an image of a container having a concave portion.
Figure 37B:
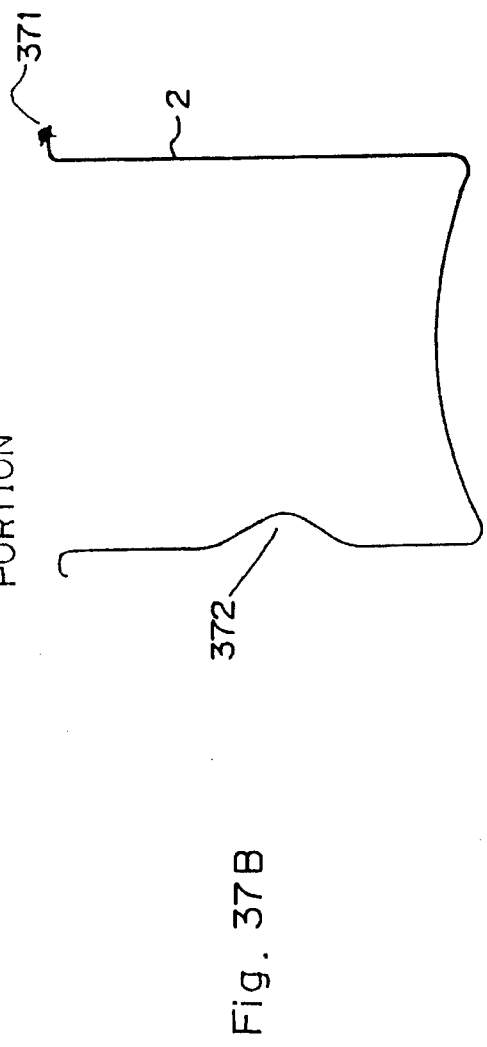

FIGS. 37A and 37B show an example of a continuous tone image which indicates that the side of the container 2 shown in FIG. 27B has a defective concave 372. In this case, a defective concave 372 exists between A and B on the k-th scanning line Lk, and between A' and B' on the scanning line Lk' of the circular scanning lines. Points Q and Q' indicate a start-of-scanning point on the circular scanning lines.

Figure 38:
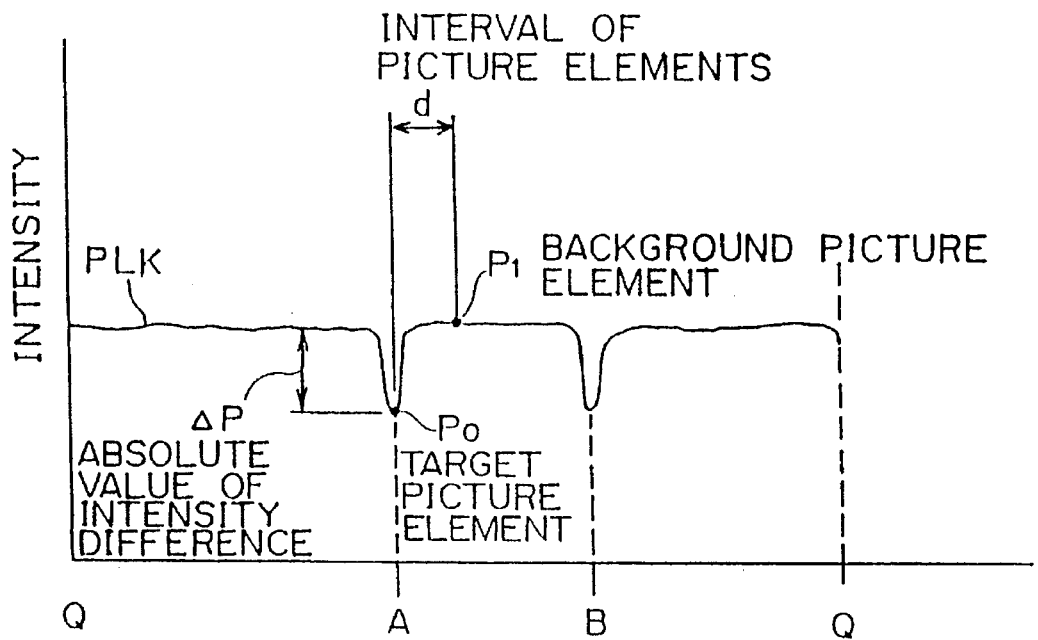
FIG. 38 shows an embodiment of the intensity variations on a scanning line, and shows the principle of the defect detecting circuit based on the circular method shown in FIG. 33.

FIG. 38 shows a view for explaining the principle of the defect detecting circuit 84 of the circular method shown in FIG. 33. PLK shown in FIG. 38 shows an example of intensity variations of the image data on the k-th scanning line Lk. The characters Q, A, and B on the horizontal axis shown in FIG. 38 correspond to the characters shown in FIG. 37A. PO indicates a target picture element and its value, and P1 indicates a background picture element and its value. The background picture element is positioned a predetermined number d of picture elements away from the target picture element.

The defect detecting circuit 84 compares the threshold THP predetermined for the window containing the k-th scanning line Lk with the absolute value of the difference between the above described picture element values PO and P1 calculated as follows.

$$\Delta P = \|PO-P1\|$$

If $\Delta P > THP$, it is determined that the target picture element PO indicates a defective inner surface such as a defective concave, etc.

Figure 39:
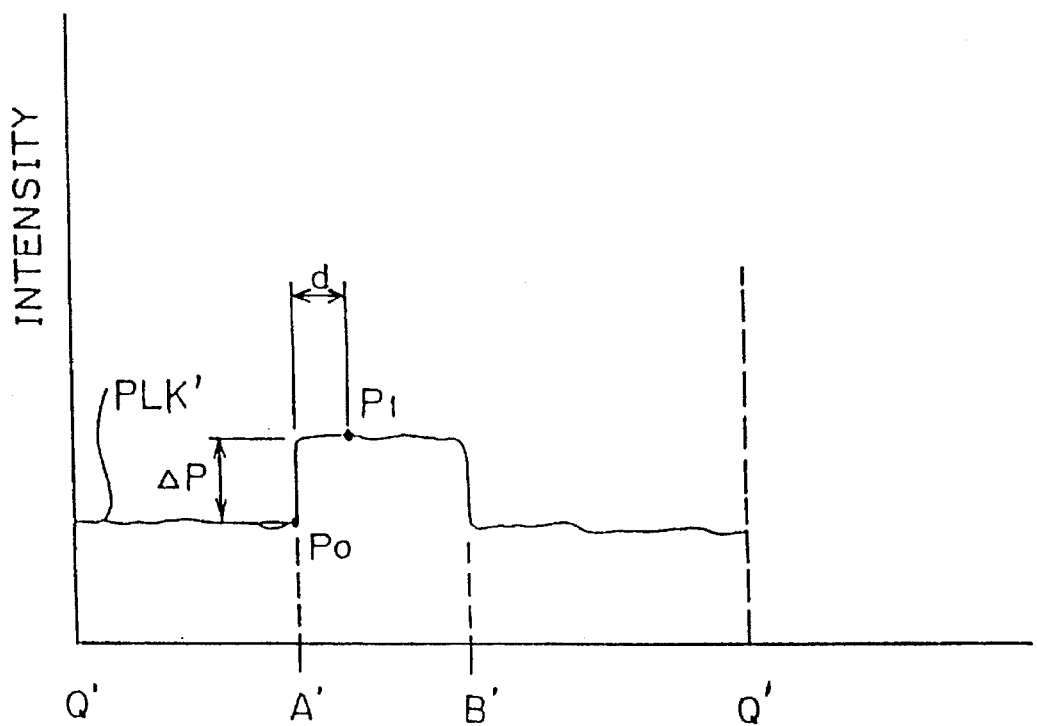
FIG. 39 shows another view for explaining the principle of the defect detecting circuit 84 on the scanning line, and shows the principle of the defect detecting circuit based on the circular method shown in FIG. 33.

FIG. 39 shows another view for explaining the principle of the defect detecting circuit 84. PLK' in FIG. 39 shows an example of the intensity variations of the picture element data on the k-th scanning line Lk'. The characters Q', A', and B' on the horizontal axis shown in FIG. 39 correspond to the characters shown in FIG. 37A. The k'-th scanning line Lk' shown in FIG. 37A runs through the low intensity portion existing along the outside of the bottom highlighted portion 104. If a defective concave exists on this portion, the defective concave is highlighted as shown in FIG. 39, and the sign for the intensity difference PO-P1 is inverted from that shown in FIG. 38. However, as shown in FIG. 38, the defect detecting circuit 84 shown in FIG. 39 compares the threshold THP predetermined for the window containing the k'th scanning line LK with the absolute value of the difference in intensity variation obtained as follows.

$$\Delta P = \|PO-P1\|$$

If $\Delta P > THP$, it is determined that the target picture element Po indicates a defective inner surface such as a defective concave, etc.

Figure 40:
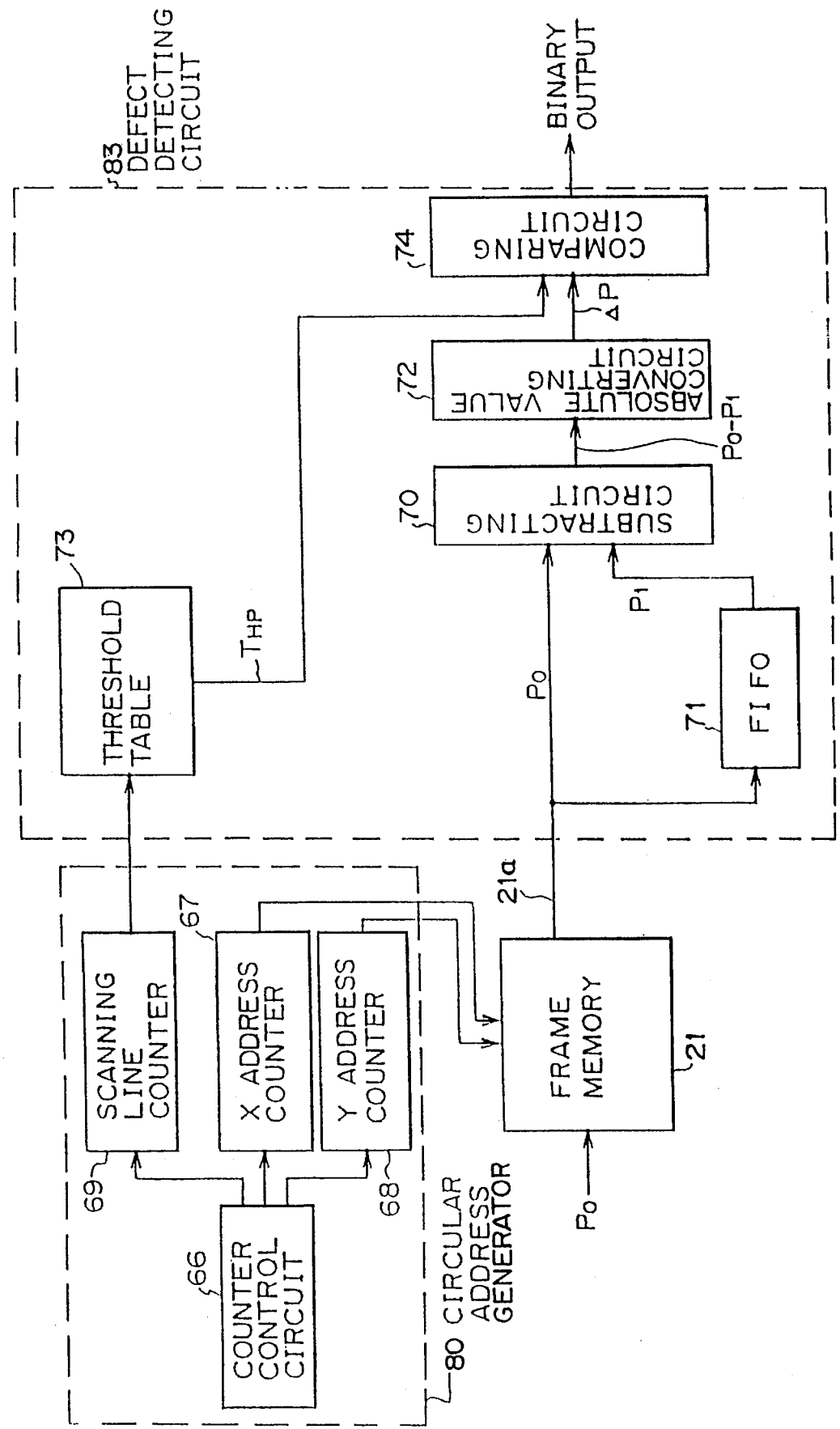
FIG. 40 shows an embodiment of the configuration of the circular address generator and the defect detecting circuit based on the circular method shown in FIG. 33.

FIG. 40 is a block diagram of the configuration of the circular address generator 80 and the defect detecting circuit 84 shown in FIG. 33. The counter control circuit 66 in the circular address generator 80 controls an X address counter 67 and a Y address counter 68 in the circular address generator 80 to sequentially output X and Y addresses as circular addresses of each target picture element in the order of scanning lines L1, L2, ..., Ln shown in FIG. 36 from the counters 67 and 68, to the frame memory 21. The scanning counter 69 is provided in the circular address generator 80, and the value indicated by the counter 69 is incremented by 1 each time the test image is scanned along one circle.

In the defect detecting circuit 83, a continuous tone image signal (picture element value) 21a read according to the above described circular addresses from the frame memory 21 is sequentially inputted to a subtracting circuit 70 and a FIFO 71. The FIFO 71 delays the inputted image signal 1a by the number d (the above described interval of target picture elements).

Therefore, the subtracting circuit 70 receives the image signal 21a as a value PO of the target picture element shown in FIG. 38, receives a picture element value outputted by the FIFO 71 as a value P1 of the background picture element separated from the target picture element shown in FIG. 38 by the number d (the above described interval of target picture elements), and obtains the difference between them (P0-P1). The absolute value converting circuit 72 obtains the absolute value ($\|Po-P1\| = \Delta P$) of the difference P0-P1.

The threshold table 73 in the defect detecting circuit 84 outputs a threshold THP according to the address outputted by the scanning line counter 69 (that is, the address for each of scanning lines L1, L2, ..., Ln). At this time, the threshold THP in a window can be set to the same value.

A comparing circuit 74 compares the above described absolute value $\Delta P$ of the difference in intensity with the threshold THP, and outputs a binary conversion signal as the determination of whether or not the target picture element indicates a defective concave, etc., according to whether or not __P>THP exists.

Figure 41:
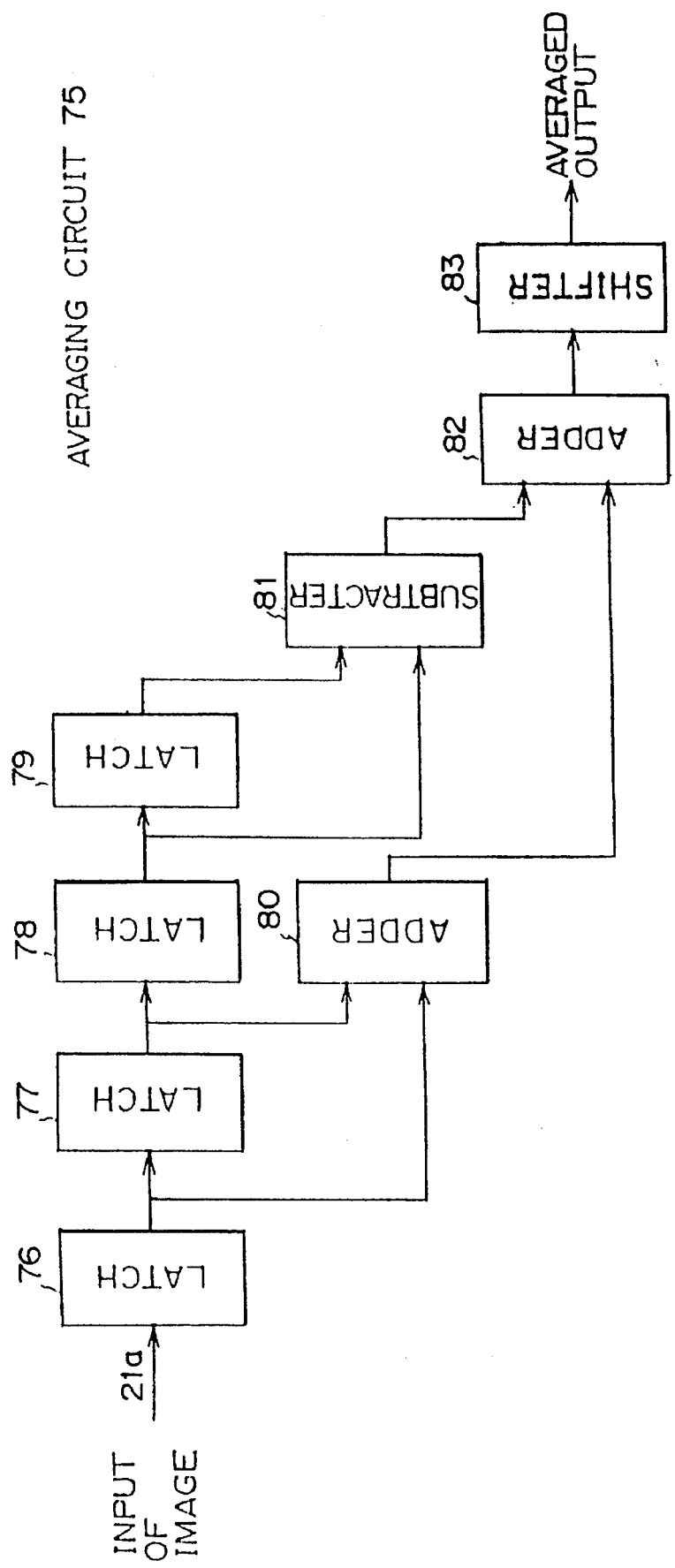
FIG. 41 shows an embodiment of the circuit for applying a moving average to the background picture element values shown in FIG. 40.

FIG. 41 shows an example of the configuration of an averaging circuit 106 for applying a moving average to the picture element value P1 outputted by the FIFO 71 shown in FIG. 40. The circuit 75 is provided in series with the FIFO 71 shown in FIG. 39 (in this example, between the frame memory 1 and the FIFO 71). The averaging circuit 75 calculates the moving average of four picture elements sequentially inputted in series. While an inputted image signal (picture element value) 1a is transmitted to latches 76, 77, 78, and 79 sequentially in this circuit 75, the image data in latches 76 and 77 are added by an adder 80, and the image data in latches 78 and 79 are added by an adder 81. Then, the addition results are added by an adder 82, and thus, the sum of four picture element values is obtained. A shifter 83 calculates an averaged output by shifting the resultant sum by two bits to right (that is, the sum is divided by 4).

Figure 42:
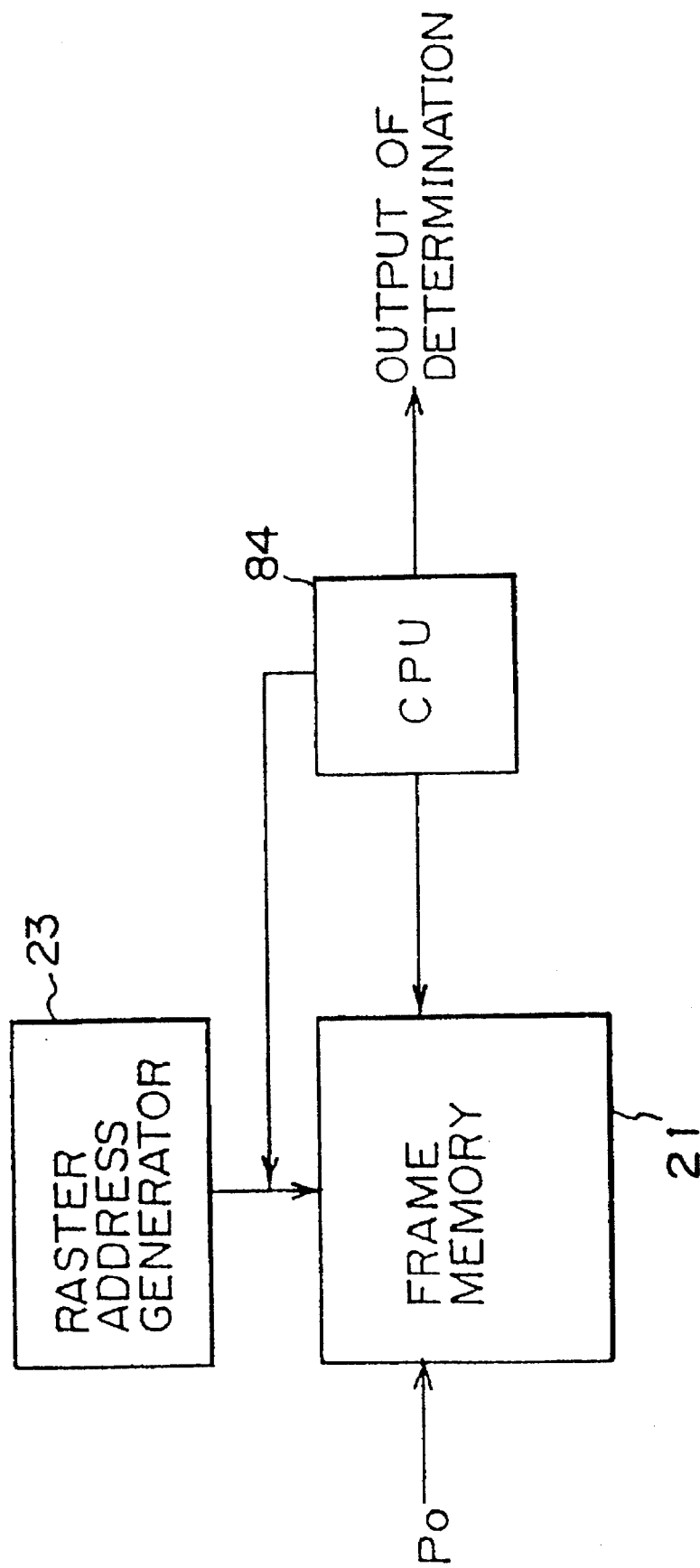
FIG. 42 is a block diagram of an embodiment of the configuration in which circular addresses shown in FIG. 33 is generated by software.

FIG. 42 shows an example in which a CPU 84 replaces using software the functions of the circuit excluding the frame memory 21 and the raster address generator 23F shown in FIG. 33. In this case, since the circular address generating circuits 80 and 82 operating as the hardware for accessing the frame memory 21 are not provided independently, it is supposed that the processing time of the CPU 84 is longer. Therefore, it is required that the processing time of the CPU 84 be shortened and the interval between circular scanning lines L be appropriately extended, or the interval between target picture elements on the scanning line L be extended.

Figure 43:
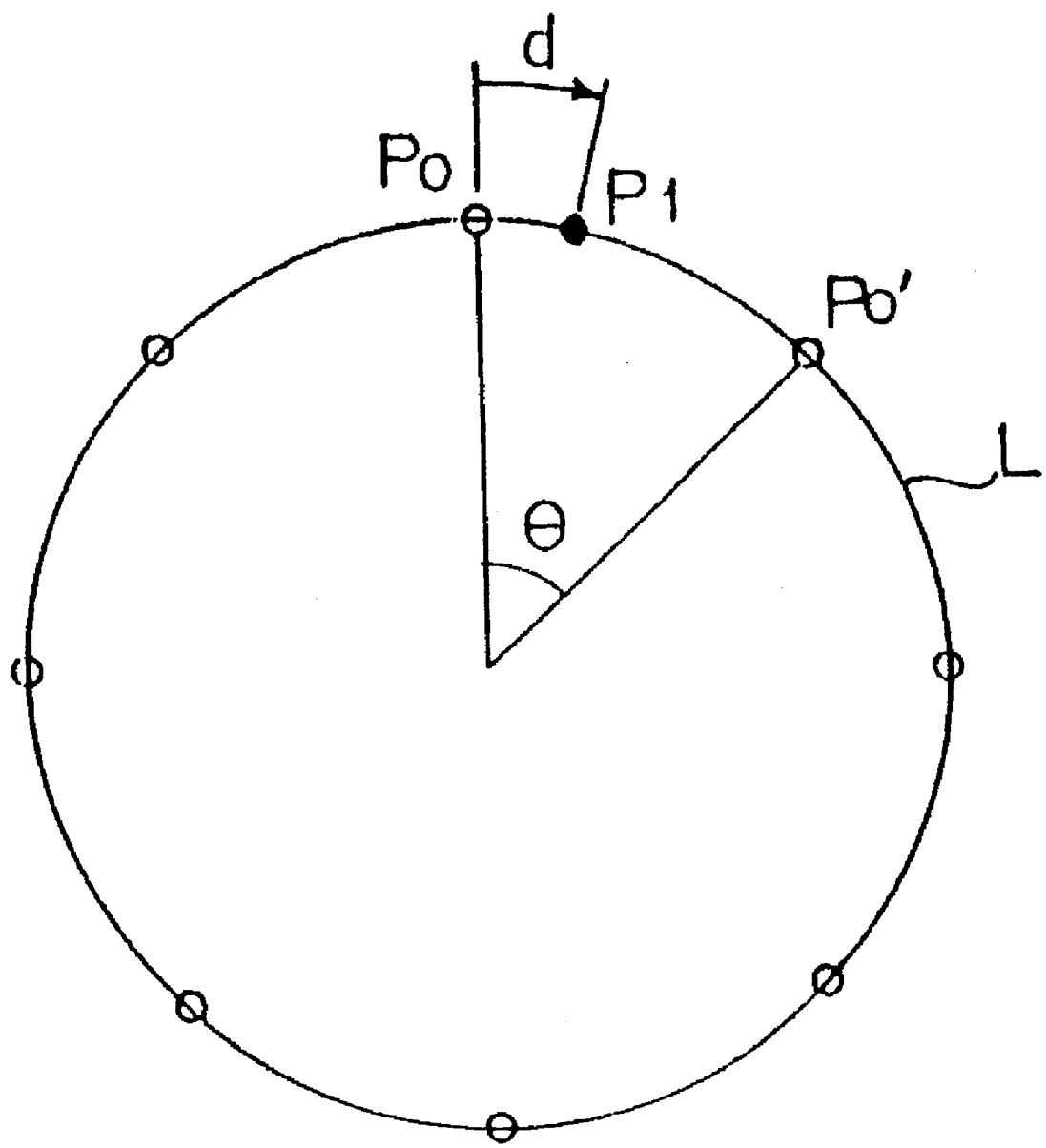
FIG. 43 is an embodiment of the process by the CPU shown in FIG. 42.

FIG. 43 shows an example of shortening the processing time. First, the data of the target picture element Po on the circular scanning line L are read. Then, the data of the background picture element P1 separated from Po by the number d of picture elements is read. The absolute value of the intensity difference between the two picture elements is obtained ($\|Po-P1\|$). Then, the absolute value of the intensity difference is compared with the predetermined threshold THP and the target picture element Po is converted to the binary representation to determine whether or not the target picture element indicates a defect. If it does not indicate a defect, control is transferred to the next target picture element Po' separated from the present one by θ, and the above described process is performed on it. The scanning operation completes when all circular scanning lines are processed.

The defect detection determining circuit 88 determines such that the number of picture elements indicating a defect is accumulated over one or more circular scanning lines, the number is compared with a predetermined area threshold, and then it is determined whether or not the inner surface of the container under test has a defect.

The average intensity of the picture elements forming a predetermined two-dimensional local area (for example, an area of 3 picture elements ×3 picture elements) centered on the background picture element P1 can replace the average intensity of a predetermined number of picture elements (a one-dimensional local area) arranged on the circular scanning line L centered on the background picture element P1 shown in FIG. 41.

With the above described configuration of the cylindrical container inner surface tester, the image of a cylindrical container is scanned along a ring or spiral circular scanning line. Then, the difference in intensity between picture elements arranged at predetermined intervals along the scanning line is obtained. If the absolute value indicating the intensity difference exceeds a threshold predetermined according to the position of the circular scanning line, it indicates a defect of the container, such as a concave, etc. Therefore, a slight local concave on the side of a cylindrical container can be exactly detected.

Figure 44:
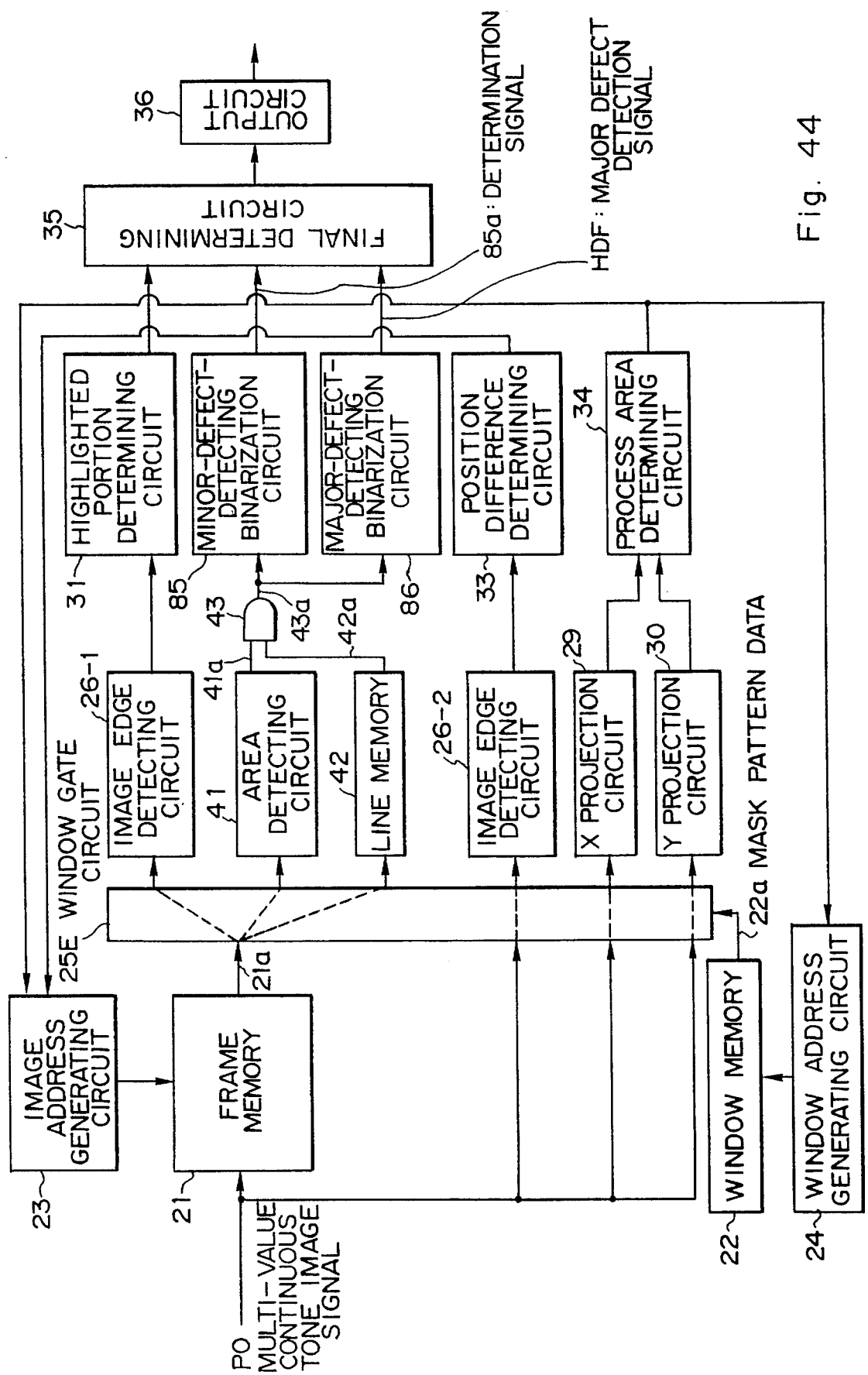
FIG. 44 is the block diagram showing the hardware configuration according to the fifth embodiment of the present invention.

FIG. 44 is the block diagram showing the hardware according to the 5th embodiment of the present invention. In the embodiment, a minor-defect-detecting binarization circuit 85 and a major-defect-detecting binarization circuit 86 are provided in place of the peak/valley-detection binary-conversion circuit shown in the block diagram of FIG. 26. Other circuits are the same as those shown in FIG. 26, and assigned the corresponding numbers therein.

As shown in FIG. 44, the AND circuit 43 ANDs area detection signal 41a outputted by the area detection circuit 41 and continuous tone image signal 42a, which is an image signal for each horizontal scanning line of the area and is outputted by the line memory 42, and outputs a continuous tone image signal for a defect test area only, that is, test area continuous tone image signal 43a to the minor-defect-detecting binarization circuit 85 and the major-defect-detecting binarization circuit 86. As described by referring to FIG. 26, even if the center of the test container 2 indicates a discrepancy from the center of the image and the contour of the image does not indicate a right circle, the AND circuit 43 outputs test area continuous tone image signal 43a with a continuous tone image signal for a portion other than the contour of the container 2 exactly removed.

The above described minor-defect-detecting binarization circuit 85 detects a picture element having a minor defect (not indicating a major defect). That is, the minor-defect-detecting binarization circuit 85 converts test area continuous tone image signal 43a to a binary value using a fixed binary threshold preliminarily set for each window area (that is, a threshold used in a fixed binary conversion method). Likewise, the intensity difference between a target picture element and its background picture element of continuous tone image signal 43a is converted to a binary value using a difference binary threshold predetermined for each window area (that is, a threshold used in a difference binary conversion method). Thus, a picture element indicating a minor defect is extracted. Furthermore, the circuit 85 counts as a defect area value the number of picture elements indicating a defect in a binary representation, compares the count result with the predetermined minor defect detection threshold, and outputs determination signal 85a to the final determining circuit 35.

The minor-defect-detecting binarization circuit 85 can be designed to include the function of the peak/valley-detecting binary-conversion circuit 44 shown in FIG. 26.

Figure 45:
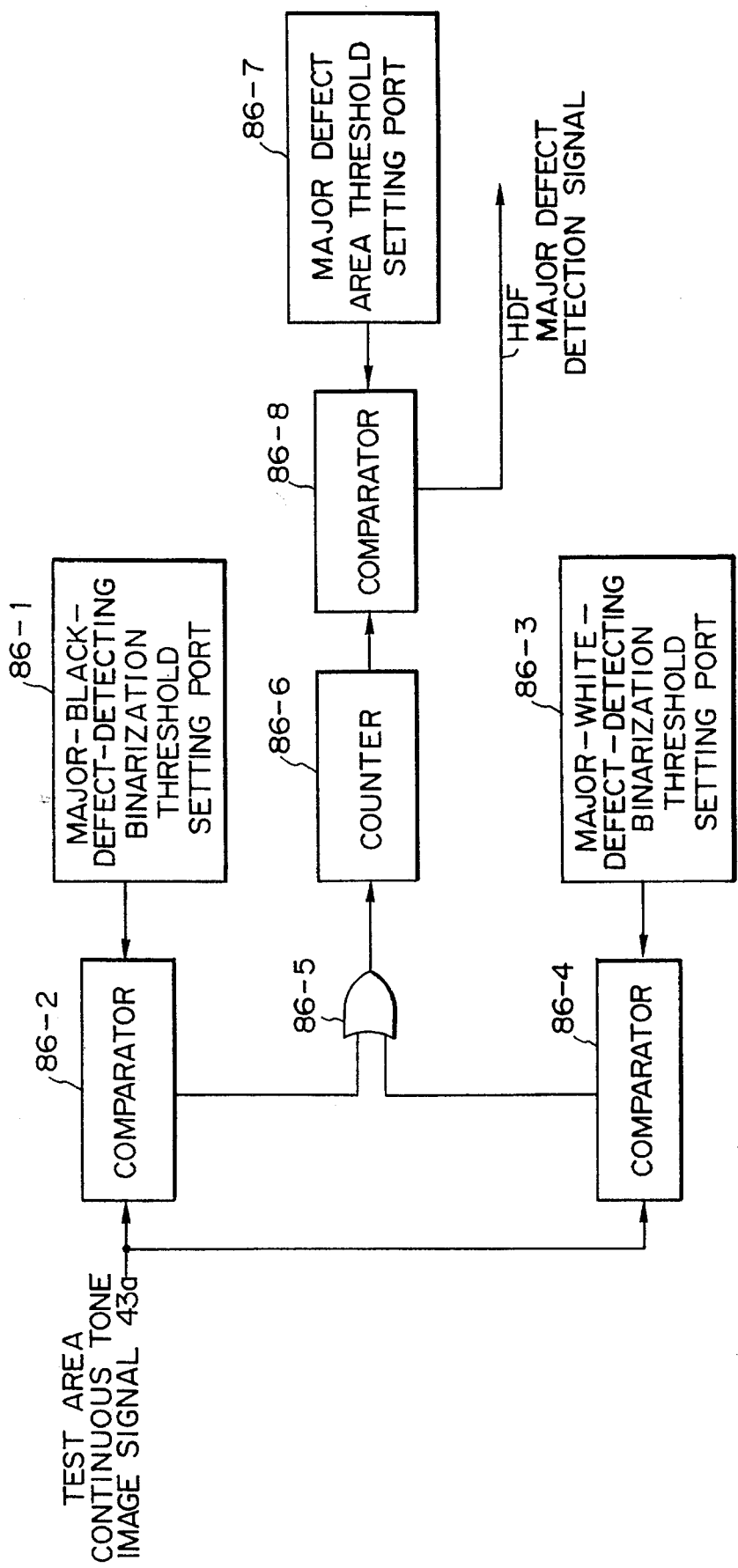
FIG. 45 is the block diagram showing the detailed configuration of the major-defect-detecting binarization circuit shown in FIG. 44.

FIG. 45 is the block diagram showing the detailed configuration of the major-defect-detecting binarization circuit 86 which is the most important core in the present invention. In FIG. 45, a black-defect-picture-element detection binary threshold setting port 86-1 outputs a binary threshold for use in detecting a picture element indicating a black defect to a comparator 86-2. The comparator 86-2 converts test area continuous tone image signal 43a, which is inputted through the AND circuit shown in FIG. 44, to a fixed binary value based on the above described binary threshold, and outputs the result to an OR circuit 86-5. A white-defect-picture element detection binary threshold setting port 86-3 outputs a binary threshold for use in detecting a picture element indicating a white defect to a comparator 86-4. The comparator 86-2 converts test area continuous tone image signal 43a, which is inputted through the AND circuit shown in FIG. 44, to a fixed binary value based on the above-described binary threshold, and outputs the result to the OR circuit 86-5. The OR circuit 86-5 composes the inputs from the comparators 86-2 and 86-4 and outputs the result to a counter 86-6. The counter 86-6 counts an input value from the OR circuit 86-5 to obtain a sum of picture elements indicating a major defect, that is, a major defect area value, and outputs a major defect area value for one window area to a comparator 86-8 each time a scanning operation is completed for 1 window area.

On the other hand, the comparator 86-8 receives from a major-defect-area threshold setting port 86-7 a major defect area threshold for the present window selected from among major defect area thresholds separately set for each window. The comparator 86-8 compares the major defect area threshold with the major defect area value inputted by the above-described counter 86-6. If the major defect area value outputted by the counter 86-6 is larger than the major defect area threshold, then the comparator 86-8 outputs a major-defect detection signal HDF indicating that the present cylindrical container 2 is a major-defective container (an occurrence of a major defect) to a final determining circuit 35.

A fixed binary threshold is predetermined by the CPU (not shown in the attached drawings) for each of the major-black-defect-detecting binarization threshold setting port 86-1, the major-white-defect-detecting binarization threshold setting port 86-3, and the major-defect-area threshold setting port 86-7 separately for each window area before a scanning of images. The above-described fixed binary threshold is obtained by amending the illuminance of a test image obtained using an image illuminance measuring unit (not shown in the attached drawings), and the obtained value is appropriately amended.

Figure 46:
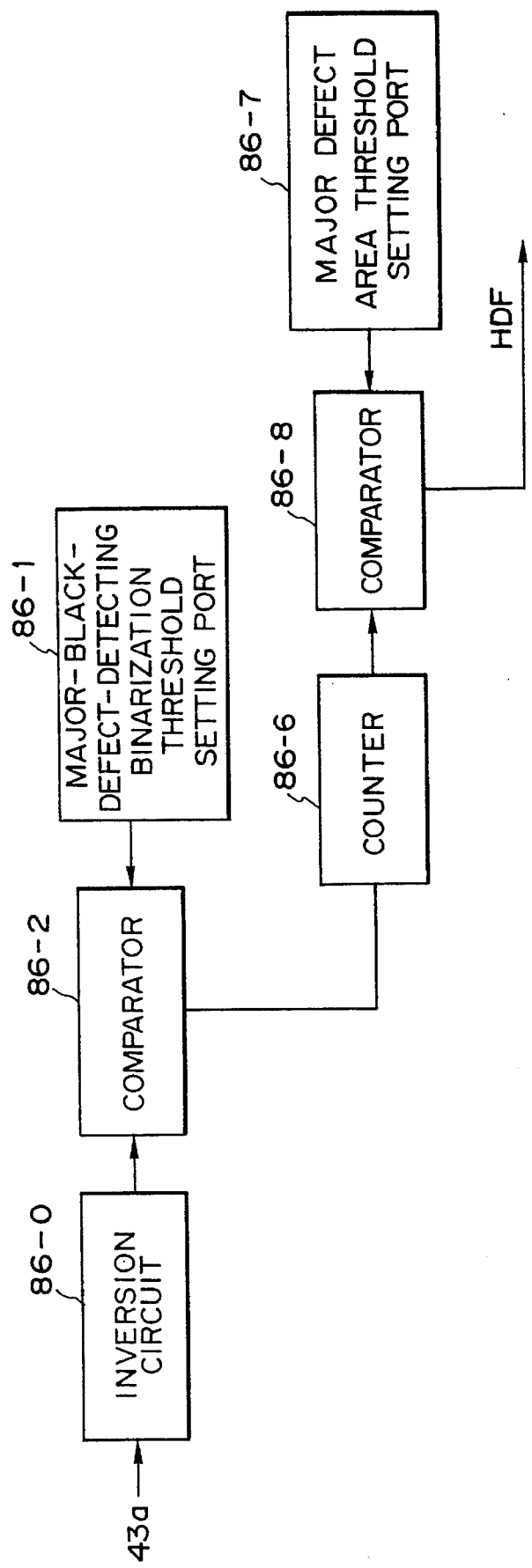
FIG. 46 is the block diagram showing the detailed configuration of the major-defect-detecting binarization circuit according to the 5th embodiment of the present invention.

FIG. 46 is the block diagram showing the detailed configuration of the major-defect-detecting binarization circuit 86 according to the 5th embodiment of the present invention. FIG. 46 is prepared by omitting the white major-defect-detecting binarization threshold setting port 86-3, the comparator 86-4 for converting continuous tone image signal 43a to a fixed binary value, and the OR circuit 86-5 in the circuit shown in FIG. 45. When an inversion circuit 86-0 shown in FIG. 46 is set to a right (non-inversion) position, the circuit shown in FIG. 46 is equivalent to the circuit shown in FIG. 45 in which the major-white-defect-detecting binarization threshold setting port 86-3 is set to the maximum intensity value of images to make the circuit inoperative.

The same result as that obtained with the configuration shown in FIG. 45 can also be obtained by setting the inversion circuit 86-0 to a right (non-inversion) position to scan one window area and count the number of picture elements indicating a black major defect before setting the inversion circuit 86-0 to an inversion position to re-scan the same window area and count the number of picture elements indicating a white major defect.

Figure 47:
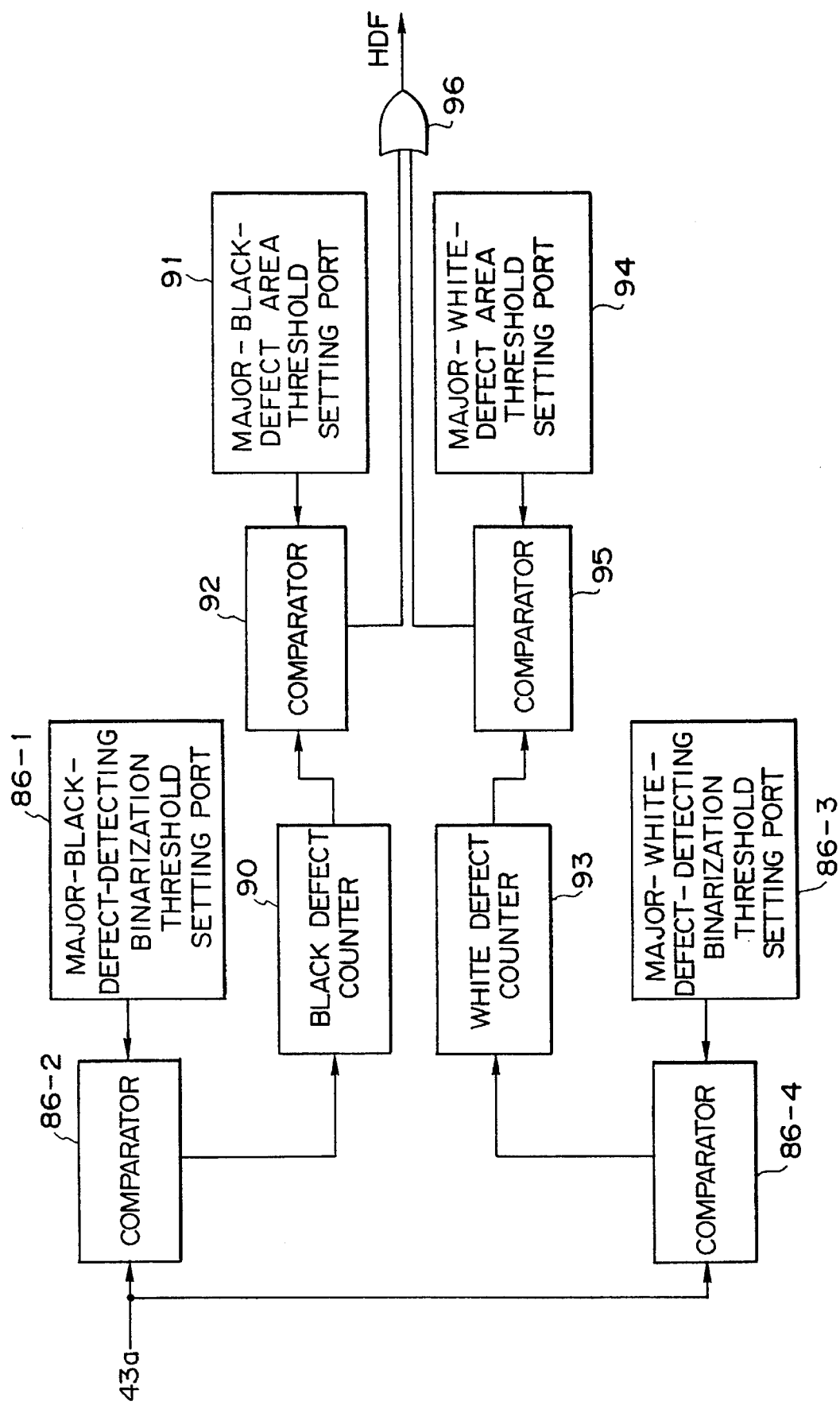
FIG. 47 is the block diagram showing the detailed configuration of the major-defect-detecting binarization circuit according to the sixth embodiment of the present invention.

FIG. 47 shows the detailed configuration of the major-defect-detecting binarization circuit 25 according to the 6th embodiment of the present invention. FIG. 47 shows the configuration in which a binary threshold is set by the setting ports 86-1 and 86-3 for use in detection of picture elements indicating a black major defect and a white major defect respectively; an area threshold is set by the setting ports 91 and 94 for picture elements indicating a black major defect and a white major defect respectively; and the picture elements can be counted during the scanning operation. The circuit counts the number of picture elements indicating a black major defect by a black defect counter 90, a black-major-defect area threshold setting port 91, and a comparator 92, counts the number of picture elements indicating a white major defect by a white defect counter 93, a white-major-defect area threshold setting port 94, and a comparator 95, and finally obtains a logical sum of detection signals by an OR circuit 96 and outputs the result to the final determining circuit 35 shown in FIG. 44.

Figure 48:
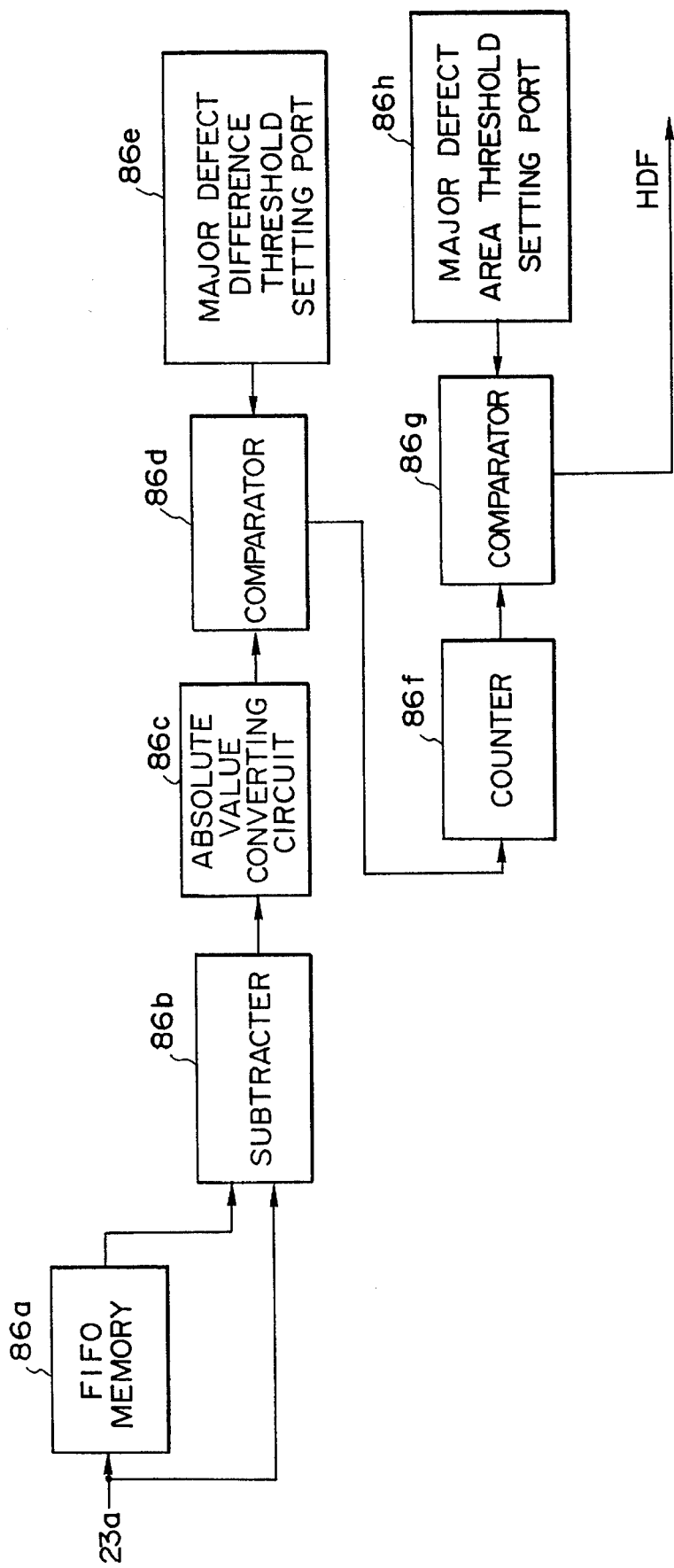
FIG. 48 is the block diagram showing the detailed configuration of the major-defect-detecting binarization circuit according to the seventh embodiment of the present invention.

Next, FIG. 48 shows the configuration of the major-defect-detecting binarization circuit 86 according to the 7th embodiment of the present invention. In FIG. 48, a FIFO memory 86a temporarily stores input signal (test area continuous tone image signal) 43a. The FIFO memory 86a provides a signal delayed by the predetermined number of picture elements (that is, a background picture element signal) with a subtracter 86b as the input signal thereof. The subtracter 86b directly receives an input signal (that is, a target picture element signal). The subtracter 86b subtracts a target picture element intensity value from a background picture element intensity value, and outputs the difference to an absolute value converting circuit 86c. The absolute value converting circuit 86c checks the sign bit of the inputted difference. If the sign bit indicates a negative value, it converts the value to a positive value and outputs the value to a comparator 86d. The comparator 86d receives a predetermined difference threshold from a major-defect-difference threshold setting port 86e. The comparator 86d compares the difference threshold with a difference signal received from the above-described absolute value converting circuit 86c, generates a binary difference signal, and outputs it to a counter 86f. The counter 86f calculates a major defect area value by counting the binary difference signal, and outputs the major defect area value to a comparator 86g. The comparator 86g receives a predetermined major defect area threshold set in a major defect area threshold setting port 86h. Then, the comparator 86g compares the major defect area threshold with the major defect area value inputted from the counter 86f. If the major defect area value outputted by the counter 86f is larger than the major defect area threshold, then a major defect detection signal HDF indicating that the present cylindrical container 2 has a major defect outputs it to the final determining circuit 35 shown in FIG. 44.

Each of the thresholds for the major defect difference threshold setting port 86e and the major defect area threshold setting port 86h is set by the CPU (not shown in the attached drawings) for each of the window areas before a scanning of images.

As a variation of the embodiment shown in FIG. 48, it is so designed that the absolute value converting circuit 86c shown in FIG. 48 can be deleted to obtain a difference image signal having positive and negative values, set a predetermined binary difference threshold individually for each of the positive and negative difference values for a major defect, and then obtain an area value by inputting to the counter 86f shown in FIG. 48, a logical sum of binary image signals converted by each of the above described comparators.

Figure 49:
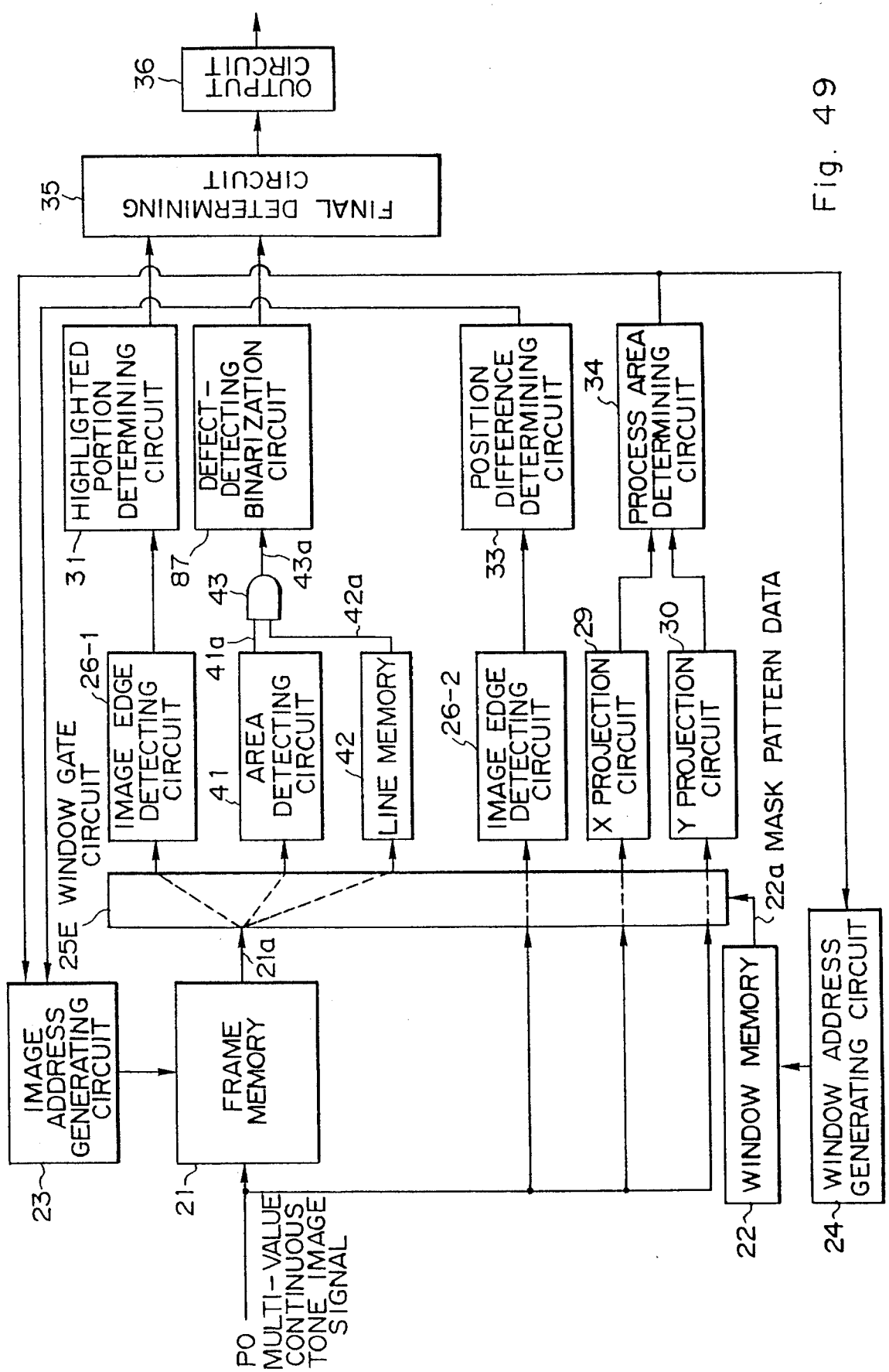
FIG. 49 is the block diagram showing the hardware according to the eights embodiment of the present invention.

FIG. 49 is the block diagram showing the hardware according to the 8th embodiment of the present invention. In the example shown in FIG. 49, the minor-defect-detecting binarization circuit 85 and the major-defect-detecting binarization circuit 86 shown in FIG. 44 are incorporated into a defect detecting circuit 87.

Figure 50:
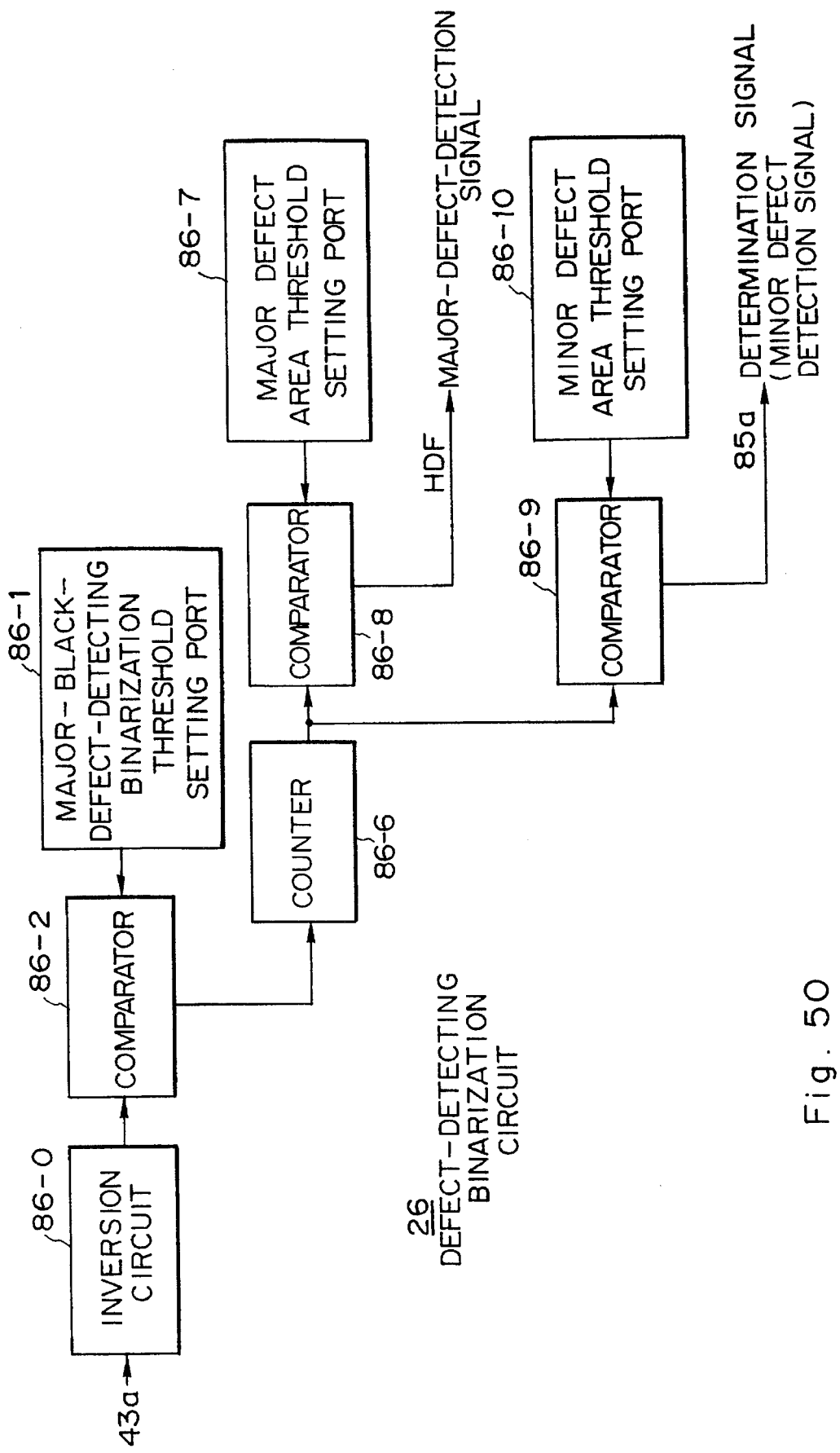
FIG. 50 is the block diagram showing the detailed configuration of the defect-detecting binarization circuit shown in FIG. 49.

FIG. 50 shows an example of the configuration of the defect detecting circuit 87. As shown in FIG. 50, a binary threshold of a major defect picture element and that of a minor defect picture element are specified as the same in the example, and the threshold is set in the major-black-defect-detecting binarization threshold setting port 86-1. A defect area value obtained by the counter 86-6 is compared with a major defect area threshold by the comparator 86-8 to output a major defect detecting signal HDF, while it is compared with a minor defect area threshold by the comparator 86-9 to output a determination signal (minor defect detection signal). As in the circuit shown in FIG. 46, a major defect or a minor defect for a black or white spot can be detected by inputting test area continuous tone image signal 43a with the inversion circuit 86-0 set to either a right or an inverse position so that a major or minor defect for a black or a white spot can be detected.

The occurrence of a container having a major defect can be minimized by stopping the production of containers when the major defect detection signal HDF is outputted. The cause of major defects can be easily anticipated by displaying the name of the window area for which the major defect detection signal HDF has been generated on the CRT screen of a checking monitor (not shown in the attached drawings).

Cylindrical containers have been considered above, but the present invention is not limited to a test of cylindrical containers, and can be applied to a test of the inner surface of a polygonal pole container having angles equal to or more than three.

Figure 51:
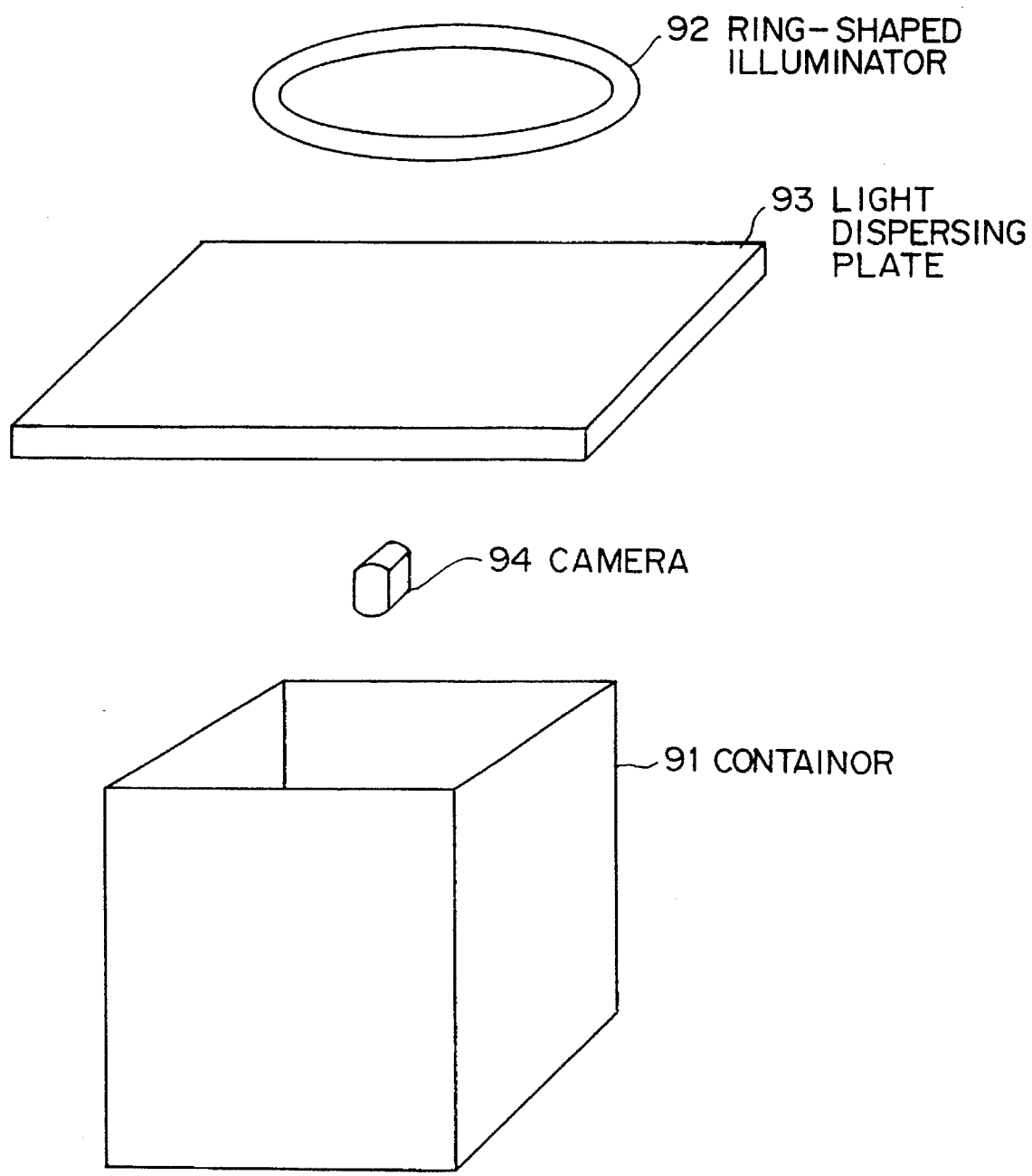
FIG. 51 shows an example of a square pole container as an example of a polygonal pole container.

FIG. 51 shows an example of a square pole container as an example of a polygonal pole container. With the embodiment shown in FIG. 51, a ring-shaped illuminator 92 irradiates the inner surface of a square pole container 91 from above it through a light dispersing plate 93. A camera 94 is located above the container and captures the inner surface of the square pole container 91.

In this case, a container conveyor fixes the position of the square pole container 91 during the transmission of the square pole container 91 to the above described capturing position. The position of the polygonal pole container can be easily fixed by the container conveyor.

Figure 52:
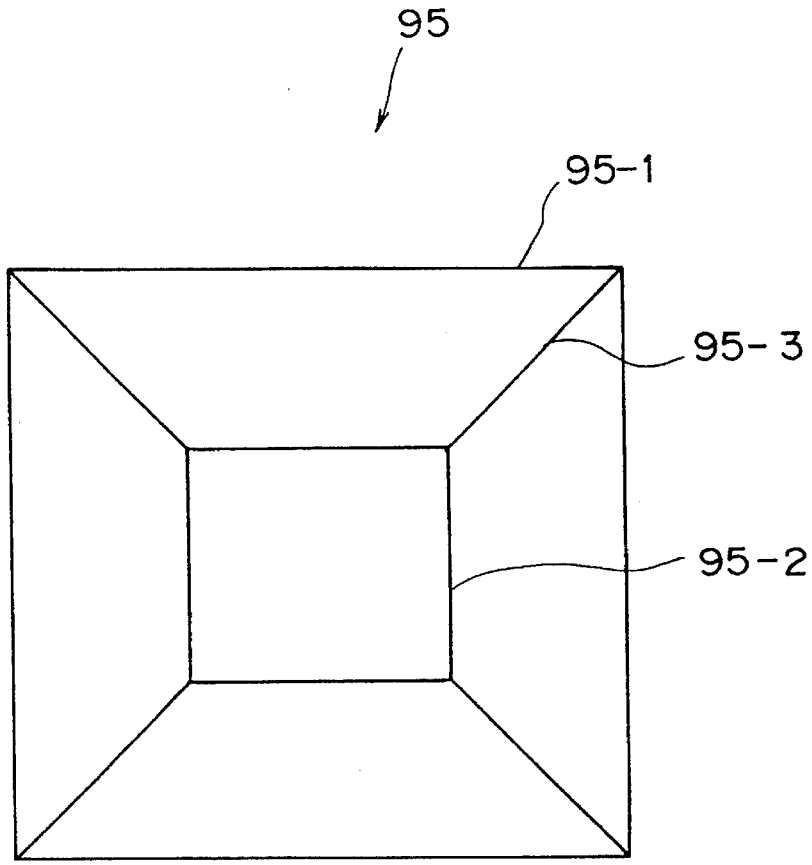
FIG. 52 shows an image 95 of the square pole container 91 captured and stored in the frame memory 21.

FIG. 52 shows an image 95 of the square pole container 91 captured and stored in the frame memory 21. The image 95 shows variations in intensity for four brims 95-1 of the upper opening, connections 95-2 between the bottom and the four sides, and connections (corners) 95-3 of the four sides. As with the cylindrical container 2, a window area and its threshold are set for each intensity variation to detect minor and major defects.

What is claimed is:

1. A container inner surface tester for illuminating from above an opening of a test container located at a predetermined position with its opening set levelly, for capturing an image of said opening through a TV camera, and for detecting black and white spots on an inner surface of said container by analyzing, using defect detecting means, the image obtained by said television camera, said tester comprising:

a frame memory means for storing as image data a multi-value continuous tone image signal analog/digital-converted from a continuous tone image signal obtained by scanning said captured image, and an area detecting means for generating a binary image signal by binary-converting, using a predetermined threshold, a multi-valve continuous tone image signal read by horizontally or vertically scanning said frame memory means and for determining as a test area the area between the first rise point and the last fall point of each scanning line of said binary image signal generated depending on the intensity of an image during the period from the start to the end of the scanning operation.

2. The container inner surface tester according to claim 1 further comprising:

masking means for masking with predetermined mask pattern data an area having a different optical characteristic in the test area detected by said area detecting means.

3. A container inner surface tester for illuminating from above an opening of a test container located at a predetermined position with its opening set levelly, for capturing an image of said opening through a television camera, and for detecting black and white spots on an inner surface of said container by analyzing, using defect detecting means, the image obtained by said television camera, said tester comprising:

determining means for determining a defect when the image of the inner surface of said container is scanned along a ring or spiral scanning line (hereinafter referred to as a circular scanning line) which is centered on the center of the image and varies sequentially per cycle of a radius varying every one or more picture elements predetermined, comparing means for comparing an absolute value indicating the difference between an intensity of the target picture elements among a plurality of picture elements arranged at intervals such that one or more picture elements are arranged between two target picture elements and an intensity of background picture elements predetermined number of a plurality of picture elements forward or backward of the target picture element, with a threshold predetermined according to a position of the circular scanning line, and repeating means for repeating such processes for each target picture element, for said determining means determining a defective container inner surface when an absolute value larger than the value of the difference between said intensity values is detected.

4. The container inner surface tester according to claim 3, wherein said threshold is set to an optimum value every occasion of the circular scanning line.

5. The container inner surface tester according to claim 3, wherein the intensity of said background picture element equals an average intensity of the picture elements in a predetermined one- or two-dimensional local area centered on said background picture element.

6. A container surface tester for detecting a defective container by irradiating a surface of a container using an illuminator, capturing an image of said irradiated surface of the container, and analyzing the captured image, said tester comprising:

memory means for storing as captured image data a multi-value continuous tone image signal obtained by A/D-converting continuous tone image signals obtained through capturing and scanning processes; and a defect-detecting means for determining, by scanning said captured image data stored in said memory means, whether or not the container to be tested is a defective container based on the value of an area of a defect of the container.

7. The container surface tester according to claim 6 wherein said container is axis-symmetrical and cylindrical, and the defect of the container is detected by irradiating an inner surface of said container, said illuminator is ring-shaped one concentric with the cylindrical container, said image of the irradiated surface of the container is captured in an axis direction, to provide a concentric image for an analyzation, said defect-detecting means obtains a sum of numbers of picture elements indicating defects and determines the defect based on whether or not the sum exceeds an area threshold set for detection of the defective container.

8. The container surface tester according to claim 6 wherein said defect detecting means comprises means for setting a first fixed binarization threshold for detection of a picture element indicating a black defect (hereinafter referred to as first black level), and a first fixed binarization threshold for detection of a picture element indicating a white defect (hereinafter referred to as first white level), obtaining a sum of numbers of picture elements indicating black and white defects after converting to a binary value the multi-value continuous tone image signal read by scanning a frame memory with the first black and white levels, and finally determining whether or not the cylindrical container to be tested is a defective container based on a value of the sum of the numbers of the picture elements indicating black and white defects and based on whether or not the sum exceeds a first area threshold for detection of a defective container.

9. The container according to claim 6 wherein said container comprises a polygonal pole container.

10. A cylindrical container inner surface tester for detecting a defective container by irradiating an inner surface of a cylindrical container using a ring-shaped illuminator concentric with the axis-symmetric cylindrical container, capturing a concentric picture image of the irradiated surface of the cylindrical container using a television camera from above along an axis of the container, and analyzing the captured concentric picture image, comprising:

a frame memory means for storing, as screen data corresponding to a screen displaying the captured image, a multi-value continuous tone image signal as an analog/digital conversion signal of a continuous tone image signal obtained by scanning a screen displaying the captured image, dividing means for dividing an image area on an inner surface of the cylindrical container into a plurality of window area through which a picture element indicating a defect can be detected;

a first setting means for setting, for each of the window areas, a first fixed binary threshold for detection of a picture element indicating a black defect (hereinafter referred to as a first black level) and a first fixed binary threshold for detection of a picture element indicating a white defect (hereinafter referred to as a first white level);

obtaining means for obtaining a sum of a number of picture elements indicating black and white defects for each window area after converting to a binary value a multi-value continuous tone image signal read by scanning a frame memory with the first black and white levels set for each window area, and determining means for determining whether or not the test cylindrical container is a major-defective container based on a value of the sum (whether or not the sum exceeds a first area threshold set for each window area for detection of a major-defective container);

second setting means for setting, for each of the above described window areas, a second fixed binary threshold corresponding to a black level at least higher than the first black level (hereinafter referred to as a second black level), a second fixed binary threshold corresponding to a white level at least higher than the first white level (hereinafter referred to as a second white level), and a second area threshold having a value larger than the first area threshold for detection of a major-defective container if at least the first black level is equal to the second black level and the first white level is equal to the second white level; and outputting means for outputting a major defect detection signal indicating that the present container is a major-defective container externally, if a sum of a number of picture elements indicating a black defect and a white defect for each window area in which a binary conversion level is represented by the second black level and the second white level exceeds the second area threshold set for each window area.

11. The cylindrical container inner surface tester according to claim 6, wherein required amount of hardware can be reduced by equalizing the first black level, the first white level, or the first area threshold to the second black level, the second white level, or the second area threshold respectively.

12. The cylindrical container inner surface tester according to claim 6, wherein a production line of cylindrical containers is automatically stopped according to said major defect detection signal.

13. The cylindrical container inner surface tester according to claim 6, wherein when said major defect detection signal is outputted, a name of said window area associated with a major defect detection signal is displayed on the screen through which a test conducted according to the present invention is monitored.

14. A cylindrical container inner surface tester for detecting a defective container by irradiating an inner surface of a cylindrical container using a ring-shaped illuminator concentric with the axis-symmetric cylindrical container, capturing a concentric picture image of the irradiated surface of the cylindrical container using a television camera from above along an axis of the container, and analyzing the captured concentric picture image, comprising:

a frame memory means for storing, as screen data corresponding to a screen displaying the captured image, a multi-value continuous tone image signal as an analog/digital conversion signal of a continuous tone image signal obtained by scanning a screen displaying the captured image, dividing means for dividing an image area on an inner surface of the cylindrical container into a plurality of window areas through which a picture element indicating a defect can be detected;

first setting means for setting for each of the window areas, a first difference binary threshold for detection of a picture element indicating a defect (hereinafter referred to as a first difference level);

obtaining means for obtaining a number of picture elements indicating a defect in each window area by converting to a binary with said first difference level set for each window area an absolute value of a difference obtained by subtracting a value of a target picture element in a screen scanning line for a multi-valve continuous tone image signal read by scanning a frame memory from a value of a background picture element backward or forward by a number of picture elements predetermined for a corresponding window area; and determining means for determining whether or not the cylindrical container is defective depending on whether or not the above described number of picture elements indicating a defect exceeds a first area threshold for detection of a defective container set for the present window area;

second setting means for setting, for each of the above described window areas, a second difference binary threshold corresponding to a difference at least higher than the first difference level (hereinafter referred to as a second difference level), and a second area threshold having a value larger than the first area threshold for detection of a major-defective container if at least the first difference level is equal to the second difference level; and outputting means for outputting a major defect detection signal indicating that the container is a major-defective container externally, if a number of picture elements for each window area in which a binary conversion level is represented by the second difference level exceeds the second area threshold set for each window area.

15. The cylindrical container inner surface tester according to claim 8, wherein required amount of hardware can be reduced by equalizing said first difference level or said first area threshold to said second difference level or said second area threshold respectively.

* * * * *

UNITED STATES PATENT AND TRADEMARK OFFICE
CERTIFICATE OF CORRECTION

PATENT NO. : 5,453,612
DATED : September 26, 1995
INVENTOR(S) : Toyama et al.

It is certified that error appears in the above-indentified patent and that said Letters Patent is hereby corrected as shown below:

Column 2, line 31, delete "PD(i, j) = i" and insert --PD (i, j) = 1--.

Column 2, line 33, delete "an" and insert --a--.

Column 5, line 10, delete "2)" and insert --(2)--.

Column 5, line 25, delete "POD (i, j) = i" and insert --POD (i, j) = 1--.

Column 7, line 39, delete "en".

Column 10, line 12, delete "eights" and insert --eighth--.

Column 14, line 56, delete "POD(i, j) = i" and insert --POD (i, j) = 1--.

UNITED STATES PATENT AND TRADEMARK OFFICE
CERTIFICATE OF CORRECTION

PATENT NO. : 5,453,612
DATED : September 26, 1995
INVENTOR(S) : Toyama et al.

It is certified that error appears in the above-indentified patent and that said Letters Patent is hereby corrected as shown below:

Column 15, line 35, after "figure" insert --8--.

Column 22, line 23, delete "PC" and insert --PO--.

Signed and Sealed this

Sixth Day of May, 1997

*Attest:*

BRUCE LEHMAN

*Attesting Officer*   Commissioner of Patents and Trademarks